(12) United States Patent
Graupe et al.

(10) Patent No.: US 7,196,099 B2
(45) Date of Patent: Mar. 27, 2007

(54) COMPOUNDS AND COMPOSITIONS AS CATHEPSIN INHIBITORS

(75) Inventors: Michael Graupe, Pacifica, CA (US); James T. Palmer, Corte Madera, CA (US); David John Aldous, Gillette, NJ (US); Sukanthini Thurairatnam, Bedminster, NJ (US)

(73) Assignees: Aventis Pharmaceuticals Inc., Bridgewater, NJ (US); Axys Pharmaceuticals Inc., South San Francisco, CA (US)

( * ) Notice: Subject to any disclaimer, the term of this patent is extended or adjusted under 35 U.S.C. 154(b) by 0 days.

(21) Appl. No.: 10/787,367

(22) Filed: Feb. 26, 2004

(65) Prior Publication Data

US 2004/0192742 A1    Sep. 30, 2004

Related U.S. Application Data

(63) Continuation of application No. PCT/US02/29323, filed on Sep. 16, 2002.

(60) Provisional application No. 60/322,318, filed on Sep. 14, 2001.

(51) Int. Cl.
 A61K 31/4468    (2006.01)
 A61K 31/45     (2006.01)
 C07D 401/12    (2006.01)

(52) U.S. Cl. .................... 514/315; 514/315; 546/192; 546/242

(58) Field of Classification Search ............. 546/192, 546/242; 514/315
See application file for complete search history.

(56) References Cited

U.S. PATENT DOCUMENTS

| | | | |
|---|---|---|---|
| 4,927,809 A | 5/1990 | Stuber et al. | |
| 5,424,325 A | 6/1995 | Ando et al. | |
| 5,486,623 A | 1/1996 | Zimmerman et al. | |
| 5,498,616 A | 3/1996 | Mallano et al. | |
| 5,672,583 A * | 9/1997 | Chapman et al. | 514/19 |
| 5,847,135 A | 12/1998 | Bemis et al. | |
| 5,852,007 A | 12/1998 | Chatterjee et al. | |
| 5,874,424 A | 2/1999 | Batchelor et al. | |
| 5,998,390 A | 12/1999 | Ramamurthy et al. | |
| 6,004,933 A | 12/1999 | Spruce et al. | |
| 6,015,791 A | 1/2000 | Gyorkos et al. | |
| 6,022,861 A | 2/2000 | Scarborough et al. | |
| 6,114,310 A | 9/2000 | Chamberland et al. | |
| 6,124,333 A | 9/2000 | Miller et al. | |
| 6,255,453 B1 | 7/2001 | Gyorkos | |
| 6,353,017 B1 | 3/2002 | Altman et al. | |
| 6,455,502 B1 | 9/2002 | Bryant et al. | |
| 6,476,026 B1 | 11/2002 | Bryant et al. | |
| 6,492,362 B1 | 12/2002 | Graupe et al. | |
| 6,506,733 B1 | 1/2003 | Buysse | |
| 6,576,630 B1 | 6/2003 | Link et al. | |
| 6,608,057 B2 | 8/2003 | Cywin et al. | |
| 2002/0017922 A1 | 2/2002 | Graupe et al. | |

FOREIGN PATENT DOCUMENTS

| | | |
|---|---|---|
| EP | 0272671 | 6/1988 |
| EP | 0355572 | 2/1990 |
| EP | 0376012 | 7/1990 |
| EP | 0419683 | 4/1991 |
| EP | 0536399 | 4/1993 |
| EP | 0652009 | 10/1995 |
| EP | 0754454 | 1/1997 |
| EP | 0291234 | 11/1998 |
| JP | 42009133 | 5/1967 |
| JP | 63303868 | 12/1988 |
| JP | 06192199 | 7/1994 |
| JP | 2001-011037 | 1/2001 |
| JP | 2001-055366 | 2/2001 |
| WO | WO 95/13069 | 5/1995 |
| WO | WO 95/15309 | 6/1995 |
| WO | WO 95/24382 | 9/1995 |
| WO | WO 96/21655 | 7/1996 |
| WO | WO 96/30353 | 10/1996 |
| WO | WO 96/40647 | 12/1996 |
| WO | WO 96/40744 | 12/1996 |
| WO | WO 96/41638 | 12/1996 |
| WO | WO 97/03679 | 2/1997 |
| WO | WO 98/01133 | 1/1998 |
| WO | WO 98/01428 | 1/1998 |
| WO | WO 98/05336 | 2/1998 |
| WO | WO 98/08867 | 3/1998 |
| WO | WO 98/21168 | 5/1998 |
| WO | WO 98/23588 | 6/1998 |
| WO | WO 98/49190 | 11/1998 |
| WO | WO 98/08802 | 3/1999 |
| WO | WO 99/24460 | 5/1999 |

(Continued)

OTHER PUBLICATIONS

U.S. Appl. No. 10/035,783, filed Dec. 24, 2001, Graupe et al.

(Continued)

*Primary Examiner*—Golam M. M. Shameem
*Assistant Examiner*—Janet L. Coppins
(74) *Attorney, Agent, or Firm*—Synnestvedt & Lechner LLP

(57) ABSTRACT

The present invention relates to novel cathepsin S inhibitors, the pharmaceutically acceptable salts and N-oxides thereof, their uses as therapeutic agents and the methods of their making.

13 Claims, No Drawings

FOREIGN PATENT DOCUMENTS

| WO | WO 00/48992 | 8/2000 |
| --- | --- | --- |
| WO | WO 00/49007 | 8/2000 |
| WO | WO 00/49008 | 8/2000 |
| WO | WO 00/51998 | 9/2000 |
| WO | WO00/59861 | 10/2000 |
| WO | WO 00/59881 | 10/2000 |
| WO | WO 00/69855 | 11/2000 |
| WO | WO 01/09110 | 2/2001 |
| WO | WO01/09169 | 2/2001 |
| WO | WO 01/19796 | 3/2001 |
| WO | WO 01/19808 | 3/2001 |
| WO | WO 01/30772 | 5/2001 |
| WO | WO 01/55125 | 8/2001 |
| WO | WO 01/58886 | 8/2001 |
| WO | WO 01/19816 | 9/2001 |
| WO | WO02/20485 | 3/2002 |
| WO | WO02/096692 | 5/2002 |
| WO | WO02/057248 | 7/2002 |
| WO | WO02/057249 | 7/2002 |
| WO | WO02/057270 | 7/2002 |
| WO | WO02/100849 | 12/2002 |

OTHER PUBLICATIONS

U.S. Appl. No. 10/294,626, filed Nov. 14, 2002, Li et al.
U.S. Appl. 10/719,080, filed Nov. 21, 2003, Graupe et al.
U.S. Appl. No. 10/416,183, filed Oct. 23, 2003, Li et al.
Adams, et al., Potent and Selective Inhibitors of the Proteasom: Dipeptidyl Boronio Acids, Bioorganic & Medicinal Chemistry Letters, 8: 333-338 (1998).
Ashworth, et al., 4-Cyanothiazolidides as very potent, stable inhibitos of dipeptidyl peptidase IV, Bioorganic & Med. Chem. Letters, B,Oxford, 6(22):2745-2748 (1996).
Bergeman, et al., Studies on the reactivity of .alpha.-cyano.alpha. Isocyano alkanoates. Versitile synthons for the assembly of imidzaoles, Helv.Chim. ACTA, 82(6):909-918 (1999).
Billson, et al., The Design and Synthesis of Inhibitors of the Cysteinyl , Bioorg. Med. Chem. Lett. vol. 8, pp. 993-998, 1998.
Bromme, et al., Potent Inactivation of Cathepsins S and L , Biol. Chem. Hoppe-Seyler. vol. 376, No. 5, pp. 343-347, 1994.
Chatterjee, et al., D-Amino Acid Containing, High-Affinity Inhibitors of Recombinant Human Calpain I. Journal of Medicinal Chemistry, vol. 41, No. 15, p. 2663-2666 (1998).
Cohen, et al., Therapy of relapsing multiple sclerosis. Treatment approaches for nonresponders, Journal of Neuroimmunology, 98: 29-36 (1999).
Dufour, et al., Engineering nitrile hydratase activity into a cysteine protease by a single mutation, Bio.chemistry, US, Am. Chem. Soc., Easton, PA, 34(50):16382-16388 (1995).
Edwards, et al., Design, Synthesis, and Kinetic Evaluation of a Unique Class of Elastase Inhibitors, the Peptidyl a-Ketobanzoxazoles, and the X-ray Crystal Structure of the Covalent Complex between Porcine Pancreatic Elastase and Ac-Ala-Pro-Val-2-Benzoxazole, Journal of American Chemical Society, vol. 114, No. 5, p. 1854-1863 (1992).
Evoli, et al., abstract only, Drugs, 1996, 52(5), 662-70.
Gour-Salin, et al., Inhibition of papain by peptide nitriles: conversion of the nitrile group into other functionalities via the papain-:nitrile thiomidate ester adduct, Can. J. of Chem, CA, National Research Council. Ottawa, 69(8):1288-1297 (1991).
Hallegua, et al., Cyclosporine for lupus membranous nephritis: experiences with ten patients and review of the literature, Lupus, 9: 241-251 (2000).
Hanzlik, et al., Reversible covalent binding of peptide nitriles to papain, Biochim. Biophys, Acta, vol. 1035, No. 1, 1990, pp. 62-70.
Harris, et al., Characteristics of a continuous fluorogenic assay for calpain I. Kinetic evaluation of peptide aldehydes, halomethyl ketones and )achalasia) methyl ketones as inhibitors of the enzyme, Chemical Abstracts, 110:7, Bioorg. Med. Chem. Lett, 5(4) 393-398 (1995).

Heitmiller, R.F., abstract only., Semin. Thorac. Cardiovasc. Surg., 1999, 11(1), 41-6.
Katritzky, et al., Benzotriazole-assisted synthesis of alpha.-(acylamino) nitriles and a conceptually novel method for peptide elongation, Chem. Soc., Perkin Trans. 1(7):1853-1857 (1990).
Khamashta, et al., Expert. Opin. Investig. Drugs, 2000, 9(7), 1581-93.
Krantz, et al., Peptidyl (Acyloxy)methyl Ketones and the Quiescent, Biochemistry. vol. 30, pp. 4678-4687, 1991.
Levy, E.G., Baillieres Clin. Endocrinol. Metab., 1997, 11(3) 585-595.
Li, et al., Aminoacytpyrrolidine-2-nitriles: Potent and stable inhibitors of dipeptidyl-peptidase IV (CD 26), Archives of Biochem. and Bioph., 323(1)148-154 (1995).
Lipshutz, et al., Chiral induction in orginally racemic amino acids via 5-acyl and 5-acyloxyaminooxazoles, Isr, J. Chem. 27(1):49-55 (1986), abstract.
Lipshutz, et al., Heterocycles as masked diamide/dipeptide equivalents. Formation and reactions of substituted 5-(acylamino)oxazoles as Intermediates en route to the cyclopeptide alkaloids, .Am. Chem. Soc., 105(26):7703-7713 (1983).
Lipshutz, et al., Oxazolophanes as masked cyclopeptide alkaloid equivalents: cyclic peptide chemistry without peptide couplings, J. Am. Chem. Soc., 112(19):7032-7041 (1990).
Marquis, et al., Potent dipeptidylketone inhibitors of the cysteine protease cathepsin, Chemical Abstracts, 7:4 581-588 (1999).
McMath, et al., Direct dialkylation of peptide nitriles. Application of the synthesis of 1-aminocyclopropane-1 carboxylic acid (Acc)-containing dipeptides, Bull. Soc. Chim. Fr. 134(1):105-110 (1997).
Moriya, et al., Synthesis and Hypolipidemic Activities of 5-Thienyl-4-oxazoleacetic Acid Derivatives.sup.1, J. Med. Chem., 29: 333-341 (1986).
Moser, et al., 130 Poly (dipeptamidinium)-Salze: definition und metoden zur praparativen herstellung) poly (dipeptamidinium) salts: definition and methods of preparation, Helvitica Chimica ACTA, CH, Verlag, Basel 69:1224-1262 (1986).
Nippon, K., Patent Abstracts of Japan, Publication No. 63301868, 013(197)(1988), abstract.
North, et al., Synthetic studies towards cyclic peptides. Concise synthesis of thiazoline and thiazole containing amino acids, Tetrahedron, 46(24):8627-8290 (1990).
Ogilvie, et al., Peptidomimetic Inhibitors of the human cytomegalovirus protease, Journal of Medicinal Chemistry vol. 40 No. 25 (1997).
Picken, et al., Inhibition of bovine cathepsin B by amino acid-derived nitriles, Biochemical Society Transactions, vol. 18, No. 2, p. 316 (1990).
Pliura, et al. Comparative behavior of colpain and cathepsin B . Biochem. J. vol. 288, pp. 759-762, 1992.
Polman, et al., Drug treatment of multiple aclerosis , BMJ, 321: 19-26 (2000).
Riese, et al., Essential Role of Cathesin S in MHC Class II-Associated Invariant Chain Processing and Peptide Loading, Immunity, 4: 357-366 (Apr. 1996).
Smith, et al., New Inhibitors of Cysteine Proteinases, J. Am. Chem. Soc. vol. 110, No. 13, pp. 4429-4431, 1988.
Suave, et al., Carboxylmodified amino acids and peptides, J An efficient method for the synthesis of monofunctionalized enamines and monofunctionalized methyl ketone derivatives from thioamides via episulfides and thloiminium salts, Tetrahedron Lett, 29:19 2295-2298 (1988).
Suzue, S., Hepatic agents, I. Synthesis of aminocyl (and hydroxyacyl) aminoacetonitriles, Chem. and Pharm. Bull. (Tokyo) (1968), 16(8), 1417-32.
Suzue, et al., Studies on Heptic Agents , Chem. Pharm. Bull. vol. 16, No. 8, pp. 1417-1432, Aug. 1968.
Suzuki, et al., Synthesis of 2-Aryl-4(3-thienyl)imidazole Derivatives with Antinflammatory Properties .sup.1), Chem. Pharm. Bull, 34(8): 3111-3120 (1996).
Tao, et al., Inhibition of Calpain By Peptidyl Heterocycles, Bioorganic & Medicinal Chemistry Letters, 6:24 3009-3112 (1996).

Thompson, et al., Carboxy-modified amino acids and peptides as protease inhibitors, J. Med. Chem., 29(1):104-111 (1986).

Tsutsumi, et al., Synthesis and Structure-Activity Relationships of Peptidyl a-Keto Heterocycles as Novel Inhibitors of Prolyl Endopeptidase, Journal of Medicinal Chemistry, vol. 37, No. 21, p. 3492-3502 (1994).

Vargha, E., Peptide derivatives. VI. N-protected di- and tripeptide nitriles, Stud. Univ. Babes-Bolyai, Ser. Chem., 13(2):31-5 (English abstract of article in Romanian) (1968).

Varghese, The structure and resonance Raman spectra—structure correlations for methyloxycarbonyl-L-phenylalanyl-L-alanine ethyl dithioester, Can. J. Chem., 64(8):1668-1673 (1986).

Yamada, et al., Studies of unusual amino acids and their peptides, IX. The synthetic study of bottomycins B1 and B2, Bul. Chem. Soc., Jpn. 51(3):878-83 (1976), abstract.

Derwent Abstract of Japanese Patent Application 06-192199 , (Jul. 12, 1994).

U.S. Appl. No. 09/927,186, filed Aug. 10, 2001, Cai et al.
U.S. Appl. No. 09/927,324, filed Aug. 10, 2001, Butler et al.
U.S. Appl. No. 09/928,122, filed Aug. 10, 2001, Breitenbucher et al.
U.S. Appl. No. 09/946,214, filed Sep. 5, 2001, Gu et al.
U.S. Appl. No. 10/042,565, filed Nov. 16, 2001, Quibell et al.
U.S. Appl. No. 10/148,612, filed Aug. 21, 2002, Ohmoto et al.
U.S. Appl. No. 10/148,613, filed Aug. 28, 2002, Ohmoto et al.
U.S. Appl. No. 10/181,713, filed Jul. 22, 2002, Ohmoto et al.
U.S. Appl. No. 10/161,799, filed Jul. 23, 2002, Ohmoto et al.
U.S. Appl. No. 10/231,425, filed Aug. 26, 2002, Buxton et al.
U.S. Appl. No. 10/256,512, filed Sep. 27, 2002, Bekkali et al.
U.S. Appl. No. 10/258,053, filed Oct. 17, 2002, Cummings et al.
U.S. Appl. No. 10/275,583, filed Nov. 7, 2002, Cowen et al.
U.S. Appl. No. 10/279,424, filed Oct. 24, 2002, Bekkali et al.
U.S. Appl. No. 10/466,385, filed Jan. 8, 2004, Quibell et al.

Chapman, et al., Emerging Roles for Cysteine Proteases in Human Biology, Ann. Rev. Physiol.; 1997; 59; pp. 63-88.

Dranoff, et al., Cathepsin S Required for Normal MHC Class II Peptide Loading and Germinal Center Development, Immunity; 1999; 10; pp. 197-206.

Fenwick, et al., Diastereoselective Synthesis, Activity and Chiral Stability of Cyclic Alkoxyketone Inhibitors of Cathepsin K., Bioorg. Med. Chemm. Lett.; 2001; 11(2); pp. 199-202.

Fenwick, et al., Solid-phase Synthesis of Cyclic Alkoxyketones, Inhibitors of the Cysteine Protease Cathepsin K., Bioorg. Med. Chem. Lett.; 2001; 11(2); pp. 195-198.

Greenspan, et al., Identification of Dipeptidyl Nitriles as Potent and Selective Inhibitors of cathepsin B Through Structure-based Drug Design, J. Med. Chem.; 2001; 44; pp. 4524-4534.

Lowe, et al., Kinetic Specificity In Papain-catalyzed Hydrolysea, Biochem. J.; 1971; 124(1); pp. 107-115.

Maciewicz, et al., A comparison of Four Cathepsins (B,L,N and S) with Collagenolytic Activity From Rabbit Spleen, Biochem J.; 1998; 256; pp. 433-440.

Marquis, et al., Azeanone-based Inhibitors of Human and Rat Cathepsin K., J. Med. Chem.; 2000; 44(9); pp. 1380-1395.

Nakagawa, et al., Impaired Invariant Chain Degradation and Antigen Presentation and Diminished Collagen-induced Arthrilis in Cathepsin S-null Mice, Immunity; 1999; 10; pp. 207-217.

Otto, et al., Cysteine Proteases and their Inhibitors, Chem. Rev.; 1997; 97; pp. 133-171.

Shi, et al., Molecular Cloning and Expression of Human Alveolar Macrophage Cathepsin S, an Elastinolytic Cysteine Protease, J. Biol. Chem.; 1992; 267; pp. 7258-7262.

Singh, et al. beta-lactams as Enzyme Inhibitors., IDrugs; 2000; 3(5); pp. 512-517.

Villadangos, et al., Cathepsin S Activity Regulates Antigen Presentation and Immunity, J. Clin. Invest.; 1998; 101(10); pp. 2351-2363.

* cited by examiner

COMPOUNDS AND COMPOSITIONS AS CATHEPSIN INHIBITORS

This application is a continuation of International Application No. PCT/US02/29323, filed Sep. 16, 2002, which claims the benefit of Provisional Application No. 60/322,318 filed on Sep. 14, 2001.

This Application relates to compounds and compositions for treating diseases associated with cysteine protease activity, particularly diseases associated with activity of cathepsin S.

DESCRIPTION OF THE FIELD

Cysteine proteases represent a class of peptidases characterized by the presence of a cysteine residue in the catalytic site of the enzyme. Cysteine proteases are associated with the normal degradation and processing of proteins. The aberrant activity of cysteine proteases, e.g., as a result of increase expression or enhanced activation, however, may have pathological consequences. In this regard, certain cysteine proteases are associated with a number of disease states, including arthritis, muscular dystrophy, inflammation, tumor invasion, glomerulonephritis, malaria, periodontal disease, metachromatic leukodystrophy and others. An increase in cathepsin S activity contributes to the pathology and/or symptomatology of a number of diseases. Accordingly, molecules that inhibit the activity of cathepsin S protease are useful as therapeutic agents in the treatment of such diseases.

SUMMARY OF THE INVENTION

This Application relates to compounds of Formula I:

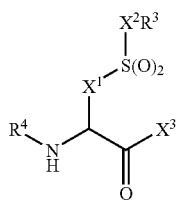

in which:

$X^1$ and $X^2$ are both methylene or $X^1$ is ethylene and $X^2$ is a bond;

$R^3$ is —$CR^5$=$CHR^6$, —$CR^5(CR^6{}_3)_2$ or —$CR^7$=$NR^8$, wherein $R^5$ is hydrogen and $R^6$ is hydrogen or $(C_{1-4})$alkyl or $R^5$ and $R^6$ together with the atoms to which $R^5$ and $R^6$ are attached form $(C_{3-12})$cycloalkenyl, hetero$(C_{5-12})$cycloalkenyl, $(C_{6-12})$aryl, hetero$(C_{6-12})$aryl, $(C_{9-12})$bicycloaryl or hetero$(C_{8-12})$bicycloaryl and $R^7$ and $R^8$ together with the atoms to which $R^7$ and $R^8$ are attached form hetero$(C_{5-12})$cycloalkenyl, hetero$(C_{6-12})$aryl or hetero$(C_{8-12})$bicycloaryl, wherein $R^3$ optionally is substituted by 1 to 5 radicals independently selected from a group consisting of $(C_{1-4})$alkyl, cyano, halo, halo-substituted $(C_{1-4})$alkyl, nitro, —$X^4NR^9R^9$, —$X^4OR^9$, —$X^4SR^9$, —$X^4C(O)NR^9R^9$, —$X^4C(O)OR^9$, —$X^4S(O)R^{10}$, —$X^4S(O)_2R^{10}$ and —$X^4C(O)R^{10}$, wherein $X^4$ is a bond or $(C_{1-2})$alkylene, $R^9$ at each occurrence independently is hydrogen, $(C_{1-3})$alkyl or halo-substituted $(C_{1-3})$alkyl and $R^{10}$ is $(C_{1-3})$alkyl or halo-substituted $(C_{1-3})$alkyl; and $R^4$ is —$C(O)X^5R^{11}$ or —$S(O)_2X^5R^{11}$, wherein $X^5$ is a bond, —O— or —$NR^{12}$—, wherein $R^{12}$ is hydrogen or $(C_{1-6})$alkyl, and $R^{11}$ is (i) $(C_{1-6})$alkyl optionally substituted by —$OR^{13}$, —$SR^{13}$, —$S(O)R^{13}$, —$S(O)_2R^{13}$, —$C(O)R^{13}$, —$C(O)OR^{13}$, —$C(O)NR^{13}R^{14}$, —$NR^{13}R^{14}$, —$NR^{14}C(O)R^{13}$, —$NR^{14}C(O)OR^{13}$, —$NR^{14}C(O)NR^{13}R^{14}$ or —$NR^{14}C(NR^{14})NR^{13}R^{14}$, wherein $R^{13}$ is $(C_{3-12})$cycloalkyl$(C_{0-3})$alkyl, hetero$(C_{5-12})$cycloalkyl$(C_{0-3})$alkyl, $(C_{6-12})$aryl$(C_{0-3})$alkyl, hetero$(C_{5-12})$aryl$(C_{0-3})$alkyl, $(C_{9-12})$bicycloaryl$(C_{0-3})$alkyl or hetero$(C_{8-12})$bicycloaryl$(C_{0-3})$alkyl and $R^{14}$ at each occurrence independently is hydrogen or $(C_{1-6})$alkyl, or (ii) $(C_{3-12})$cycloalkyl$(C_{0-3})$alkyl, hetero$(C_{5-12})$cycloalkyl$(C_{0-3})$alkyl, $(C_{6-12})$aryl$(C_{0-3})$alkyl, hetero$(C_{5-12})$aryl$(C_{0-3})$alkyl, $(C_{9-12})$bicycloaryl$(C_{0-3})$alkyl or hetero$(C_{8-12})$bicycloaryl$(C_{0-3})$alkyl or (iii) $(C_{3-6})$cycloalkyl$(C_{0-3})$alkyl, hetero$(C_{5-6})$cycloalkyl$(C_{0-3})$alkyl, phenyl$(C_{0-3})$alkyl or hetero$(C_{5-6})$aryl$(C_{0-3})$alkyl substituted by —$X^6OR^{15}$, —$X^6SR^{15}$, —$X^6S(O)R^{15}$, —$X^6S(O)_2R^{15}$, —$X^6C(O)R^{15}$, $X^6C(O)OR^{15}$, —$X^6C(O)NR^{15}R^{16}$, —$X^6NR^{15}R^{16}$, —$X^6NR^{16}C(O)R^{15}$, —$X^6NR^{16}C(O)OR^{15}$, —$X^6NR^{16}C(O)NR^{15}R^{16}$, —$X^6NR^{16}C(O)OR^{16}$, —$X^6NR^{16}C(NR^{16})NR^{15}R^{16}$, wherein $X^6$ is a bond or methylene, $R^{15}$ is $(C_{3-6})$cycloalkyl$(C_{0-3})$alkyl, hetero$(C_{5-6})$cycloalkyl$(C_{0-3})$alkyl, phenyl$(C_{0-3})$alkyl or hetero$(C_{5-6})$aryl$(C_{0-3})$alkyl and $R^{16}$ is hydrogen or $(C_{1-6})$alkyl; wherein $R^4$ optionally further contains 1 to 5 substituents which when occurring within an alicyclic or aromatic ring system are radicals independently selected from a group consisting of $(C_{1-6})$alkyl, $(C_{1-6})$alkylidene, cyano, halo, nitro, halo-substituted $(C_{1-3})$alkyl, —$X^6NR^{17}R^{17}$, —$X^6NR^{17}C(O)OR^{17}$, —$X^6NR^{17}C(O)NR^{17}R^{17}$, —$X^6NR^{17}C(NR^{17})NR^{17}R^{17}$, —$X^6OR^{17}$, —$X^6SR^{17}$, —$X^6C(O)OR^{17}$, —$X^6C(O)NR^{17}R^{17}$, —$X^6S(O)_2NR^{17}R^{17}$, —$X^6P(O)(OR^{18})OR^{17}$, —$X^6OP(O)(OR^{18})OR^{17}$, —$X^6NR^{17}C(O)R^{18}$, —$X^6S(O)R^{18}$, —$X^6S(O)_2R^{18}$ and —$X^6C(O)R^{18}$ and when occurring within an aliphatic moiety are radicals independently selected from a group consisting of cyano, halo, nitro, —$NR^{17}R^{17}$, —$NR^{17}C(O)OR^{17}$, —$NR^{17}C(O)NR^{17}R^{17}$, —$NR^{17}C(NR^{17})NR^{17}R^{17}$, —$OR^{17}$, —$SR^{17}$, —$C(O)OR^{17}$, —$C(O)NR^{17}R^{17}$, —$S(O)_2NR^{17}R^{17}$, —$P(O)(OR^{17})OR^{17}$, —$OP(O)(OR^{17})OR^{17}$, —$NR^{17}C(O)R^{18}$, —$S(O)_2R^{18}$, —$S(O)_2R^{18}$ and —$C(O)R^{18}$, wherein $X^6$ is a bond or $(C_{1-6})$alkylene, $R^{17}$ at each occurrence independently is hydrogen, $(C_{1-6})$alkyl or halo-substituted $(C_{1-3})$alkyl and $R^{18}$ is $(C_{1-6})$alkyl or halo-substituted $(C_{1-3})$alkyl;

$X^3$ is a group of Formula (a), (b), (c), (d), (e), (f), (g) or (h):

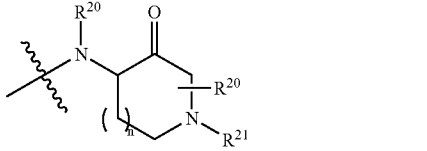
(a)

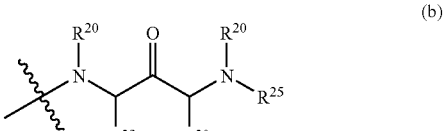
(b)

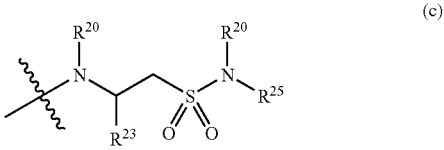
(c)

-continued

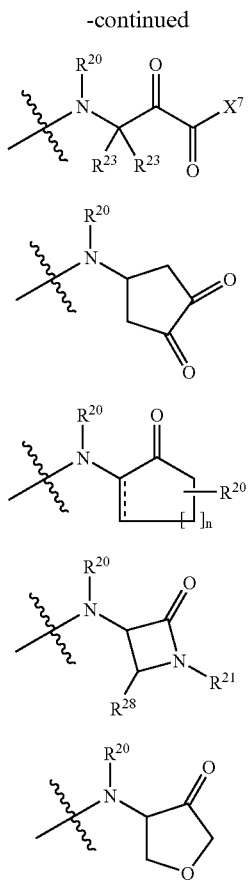

- - - - represents a single bond, or a double bond;

$X^7$ represents aryl, heteroaryl or $NR^{20}R^{25}$;

n is 0, 1 or 2;

$R^{20}$ is selected from the group consisting of hydrogen, $(C_{1-6})$alkyl, $(C_{3-12})$cycloalkyl$(C_{0-6})$alkyl, hetero$(C_{5-12})$cycloalkyl$(C_{0-6})$alkyl, $(C_{6-12})$aryl$(C_{0-6})$alkyl and hetero$(C_{5-12})$aryl$(C_{0-6})$alkyl;

$R^{21}$ is selected from the group consisting of hydrogen, $(C_{1-9})$alkyl, $(C_{3-12})$cycloalkyl$(C_{0-6})$alkyl, hetero$(C_{5-12})$cycloalkyl$(C_{0-6})$alkyl, $(C_{6-12})$aryl$(C_{0-6})$alkyl hetero$(C_{5-12})$aryl$(C_{0-6})$alkyl, $(C_{9-12})$bicycloaryl$(C_{0-3})$alkyl, hetero$(C_{8-12})$-bicycloaryl$(C_{0-3})$alkyl, $—C(O)R^{26}$, $—C(S)R^{26}$, $—S(O)_2R^{26}$, $—C(O)OR^{26}$, $—C(O)N(R^{26})R^{27}$, $—C(S)N(R^{26})R^{27}$ and $—S(O)_2N(R^{27})R^{26}$;

$R^{23}$ is selected from $—H$, $(C_{1-6})$alkyl, $(C_{4-6})$alkenyl, $(C_{3-12})$cycloalkyl$(C_{0-6})$alkyl, hetero$(C_{5-12})$cycloalkyl$(C_{0-6})$alkyl, $(C_{6-12})$aryl$(C_{0-6})$alkyl or hetero$(C_{5-12})$aryl$(C_{0-6})$alkyl optionally substituted with amino, $—NHC(O)R^5$ or $—R^{15}$ wherein $R^{15}$ is as described above;

$R^{25}$ is selected from hydrogen, $(C_{1-6})$alkyl, $(C_{3-12})$cycloalkyl$(C_{0-6})$alkyl, hetero$(C_{5-12})$cycloalkyl$(C_{0-6})$alkyl, $(C_{6-12})$aryl$(C_{0-6})$alkyl, hetero$(C_{5-13})$aryl$(C_{0-6})$alkyl, $—X^4NHR^{15}$, $—X^4S(O)_2R^{26}$ or $—X^4C(O)R^{17}NR^{17}C(O)R^{17}$ wherein $R^{15}$, $R^{17}$ and $X^4$ are as described above;

$R^{26}$ is selected from the group consisting of hydrogen, $(C_{1-6})$alkyl, $(C_{3-12})$cycloalkyl$(C_{0-6})$alkyl, hetero$(C_{5-12})$cycloalkyl$(C_{0-6})$alkyl, $(C_{6-12})$aryl$(C_{0-6})$alkyl, hetero$(C_{5-12})$aryl$(C_{0-6})$alkyl, $(C_{9-12})$bicycloaryl$(C_{0-3})$alkyl and hetero$(C_{8-12})$-bicycloaryl$(C_{0-3})$alkyl;

$R^{27}$ is hydrogen, $(C_{1-6})$alkyl, $(C_{3-12})$cycloalkyl$(C_{0-6})$alkyl, hetero$(C_{5-12})$cycloalkyl$(C_{0-6})$alkyl, $(C_{6-12})$aryl$(C_{0-6})$alkyl or hetero$(C_{5-12})$aryl$(C_{0-6})$alkyl;

$R^{28}$ is $R^{20}$ or $—O—C(=O)—R^{29}$;

$R^{29}$ is $(C_{1-6})$alkyl, $(C_{3-12})$cycloalkyl$(C_{0-3})$alkyl, hetero$(C_{5-12})$cycloalkyl$(C_{0-3})$alkyl, $(C_{6-12})$aryl$(C_{0-3})$alkyl, hetero$(C_{5-12})$aryl$(C_{0-3})$alkyl, $(C_{9-12})$bicycloaryl$(C_{0-3})$alkyl or hetero$(C_{8-12})$bicycloaryl$(C_{0-3})$alkyl;

wherein $X^3$ optionally further contains 1 to 5 substituents which when occurring within an alicyclic or aromatic ring system are radicals independently selected from a group consisting of $(C_{1-6})$alkyl, $(C_{1-6})$alkylidene, cyano, halo, nitro, halo-substituted $(C_{1-3})$alkyl, $—X^6NR^{17}R^{17}$, $—X^6NR^{17}C(O)OR^{17}$, $—X^6NR^{17}C(O)NR^{17}R^{17}$, $—X^6NR^{17}C(NR^{17})NR^{17}R^{17}$, $—X^6OR^{17}$, $—X^6C(O)R^{17}$, $—X^6OR^{15}$, $—X^6SR^{17}$, $—X^6C(O)OR^{17}$, $—X^6C(O)NR^{17}R^{17}$, $—X^6S(O)_2NR^{17}R^{17}$, $—X^6P(O)(OR^8)OR^{17}$, $—X^6OP(O)(OR^8)OR^{17}$, $—X^6NR^{17}C(O)R^{18}$, $—X^6S(O)R^{18}$, $—X^6S(O)_2R^{18}$ and $—X^6C(O)R^{18}$ and when occurring within an aliphatic moiety are radicals independently selected from a group consisting of cyano, halo, nitro, $—NR^{17}R^{17}$, $—NR^{17}C(O)OR^{17}$, $—NR^{17}C(O)NR^{17}R^{17}$, $—NR^{17}C(NR^{17})NR^{17}R^{17}$, $—OR^{17}$, $—SR^{17}$, $—C(O)OR^{17}$, $—C(O)NR^{17}R^{17}$, $—S(O)_2NR^{17}R^{17}$, $—P(O)(OR^{17})OR^{17}$, $—OP(O)(OR^{17})OR^{17}$, $—NR^{17}C(O)R^{18}$, $—S(O)R^{18}$, $—S(O)_2R^{18}$ and $—C(O)R^{18}$, wherein $R^{15}$, $R^{17}$, $R^{18}$ and $X^6$ are as described above.

A second aspect of the invention is a pharmaceutical composition that contains a compound of Formula I or their N-oxide derivatives, individual isomers or mixture of isomers thereof, or pharmaceutically acceptable salts thereof, in admixture with one or more suitable excipients.

A third aspect of the invention is a method for treating a disease in an animal in which inhibition of cathepsin S can prevent, inhibit or ameliorate the pathology and/or symptomatology of the disease, which method comprises administering to the animal a therapeutically effective amount of compound of Formula I or a N-oxide derivative, individual isomer or mixture of isomers thereof; or a pharmaceutically acceptable salt thereof.

A fourth aspect of the invention is the processes for preparing compounds of Formula I and the N-oxide derivatives, prodrug derivatives, protected derivatives, individual isomers and mixtures of isomers thereof; and the pharmaceutically acceptable salts thereof.

DETAILED DESCRIPTION OF THE INVENTION

Definitions:

Unless otherwise stated, the following terms used in the specification and claims are defined for the purposes of this Application and have the following meanings.

"Alicyclic" means a moiety characterized by arrangement of the carbon atoms in closed non-aromatic ring structures having properties resembling those of aliphatics and may be saturated or partially unsaturated with two or more double or triple bonds.

"Aliphatic" means a moiety characterized by a straight or branched chain arrangement of the constituent carbon atoms and may be saturated or partially unsaturated with two or more double or triple bonds.

"Alkyl" represented by itself means a straight or branched, saturated or unsaturated, aliphatic radical having the number of carbon atoms indicated (e.g., $(C_{1-6})$alkyl includes methyl, ethyl, propyl, isopropyl, butyl, sec-butyl, isobutyl, tert-butyl, vinyl, allyl, 1-propenyl, isopropenyl, 1-butenyl, 2-butenyl, 3-butenyl, 2-methylallyl, ethynyl, 1-propynyl, 2-propynyl, and the like). Alkyl represented along with another radical (e.g., as in arylalkyl) means a straight or branched, saturated or unsaturated aliphatic divalent radical having the number of atoms indicated or when no atoms are indicated means a bond (e.g., $(C_{6-10})$aryl$(C_{0-3})$alkyl includes phenyl, benzyl, phenethyl, 1-phenylethyl 3-phenylpropyl, and the like).

"Alkylene", unless indicated otherwise, means a straight or branched, saturated or unsaturated, aliphatic, divalent radical having the number of carbon atoms indicated (e.g., $(C_{1-6})$alkylene includes methylene (—$CH_2$—), ethylene (—$CH_2CH_2$—), trimethylene (—$CH_2CH_2CH_2$—), tetramethylene (—$CH_2CH_2CH_2CH_2$—) 2-butenylene(—$CH_2CH$=$CHCH_2$—), 2-methyltetramethylene (—$CH_2CH(CH_3)CH_2CH_2$—), pentamethylene (—$CH_2CH_2CH_2CH_2CH_2$—) and the like).

"Alkylidene" means a straight or branched saturated or unsaturated, aliphatic, divalent radical having the number of carbon atoms indicated (e.g. $(C_{1-6})$alkylidene includes methylene (=$CH_2$), ethylidene (=$CHCH_3$), isopropylidene (=$C(CH_3)_2$), propylidene (=$CHCH_2CH_3$), allylidene (=$CH$—$CH$=$CH_2$), and the like).

"Amino" means the radical —$NH_2$. Unless indicated otherwise, the compounds of the invention containing amino moieties include protected derivatives thereof. Suitable protecting groups for amino moieties include acetyl, tert-butoxycarbonyl, benzyloxycarbonyl, and the like.

"Animal" includes humans, non-human mammals (e.g., dogs, cats, rabbits, cattle, horses, sheep, goats, swine, deer, and the like) and non-mammals (e.g., birds, and the like).

"Aromatic" means a moiety wherein the constituent atoms make up an unsaturated ring system, all atoms in the ring system are $sp^2$ hybridized and the total number of pi electrons is equal to 4n+2.

"Aryl" means a monocyclic or fused bicyclic ring assembly containing the total number of ring carbon atoms indicated, wherein each ring is comprised of 6 ring carbon atoms and is aromatic or when fused with a second ring forms an aromatic ring assembly. For example, optionally substituted $(C_{6-10})$aryl as used in this Application includes, but is not limited to, biphenyl-2-yl, 2-bromophenyl, 2-bromocarbonylphenyl, 2-bromo-5-fluorophenyl, 4-tert-butylphenyl, 4-carbamoylphenyl, 4-carboxy-2-nitrophenyl, 2-chlorophenyl, 4-chlorophenyl, 3-chlorocarbonylphenyl, 4-chlorocarbonylphenyl, 2-chloro-4-fluorophenyl, 2-chloro-6-fluorophenyl, 4-chloro-2-nitrophenyl, 6-chloro-2-nitrophenyl, 2,6-dibromophenyl, 2,3-dichlorophenyl, 2,5-dichlorophenyl, 3,4-dichlorophenyl, 2-difluoromethoxyphenyl, 3,5-dimethylphenyl, 2-ethoxycarbonylphenyl, 2-fluorophenyl, 2-iodophenyl, 4-isopropylphenyl, 2-methoxyphenyl, 4-methoxyphenyl, 2-methylphenyl, 3-methylphenyl, 4-methylphenyl, 5-methyl-2-nitrophenyl, 4-methylsulfonylphenyl, naphth-2-yl, 2-nitrophenyl, 3-nitrophenyl, 4-nitrophenyl, 2,3,4,5,6-pentafluorophenyl, phenyl, 2-trifluoromethoxyphenyl, 3-trifluoromethoxyphenyl, 4-trifluoromethoxyphenyl, 2-trifluoromethylphenyl, 3-trifluoromethylphenyl, 4-trifluoromethylphenyl, 2-trifluoromethylsulfanylphenyl, 4-trifluoromethylsulfanylphenyl, and the like. Optionally substituted $(C_{6-10})$aryl as used in this Application includes 3-acetylphenyl, 3-tert-butoxycarbonylaminomethylphenyl, biphenyl-4-yl, 3-hydroxyphenyl, 4-hydroxyphenyl, 3-methoxyphenyl, naphth-2-yl, 3-phenoxyphenyl, phenyl, and the like.

"Bicycloaryl" means a bicyclic ring assembly containing the number of ring carbon atoms indicated, wherein the rings are linked by a single bond or fused and at least one of the rings comprising the assembly is aromatic, and any carbocyclic ketone, thioketone or iminoketone derivative thereof (e.g., $(C_{9-10})$bicycloaryl includes cyclohexylphenyl, 1,2-dihydronaphthyl, 2,4-dioxo-1,2,3,4-tetrahydronaphthyl, indanyl, indenyl, 1,2,3,4-tetrahydronaphthyl, and the like).

"Carbamoyl" means the radical —$C(O)NH_2$. Unless indicated otherwise, the compounds of the invention containing carbamoyl moieties include protected derivatives thereof. Suitable protecting groups for carbamoyl moieties include acetyl, tert-butoxycarbonyl, benzyloxycarbonyl, and the like and both the unprotected and protected derivatives fall within the scope of the invention.

"Carbocyclic ketone derivative" means a derivative containing the moiety —$C(O)$—.

"Carboxy" means the radical —$C(O)OH$. Unless indicated otherwise, the compounds of the invention containing carboxy moieties include protected derivatives thereof. Suitable protecting groups for carboxy moieties include benzyl, tert-butyl, and the like.

"Cycloalkyl" means a saturated or partially unsaturated, monocyclic, fused bicyclic or bridged polycyclic ring assembly containing the number of ring carbon atoms indicated, and any carbocyclic ketone, thioketone or iminoketone derivative thereof (e.g., $(C_{3-10})$cycloalkyl includes cyclopropyl, cyclobutyl, cyclopentyl, cyclohexyl, cyclohexenyl, 2,5-cyclohexadienyl, bicyclo[2.2.2]octyl, adamantan-1-yl, decahydronaphthyl, oxocyclohexyl, dioxocyclohexyl, thiocyclohexyl, 2-oxobicyclo[2.2.1]hept-1-yl, and the like).

"Cycloalkylene" means a divalent saturated or partially unsaturated, monocyclic ring or bridged polycyclic ring assembly containing the number of ring carbon atoms indicated, and any carbocyclic ketone, thioketone or iminoketone derivative thereof. For example, the instance wherein "$R^1$ and $R^2$ together with the carbon atom to which both $R^1$ and $R^2$ are attached form $(C_{3-8})$cycloalkylene" includes, but is not limited to, the following:

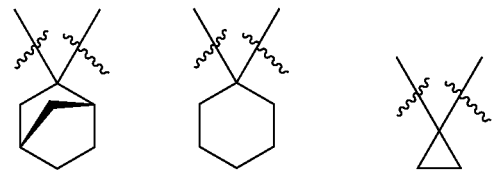

"Disease" specifically includes any unhealthy condition of an animal or part thereof and includes an unhealthy condition that may be caused by, or incident to, medical or veterinary therapy applied to that animal, i.e., the "side effects" of such therapy.

"Halo" means fluoro, chloro, bromo or iodo.

"Halo-substituted alkyl", as an isolated group or part of a larger group, means "alkyl" substituted by one or more "halo" atoms, as such terms are defined in this Application. Halo-substituted alkyl includes haloalkyl, dihaloalkyl, trihaloalkyl, perhaloalkyl and the like (e.g. halo-substituted $(C_{1-3})$alkyl includes chloromethyl, dichloromethyl, difluoromethyl, trifluoromethyl, 2,2,2-trifluoroethyl, perfluoroethyl, 2,2,2-trifluoro-1,1-dichloroethyl, and the like).

"Heteroatom moiety" includes —N=, —NR—, —$N^+$($O^-$)=, —O—, —S— or —$S(O)_2$—, wherein R is hydrogen, $(C_{1-6})$alkyl or a protecting group.

"Heterocycloalkylene" means cycloalkylene, as defined in this Application, provided that one or more of the ring member carbon atoms indicated, is replaced by heteroatom moiety selected from —N=, —NR—, —O—, —S— or —S(O)$_2$—, wherein R is hydrogen or (C$_{1-6}$)alkyl. For example, the instance wherein R$^1$ and R$^2$ together with the carbon atom to which both R$^1$ and R$^2$ are attached form hetero(C$_{3-8}$)cycloalkylene" includes, but is not limited to, the following:

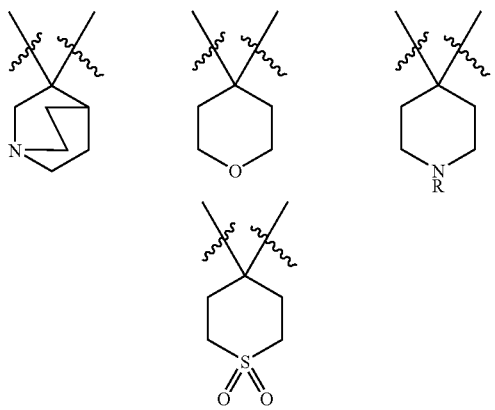

in which R is hydrogen, (C$_{1-6}$)alkyl, or a protecting group.

"Heteroaryl" means aryl, as defined in this Application, provided that one or more of the ring carbon atoms indicated are replaced by a heteroatom moiety selected from —N=, —NR—, —N$^+$(O$^-$)=, —O— or —S—, wherein R is hydrogen, (C$_{1-6}$)alkyl, a protecting group or represents the free valence which serves as the point of attachment to a ring nitrogen, and each ring is comprised of 5 or 6 ring atoms. For example, optionally substituted hetero(C$_{5-13}$)aryl as used in this Application includes, but is not limited to, 4-amino-2-hydroxypyrimidin-5-yl, dibenzofuranyl, benzothiazol-2-yl, 1H-benzoimidazol-2-yl, 2-bromopyrid-5-yl, 5-bromopyrid-2-yl, 4-carbamoylthiazol-2-yl, 3-carboxypyrid-4-yl, 5-carboxy-2,6-dimethylpyrid-3-yl, 3,5-dimethylisoxazol-4-yl, 5-ethoxy-2,6-dimethylpyrid-3-yl, 5-fluoro-6-hydroxypyrimidin-4-yl, fur-2-yl, fur-3-yl, 5-hydroxy-4,6-dimethylpyrid-3-yl, 8-hydroxy-5,7-dimethylquinolin-2-yl, 5-hydroxymethylisoxazol-3-yl, 3-hydroxy-6-methylpyrid-2-yl, 3-hydroxypyrid-2-yl, 1H-imidazol-2-yl, 1H-imidazol-4-yl, 1H-indol-3-yl, isothiazol-4-yl, isoxazol-4-yl, 2-methylfur-3-yl, 5-methylfur-2-yl, 1-methyl-1H-imidazol-2-yl, 5-methyl-3H-imidazol-4-yl, 5-methylisoxazol-3-yl, 5-methyl-2H-pyrazol-3-yl, 3-methylpyrid-2-yl, 4-methylpyrid-2-yl, 5-methylpyrid-2-yl, 6-methylpyrid-2-yl, 2-methylpyrid-3-yl, 2-methylthiazol-4-yl, 5-nitropyrid-2-yl, 2H-pyrazol-3-yl, 3H-pyrazol-4-yl, pyridazin-3-yl, pyrid-2-yl, pyrid-3-yl, pyrid-4-yl, 5-pyrid-3-yl-2H-[1,2,4]triazol-3-yl, pyrimidin-4-yl, pyrimidin-5-yl, 1H-pyrrol-3-yl, quinolin-2-yl, 1H-tetrazol-5-yl, thiazol-2-yl, thiazol-5-yl, thien-2-yl, thien-3-yl, 2H-[1,2,4]triazol-3-yl, 3H-[1,2,3]triazol-4-yl, 5-trifluoromethylpyrid-2-yl, and the like. Suitable protecting groups include tert-butoxycarbonyl, benzyloxycarbonyl, benzyl, 4-methoxybenzyl, 2-nitrobenzyl, and the like. Optionally substituted hetero(C$_{5-10}$)aryl as used in this Application to define R$^4$ includes benzofur-2-yl, fur-2-yl, fur-3-yl, pyrid-3-yl, pyrid-4-yl, quinol-2-yl, quinol-3-yl, thien-2-yl, thien-3-yl, and the like.

"Heterobicycloaryl" means bicycloaryl, as defined in this Application, provided that one or more of the ring carbon atoms indicated are replaced by a heteroatom moiety selected from —N=, —NR—, —O— or —S—, wherein R is hydrogen, (C$_{1-6}$)alkyl, a protecting group or represents the free valence which serves as the point of attachment to a ring nitrogen, and any carbocyclic ketone, thioketone or iminoketone derivative thereof. For example, optionally substituted hetero(C$_{8-10}$)bicycloaryl as used in this Application includes, but is not limited to, 2-amino-4-oxo-3,4-dihydropteridin-6-yl, and the like. In general, the term heterobicycloaryl as used in this Application includes, for example, benzo[1,3]dioxol-5-yl, 3,4-dihydro-2H-[1,8]naphthyridinyl, 3,4-dihydro-2H-quinolinyl, 2,4-dioxo-3,4-dihydro-2H-quinazolinyl, 1,2,3,4,5,6-hexahydro[2,2]bipyridinylyl, 3-oxo-2,3-dihydrobenzo[1,4]oxazinyl, 5,6,7,8-tetrahydroquinolinyl, and the like.

"Heterocycloalkyl" means cycloalkyl, as defined in this Application, provided that one or more of the ring carbon atoms indicated are replaced by a heteroatom moiety selected from —N=, —NR—, —O— or —S—, wherein R is hydrogen, (C$_{1-6}$)alkyl, a protecting group or represents the free valence which serves as the point of attachment to a ring nitrogen, and any carbocyclic ketone, thioketone or iminoketone derivative thereof (e.g., the term hetero(C$_{5-10}$)cycloalkyl includes imidazolidinyl, morpholinyl, piperazinyl, piperidyl, pyrrolidinyl, pyrrolinyl, quinuclidinyl, and the like). Suitable protecting groups include tert-butoxycarbonyl, benzyloxycarbonyl, benzyl, 4-methoxybenzyl, 2-nitrobenzyl, and the like. Both the unprotected and protected derivatives fall within the scope of the invention.

"Hydroxy" means the radical —OH. Unless indicated otherwise, the compounds of the invention containing hydroxy radicals include protected derivatives thereof. Suitable protecting groups for hydroxy moieties include benzyl and the like.

"Iminoketone derivative" means a derivative containing the moiety —C(NR)—, wherein R is hydrogen or (C$_{1-6}$) alkyl.

"Isomers" mean compounds of Formula I having identical molecular formulae but differ in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound with one chiral center has two enantiomeric forms of opposite chirality is termed a "racemic mixture". A compound that has more than one chiral center has $2^{n-1}$ enantiomeric pairs, where n is the number of chiral centers. Compounds with more than one chiral center may exist as ether an individual diastereomers or as a mixture of diastereomers, termed a "diastereomeric mixture". When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992). It is understood that the names and illustration used in this Application to describe compounds of Formula I are meant to be encompassed all possible stereoisomers. Thus, for example, the name morpholine-4-carboxylic acid [1-(1-benzoyl-4-oxo-pyrrolidin-3-ylcarbamoyl)-2-phenyl-methanesulfonyl-ethyl]-amide is meant to include morpholine-4-carboxylic acid [S-1-(1-benzoyl-4-oxo-pyrrolidin-3-ylcarbamoyl)-2-phenylmethanesulfonyl-ethyl]-amide and morpholine-4-carboxylic acid [R-1-(1-benzoyl-4-oxo-pyrrolidin-3-ylcarbamoyl)-2-phenylmethanesulfonyl-ethyl]-amide and any mixture, racemic or otherwise, thereof.

"Ketone derivative" means a derivative containing the moiety —C(O)—. For example, for 2-acetoxy-azetidin-3-yl, the "carbocyclic ketone derivative" would be 2-acetoxy-4-oxo-azetidin-3-yl.

"Nitro" means the radical —$NO_2$.

"Optional" or "optionally" means that the subsequently described event or circumstance may or may not occur, and that the description includes instances where the event or circumstance occurs and instances in which it does not. For example, the phrase "wherein within $R^3$ and $R^4$ any alicyclic or aromatic ring system may be substituted further by 1–5 radicals . . . " means that $R^3$ and $R^4$ may or may not be substituted in order to fall within the scope of the invention.

"Oxoalkyl" means alkyl, as defined above, wherein one of the number of carbon atoms indicated is replaced by an oxygen group (—O—), e.g., oxo($C_{2-6}$)alkyl includes methoxymethyl, etc.

"N-oxide derivatives" means derivatives of compounds of Formula I in which nitrogens are in an oxidized state (i.e., O—N) and which possess the desired pharmacological activity.

"Pathology" of a disease means the essential nature, causes and development of the disease as well as the structural and functional changes that result from the disease processes.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of Formula I which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartatic acid, citric acid, benzoic acid, o-(4-hydroxybenzoyl)benzoic acid, cinnamic acid, madelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanol amine, diethanolamine, triethanol amine, tromethamine, N-methylglucamine and the like.

"Prodrug" means a compound which is convertible in vivo by metabolic means (e.g. by hydrolysis) to a compound of Formula I. For example an ester of a compound of Formula I containing a hydroxy group may be convertible by hydrolysis in vivo to the parent molecule. Alternatively an ester of a compound of Formula I containing a carboxy group may be convertible by hydrolysis in vivo to the parent molecule. Suitable esters of compounds of Formula I containing a hydroxy group, are for example acetates, citrates, lactates, tartrates, malonates, oxalates, salicylates, propionates, succinates, fumarates, maleates, methylene-bis-b-hydroxynaphthoates, gentisates, isethionates, di-p-toluoyl-tartrates, methanesulphonates, ethanesulphonates, benzenesulphonates, p-toluenesulphonates, cyclohexylsulphamates and quinates. Suitable esters of compounds of Formula I containing a carboxy group, are for example those described by F. J. Leinweber, Drug Metab. Res., 1987, 18, page 379. An especially useful class of esters of compounds of Formula I containing a hydroxy group, may be formed from acid moieties selected from those described by Bundgaard et al., J. Med. Chem., 1989, 32, page 2503–2507, and include substituted (aminomethyl)-benzoates, for example, dialkylamino-methylbenzoates in which the two alkyl groups may be joined together and/or interrupted by an oxygen atom or by an optionally substituted nitrogen atom, e.g. an alkylated nitrogen atom, more especially (morpholino-methyl)benzoates, e.g. 3- or 4-(morpholinomethyl)-benzoates, and (4-alkylpiperazin-1-yl)benzoates, e.g. 3- or 4-(4-alkylpiperazin-1-yl)benzoates.

"Protected derivatives" means derivatives of compounds of Formula I in which a reactive site or sites are blocked with protecting groups. Protected derivatives of compounds of Formula I are useful in the preparation of compounds of Formula I or in themselves may be active cathepsin S inhibitors. A comprehensive list of suitable protecting groups can be found in T. W. Greene, *Protecting Groups in Organic Synthesis,* 3rd edition, John Wiley & Sons, Inc. 1999.

"Therapeutically effective amount" means that amount which, when administered to an animal for treating a disease, is sufficient to effect such treatment for the disease.

"Thioketone derivative" means a derivative containing the moiety —C(S)—.

"Treatment" or "treating" means any administration of a compound of the present invention and includes:

(1) preventing the disease from occurring in an animal which may be predisposed to the disease but does not yet experience or display the pathology or symptomatology of the disease, (2) inhibiting the disease in an animal that is experiencing or displaying the pathology or symptomatology of the diseased (i.e., arresting further development of the pathology and/or symptomatology), or (3) ameliorating the disease in an animal that is experiencing or displaying the pathology or symptomatology of the diseased (i.e., reversing the pathology and/or symptomatology).

Nomenclature:

The compounds of Formula I and the intermediates and starting materials used in their preparation are named in accordance with IUPAC rules of nomenclature in which the characteristic groups have decreasing priority for citation as the principle group as follows: acids, esters, amides, etc. Alternatively, the compounds are named by AutoNom 4.0

(Beilstein Information Systems, Inc.). For example, a compound of Formula I in which $R^3$ is phenyl, $R^4$ is morpholine-4-carbonyl and $X^3$ is 1-benzoyl-4-oxo-pyrrolidin-3-ylamino; that is, a compound having the following structure:

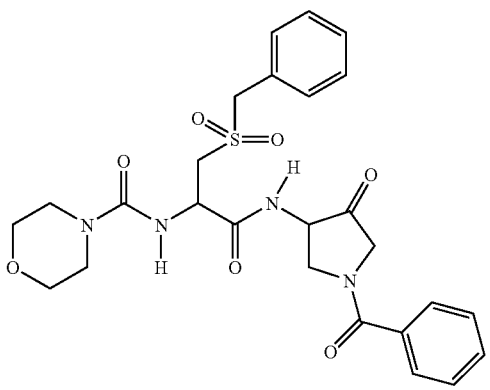

is named morpholine-4-carboxylic acid [1-(1-benzoyl-4-oxo-pyrrolidin-3-ylcarbamoyl)-2-phenylmethanesulfonyl-ethyl]-amide.

Presently Preferred Embodiments

While the broadest definition of the invention is set forth in the Summary of the Invention; certain aspects of the invention are preferred. For example, for a compound of Formula I, in which $X^1$ and $X^2$ are both methylene or $X^1$ is ethylene and $X^2$ is a bond; $R^3$ is —$CR^5$=$CHR^6$, —$CR_5(CR^6{}_3)_2$ or —$CR^7$=$NR^8$, wherein $R^5$ is hydrogen and $R^6$ is hydrogen or $(C_{1-4})$alkyl or $R^5$ and $R^6$ together with the atoms to which $R^5$ and $R^6$ are attached form $(C_{3-12})$cycloalkenyl, $(C_{6-12})$aryl, hetero$(C_{6-12})$aryl or $(C_{9-12})$bicycloaryl and $R^7$ and $R^8$ together with the atoms to which $R^7$ and $R^8$ are attached form hetero$(C_{5-12})$cycloalkenyl or hetero$(C_{6-12})$aryl, wherein $R^3$ optionally is substituted by 1 to 5 radicals independently selected from a group consisting of $(C_{1-4})$alkyl, cyano, halo, halo-substituted $(C_{1-4})$alkyl, —$X^4OR^9$ and —$X^4C(O)OR^9$, wherein $X^4$ is a bond or $(C_{1-2})$alkylene, $R^9$ at each occurrence independently is $(C_{1-3})$alkyl or halo-substituted $(C_{1-3})$alkyl; $R^4$ is —$C(O)X^5R^{11}$ or —$S(O)_2X^5R^{11}$, wherein $X^5$ is a bond, —O— or —$NR^{12}$—, wherein $R^{12}$ is hydrogen or $(C_{1-6})$alkyl, and $R^{11}$ is (i) $(C_{1-6})$alkyl or (ii) hetero$(C_{5-12})$cycloalkyl$(C_{0-3})$alkyl, $(C_{6-12})$aryl$(C_{0-3})$alkyl, hetero$(C_{5-12})$aryl$(C_{0-3})$alkyl, $(C_{9-12})$bicycloaryl$(C_{0-3})$alkyl or hetero$(C_{8-12})$bicycloaryl$(C_{0-3})$alkyl or (iii) hetero$(C_{5-6})$cycloalkyl$(C_{0-3})$alkyl or phenyl$(C_{0-3})$alkyl substituted by —$X^6OR^{15}$, —$X^6C(O)R^{15}$ or —$X^6NR^{16}C(O)OR^{16}$, wherein $X^6$ is a bond or methylene, $R^{15}$ is phenyl$(C_{0-3})$alkyl or hetero$(C_{5-6})$aryl$(C_{0-3})$alkyl and $R^{16}$ is hydrogen or $(C_{1-6})$alkyl; wherein $R^4$ optionally further contains 1 to 5 substituents which when occurring within an alicyclic or aromatic ring system are radicals independently selected from a group consisting of $(C_{1-6})$alkyl, halo, —$X^6NR^{17}R^{17}$, —$X^6OR^{17}$, —$X^6C(O)OR^{17}$, —$X^6NC(O)R^{16}$ and —$X^6C(O)R^{18}$, $R^{17}$ at each occurrence independently is hydrogen, $(C_{1-6})$alkyl or halo-substituted $(C_{1-3})$alkyl and $R^{18}$ is $(C_{1-6})$alkyl or halo-substituted $(C_{1-3})$alkyl.

In particular, $X^3$ is a group of Formula (a), (b) or (c) in which: n is 0, 1 or 2; $R^{20}$ is selected from the group consisting of hydrogen and $(C_{1-6})$alkyl; $R^{21}$ is selected from the group consisting of $(C_{1-9})$alkyl, $(C_{6-12})$aryl$(C_{0-6})$alkyl, —$C(O)R^{26}$, —$S(O)_2R^{26}$, —$C(O)OR^{26}$ and —$C(O)N(R^{26})R^{27}$; $R^{23}$ is selected from $(C_{1-6})$alkyl optionally substituted with amino, —$NHC(O)R^{15}$ or —$R^{15}$ wherein $R^{15}$ is as described above; $R^{25}$ is selected from $(C_{1-6})$alkyl, $(C_{6-12})$aryl$(C_{0-6})$alkyl, —$X^4S(O)_2R^{26}$ or —$X^4C(O)R^{17}NR^{17}C(O)R^{17}$ wherein $R^{17}$ and $X^4$ are as described above and $R^{26}$ is as described below; $R^{26}$ is selected from the group consisting of $(C_{1-6})$alkyl, hetero$(C_{5-12})$cycloalkyl$(C_{0-6})$alkyl, $(C_{6-12})$aryl$(C_{0-6})$alkyl, hetero$(C_{5-12})$aryl$(C_{0-6})$alkyl and $(C_{9-12})$bicycloaryl$(C_{0-3})$alkyl; $R^{27}$ is $(C_{1-6})$alkyl; herein $X^3$ optionally further contains 1 to 5 substituents which when occurring within an alicyclic or aromatic ring system are radicals independently selected from a group consisting of $(C_{1-6})$alkyl, cyano, halo, —$X^6OR^{17}$, —$X^6C(O)R^{17}$ and —$X^6OR^{15}$.

$R^3$ more preferably is selected from the group consisting of phenyl, pyridin-2-yl, pyridin-3-yl, pyridin-4-yl, vinyl, 2-difluoromethoxyphenyl, 1-oxy-pyridin-2-yl, 4-methoxyphenyl, 4-methylphenyl, 2-methylphenyl, 4-chlorophenyl, 3,5-dimethylphenyl, 4-trifluoromethylphenyl, 4-trifluoromethoxyphenyl, 2-bromophenyl, naphthalen-2-yl, 3,4-dichlorophenyl, 3-methylphenyl, 3-trifluoromethylphenyl, 3-trifluoromethoxyphenyl, 2,3,4,5,6-pentafluoro-phenyl, 2-fluorophenyl, 2-chlorophenyl, 2-cyano-phenyl, 2-trifluoromethylphenyl, 4-tert-butyl-phenyl, 3-chlorophenyl, 4-bromophenyl, 2-fluoro-3-chloro-phenyl, 2-fluoro-3-methyl-phenyl, 3-fluorophenyl, 2,5-difluorophenyl, 3-bromophenyl, 2,5-dichlorophenyl, 2,6-difluorophenyl, 3-cyano-phenyl, 4-cyano-phenyl, 2-trifluoromethoxyphenyl, 2,3-difluorophenyl, biphenyl, 2-bromo-5-fluoro-phenyl, 4-fluorophenyl, 3,4-difluorophenyl, 2,4-difluorophenyl, 2,4,6-trifluorophenyl, 2,4,5-trifluorophenyl, 2,3,4-trifluorophenyl, 2-chloro-5-trifluoromethylphenyl, 2,4-bis-trifluoromethylphenyl, 2,5,6-trifluorophenyl, 2-fluoro-3-trifluoromethylphenyl, 2-fluoro-4-trifluoromethylphenyl, 2-fluoro-5-trifluoromethylphenyl, 2,3,5-trifluorophenyl, 2-fluoro-5-trifluoromethylphenyl, 5-fluoro-2-trifluoromethylphenyl, 4-fluoro-3-trifluoromethylphenyl, 2-methoxyphenyl, 3,5-bis-trifluoromethylphenyl, 4-difluoromethoxyphenyl, 3-difluoromethoxyphenyl, 2,6-dichlorophenyl, 4-carboxyphenyl, cyclohexyl, cyclopropyl, isopropyl, thiophen-2-yl, 5-chloro-thiophen-2-yl and 3,5-dimethyl-isoxazol-4-yl.

$R^4$ more preferably is selected from the group consisting of benzoyl, morpholine-4-carbonyl, acetyl, furan-3-carbonyl, 2-methoxy-benzoyl, 3-methoxy-benzoyl, naphthalene-2-carbonyl, benzo[1,3]dioxole-5-carbonyl, 3-pyridin-3-yl-acryloyl, benzofuran-2-carbonyl, furan-2-carbonyl, tert-butoxy-carbonyl, biphenyl-4-carbonyl, quinoline-2-carbonyl, quinoline-3-carbonyl, 3-acetyl-benzoyl, 4-phenoxy-benzoyl, 3-hydroxy-benzoyl, 4-hydroxy-benzoyl, pyridine-3-carbonyl, 3-(tert-butoxycarbonylamino-methyl)-benzoyl, 4-carbonyl-piperazine-1-carboxylic acid tert-butyl ester, 4-carbonyl-piperazine-1-carboxylic acid ethyl ester, 4-(furan-2-carbonyl)-piperazine-1-carbonyl, pyridine-4-carbonyl, 1-oxy-pyridine-4-carbonyl, 1-oxy-pyridine-3-carbonyl, thiophene-2-carbonyl, thiophene-3-carbonyl, 4-benzoyl-benzoyl, 5-methyl-thiophene-2-carbonyl, 3-chloro-thiophene-2-carbonyl, 3-bromo-thiophene-2-carbonyl, 4-chloro-benzoyl, 3-flouro-4-methoxy-benzoyl, 4-methoxy-benzoyl, 4-triflouromethoxy-benzoyl, 3,4-diflouro-benzoyl, 4-fluoro-benzoyl, 3,4-dimethoxy-benzoyl, 3-methyl-benzoyl, 4-bromo-benzoyl, 4-triflouromethyl-benzoyl, 3-benzoyl-benzoyl, cyclopentane-carbonyl, benzo[b]thiophene-2-carbonyl, 3-chloro-benzo[b]thiophene-2-carbonyl, benzenesulfonyl, naphthalene-2-sulfonyl, 5-methyl-thiophene-2-sulfonyl, thiophene-2-sulfonyl, formamylmethyl ester, 4-methyl-pentanoyl, formamyl-isobutyl ester, formamyl-monoallyl ester, formamyl-isopropyl ester, N,N-dimethyl-formamyl, N-isopropyl-formamyl, N-pyridin-4- yl-formamyl, N-pyridin-3-yl-formamyl, 3-phenyl-acryloyl, 1H-indole-5-carbonyl, pyridine-2-carbonyl, pyrazine-2-carbonyl, 3-hydroxy-pyridine-2-carbonyl, 2-amino-pyridine-3-carbonyl, 2-hydroxy-pyridine-3-carbonyl, 6-amino-pyridine-3-carbonyl, 6-hydroxy-pyridine-3-carbonyl, pyridazine-4-carbonyl, 3-phenoxy-benzoyl and 1-oxo-1,3-dihydro-isoindole-2-carbonyl.

$X^3$ more preferably is selected from a group consisting of 4-amino-3-oxo-azepane-1-carboxylic acid benzyl ester, 4-amino-3-oxo-azepane-1-carboxylic acid isobutyl ester, 4-amino-1-benzoyl-azepan-3-one, 4-amino-1-benzenesulfonyl-azepan-3-one, 4-amino-1-(pyridine-2-sulfonyl)-azepan-3-one, 4-amino-1-(1-oxy-pyridine-2-sulfonyl)-azepan-3-one, 4-amino-1-(3,4-dichloro-benzenesulfonyl)-azepan-3-one, 4-amino-1-(2-flouro-benzenesulfonyl)-azepan-3-one, 4-amino-1-(3,4-dimethoxy-benzenesulfonyl)-azepan-3-one, 4-amino-1-(2-cyano-benzenesulfonyl)-azepan-3-one, 4-amino-1-(naphthalene-1-sulfonyl)-azepan-3-one, 4-amino-1-(thiophene-2-sulfonyl)-azepan-3-one, 4-amino-1-(thiazole-2-sulfonyl)-azepan-3-one, 4-amino-1-(pyrrolidine-1-sulfonyl)-azepan-3-one, 4-amino-1-methanesulfonyl-azepan-3-one, 4-amino-1-(pyrrolidine-1-carbonyl)-azepan-3-one, 4-amino-3-oxo-azepane-1-carboxylic-acid-dimethylamide, 4-amino-3-oxo-azepane-1-carboxylic-acid-benzylamide, 4-amino-1-benzyl-azepan-3-one, 4-amino-1-benzyl-piperidin-3-one, 4-amino-1-benzoyl-piperidin-3-one, 4-amino-1-benzoyl-pyrrolidin-3-one, 4-amino-1-benzyl-pyrrolidin-3-one, 4-amino-1-benzenesulfonyl-pyrrolidin-3-one, 4-amino-1-(5-methyl-hexyl)-pyrrolidin-3-one, 1-ethyl-2-oxo-3-(toluene-4-sulfonylamino)-butylamino, 1-ethyl-2-oxo-3-(4-phenoxy-benzenesulfonylamino)-propylamino, 1-ethyl-2-oxo-3-[4-(pyridin-3-yloxy)-benzenesulfonylamino]-propylamino, 3-(dibenzofuran-2-sulfonylamino)-1-ethyl-2-oxo-butylamino, 1-ethyl-3-[4-methyl-2-(4-methyl-pentanoylamino)-pentanoylamino]-2-oxo-propylamino, 5-amino-1-[(4-methoxy-phenylsulfamoyl)-methyl]-pentylamino, 5-benzyloxycarbonylamino-1-[(4-methoxy-phenylsulfamoyl)-methyl]-pentylamino, 1-[(4-methoxy-phenylsulfamoyl)-methyl]-3-phenyl-propylamino, 1-{[4-(1-hydroxy-ethyl)-phenylsulfamoyl]-methyl}-3-phenyl-propylamino, 1-[(4-acetyl-phenylsulfamoyl)-methyl]-3-phenyl-propylamino, 1-[(4-hydroxy-phenylsulfamoyl)-methyl]-3-phenyl-propylamino and 3-phenyl-1-[(2-phenylamino-ethylsulfamoyl)-methyl]-propylamino; and the N-oxide derivatives, prodrug derivatives, protected derivatives, individual isomers and mixtures of isomers thereof; and the pharmaceutically acceptable salts and solvates of such compounds and the N-oxide derivatives, prodrug derivatives, protected derivatives, individual isomers and mixtures of isomers thereof.

Reference to the preferred embodiments set forth above is meant to include all combinations of particular and preferred groups.

Particular compounds of the invention may be prepared by joining C* of one of the fragments (A1 to A72) shown in Table 1 to the nitrogen atom (*N) of one of the fragments (B1 to B80) shown in Table 2, and joining the methine carbon atom (CH*) of one of the fragments (B1 to B80) shown in Table 2 to the acyl carbon atom (C*) of one of the fragments (C1 to C37) depicted in Table 3.

TABLE 1

| A1 | 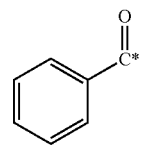 |
| A2 | 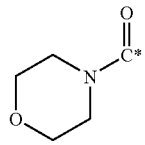 |
| A3 |  |
| A4 | 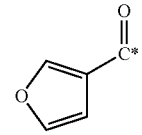 |
| A5 | 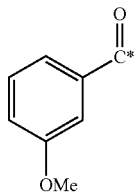 |
| A6 | 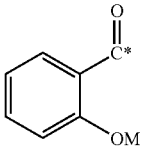 |
| A7 | 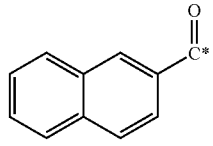 |
| A8 | 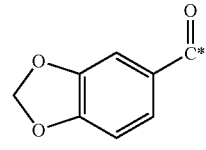 |
| A9 | 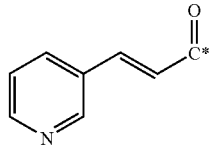 |
| A10 | 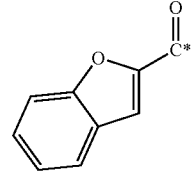 |

TABLE 1-continued
| | | | |
|---|---|---|---|
| A11 | 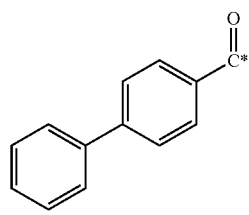 | A21 | 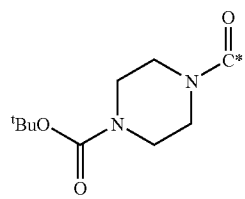 |
| A12 | 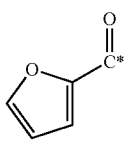 | A22 | 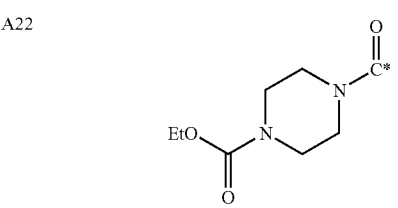 |
| A13 | 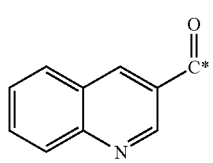 | A23 | 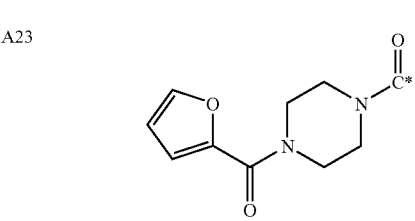 |
| A14 | 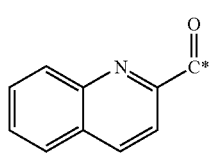 | A24 | 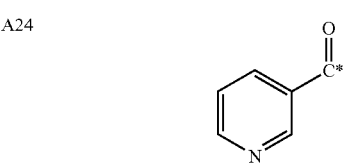 |
| A15 |  | A25 | 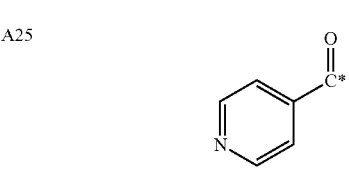 |
| A16 | 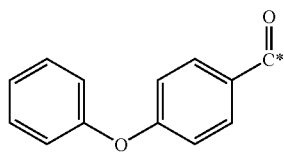 | A26 | 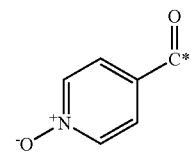 |
| A17 | 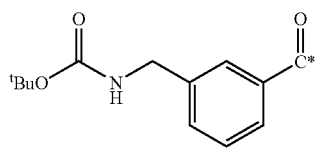 | A27 | 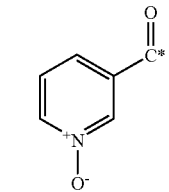 |
| A18 | 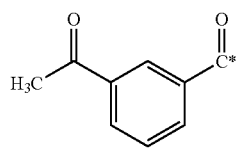 | A28 | 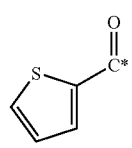 |
| A19 | 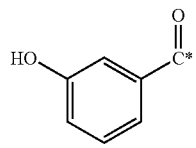 | | |
| A20 | 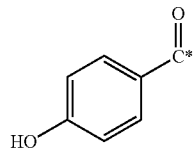 | | |

TABLE 1-continued

| | |
|---|---|
| A29 | thiophen-3-yl-C(=O)* |
| A30 | 4-benzoylphenyl-C(=O)* |
| A31 | 5-methylthiophen-2-yl-C(=O)* |
| A32 | 3-chlorothiophen-2-yl-C(=O)* |
| A33 | 3-bromothiophen-2-yl-C(=O)* |
| A34 | cyclopentyl-C(=O)* |
| A35 | benzo[b]thiophen-2-yl-C(=O)* |
| A36 | 3-chlorobenzo[b]thiophen-2-yl-C(=O)* |
| A37 | 5-methylthiophen-2-yl-S(=O)₂* |
| A38 | naphthalen-2-yl-S(=O)₂* |
| A39 | phenyl-S(=O)₂* |
| A40 | 4-(trifluoromethyl)phenyl-C(=O)* |
| A41 | 3-fluoro-4-methoxyphenyl-C(=O)* |
| A42 | 4-chlorophenyl-C(=O)* |
| A43 | 4-bromophenyl-C(=O)* |
| A44 | 4-methoxyphenyl-C(=O)* |
| A45 | 4-(trifluoromethoxy)phenyl-C(=O)* |
| A46 | 3,4-difluorophenyl-C(=O)* |
| A47 | 3,4-dimethoxyphenyl-C(=O)* |

TABLE 1-continued
| | |
|---|---|
| A48 | 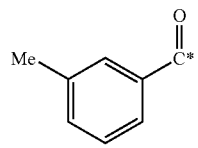 |
| A49 | 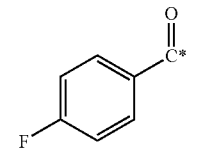 |
| A50 | (CH$_3$)$_2$CHCH$_2$—C*(=O) |
| A51 | (CH$_3$)$_2$CHCH$_2$O—C*(=O) |
| A52 | CH$_3$O—C*(=O) |
| A53 | CH$_2$=CHCH$_2$O—C*(=O) |
| A54 | (CH$_3$)$_2$CHO—C*(=O) |
| A55 | (CH$_3$)$_2$CHNH—C*(=O) |
| A56 | (CH$_3$)$_2$N—C*(=O) |
| A57 |  |
| A58 | 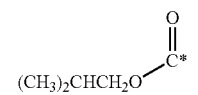 |
| A59 | 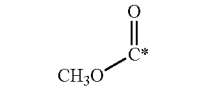 |
| A60 | 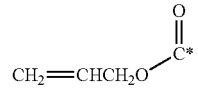 |
| A61 | 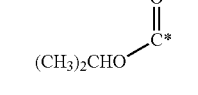 |
| A62 | 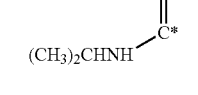 |
| A63 | 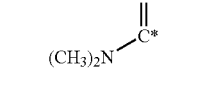 |
| A64 | 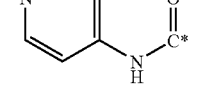 |
| A65 | 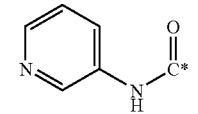 |
| A66 | 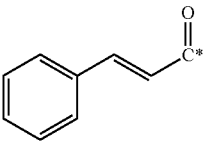 |
| A67 | 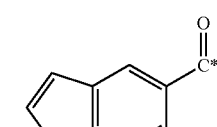 |
| A68 | 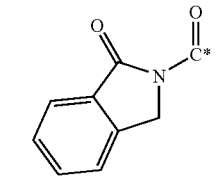 |

TABLE 1-continued
A69 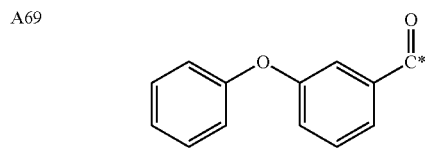
A70 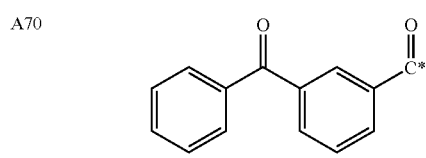
A71 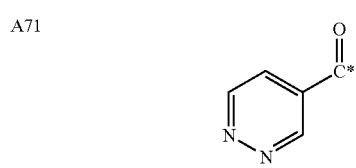
A72 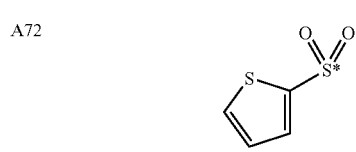
TABLE 2
B1 
B2 
B3 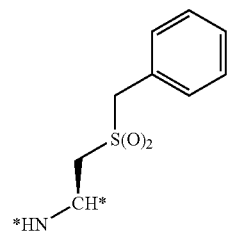
B4 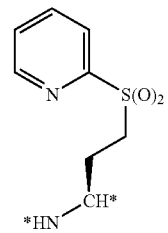
B5 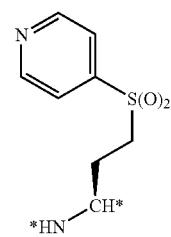
B6 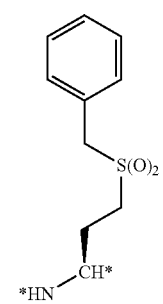
B7 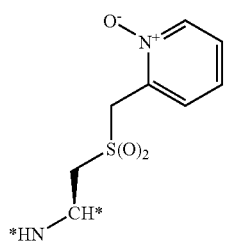
B8 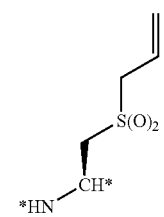
B9 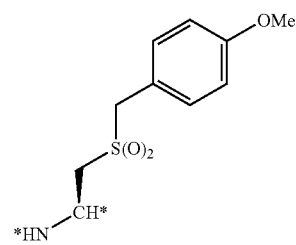

TABLE 2-continued

| | | |
|---|---|---|
| B10 | 4-methylbenzyl-CH2-S(O)2-CH2-NH* | |
| B11 | 4-chlorobenzyl-CH2-S(O)2-CH2-NH* | |
| B12 | 2-methylbenzyl-CH2-S(O)2-CH2-NH* | |
| B13 | 3,5-dimethylbenzyl-CH2-S(O)2-CH2-NH* | |
| B14 | 4-(trifluoromethyl)benzyl-CH2-S(O)2-CH2-NH* | |
| B15 | 4-(trifluoromethoxy)benzyl-CH2-S(O)2-CH2-NH* | |
| B16 | 2-bromobenzyl-CH2-S(O)2-CH2-NH* | |
| B17 | 2-naphthylmethyl-CH2-S(O)2-CH2-NH* | |
| B18 | 2-pyridylmethyl-CH2-S(O)2-CH2-NH* | |
| B19 | 4-pyridylmethyl-CH2-S(O)2-CH2-NH* | |
| B20 | 3-pyridylmethyl-CH2-S(O)2-CH2-NH* | |
| B21 | 3,4-dichlorobenzyl-CH2-S(O)2-CH2-NH* | |

TABLE 2-continued
B22 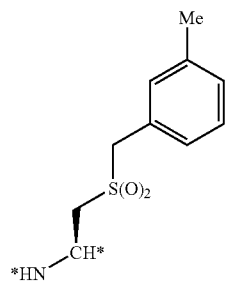
B23 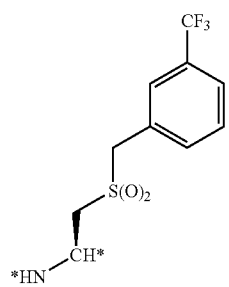
B24 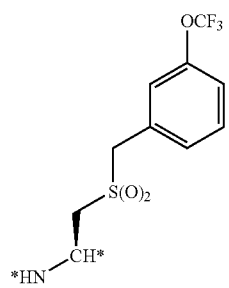
B25 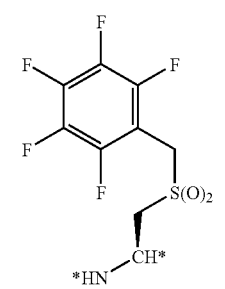
B26 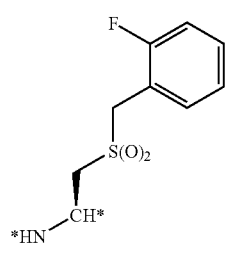
TABLE 2-continued
B27 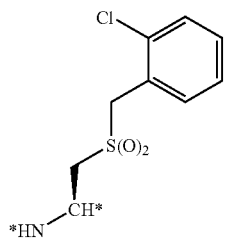
B28 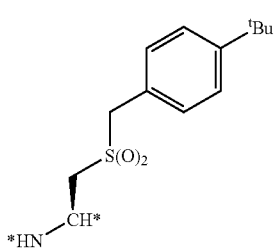
B29 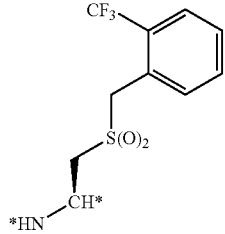
B30 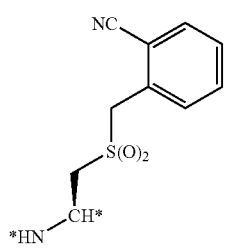
B31 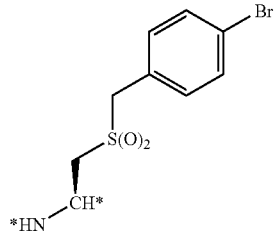
B32 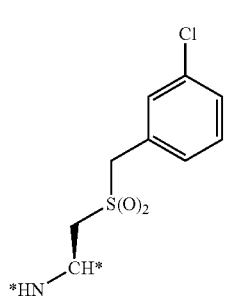

TABLE 2-continued

| | | |
|---|---|---|
| B33 | 3-chloro-2-fluorobenzyl-CH2-S(O)2-CH*-NH* | |
| B34 | 2-fluoro-3-methylbenzyl-CH2-S(O)2-CH*-NH* | |
| B35 | 3-fluorobenzyl-CH2-S(O)2-CH*-NH* | |
| B36 | 2,5-difluorobenzyl-CH2-S(O)2-CH*-NH* | |
| B37 | 2,6-difluorobenzyl-CH2-S(O)2-CH*-NH* | |
| B38 | 2,5-dichlorobenzyl-CH2-S(O)2-CH*-NH* | |
| B39 | 3-bromobenzyl-CH2-S(O)2-CH*-NH* | |
| B40 | 3-cyanobenzyl-CH2-S(O)2-CH*-NH* | |
| B41 | 4-cyanobenzyl-CH2-S(O)2-CH*-NH* | |
| B42 | 2-(trifluoromethoxy)benzyl-CH2-S(O)2-CH*-NH* | |
| B43 | 2,3-difluorobenzyl-CH2-S(O)2-CH*-NH* | |

TABLE 2-continued

| | |
|---|---|
| B44 | [2-phenylphenyl-CH2-S(O)2-CH*-NH*] |
| B45 | [2-Br,5-F-phenyl-CH2-S(O)2-CH*-NH*] |
| B46 | [4-F-phenyl-CH2-S(O)2-CH*-NH*] |
| B47 | [3,4-diF-phenyl-CH2-S(O)2-CH*-NH*] |
| B48 | [2,4-diF-phenyl-CH2-S(O)2-CH*-NH*] |
| B49 | [2,4,6-triF-phenyl-CH2-S(O)2-CH*-NH*] |
| B50 | [2,4,5-triF-phenyl-CH2-S(O)2-CH*-NH*] |
| B51 | [2,3,4-triF-phenyl-CH2-S(O)2-CH*-NH*] |
| B52 | [2-Cl,5-CF3-phenyl-CH2-S(O)2-CH*-NH*] |
| B53 | [2,4-bis(CF3)-phenyl-CH2-S(O)2-CH*-NH*] |
| B54 | [2,3,6-triF-phenyl-CH2-S(O)2-CH*-NH*] |
| B55 | [2-F,3-CF3-phenyl-CH2-S(O)2-CH*-NH*] |

TABLE 2-continued

| | | |
|---|---|---|
| B56 | 2-F, 4-CF3 benzyl-CH2-S(O)2-CH(*NH*)- | |
| B57 | 2-F, 6-CF3 benzyl-CH2-S(O)2-CH(*NH*)- | |
| B58 | 2,3,5-trifluoro benzyl-CH2-S(O)2-CH(*NH*)- | |
| B59 | 2-F, 5-CF3 benzyl-CH2-S(O)2-CH(*NH*)- | |
| B60 | 2-CF3, 4-F benzyl-CH2-S(O)2-CH(*NH*)- | |
| B61 | 3-CF3, 4-F benzyl-CH2-S(O)2-CH(*NH*)- | |
| B62 | 2-MeO benzyl-CH2-S(O)2-CH(*NH*)- | |
| B63 | 3,5-bis(CF3) benzyl-CH2-S(O)2-CH(*NH*)- | |
| B64 | 4-OCHF2 benzyl-CH2-S(O)2-CH(*NH*)- | |
| B65 | 3-OCHF2 benzyl-CH2-S(O)2-CH(*NH*)- | |
| B66 | 2,6-dichloro benzyl-CH2-S(O)2-CH(*NH*)- | |
| B67 | 4-CO2H benzyl-CH2-S(O)2-CH(*NH*)- | |

TABLE 2-continued

| | |
|---|---|
| B68 | [structure: 3,5-dimethylisoxazol-4-yl-CH2-S(O)2-CH2-NH*] |
| B69 | [structure: 5-chlorothiophen-2-yl-CH2-S(O)2-CH2-NH*] |
| B70 | [structure: 4-(F2CHO)-C6H4-S(O)2-CH2CH2-NH*] |
| B71 | [structure: 2-(OCHF2)-C6H4-S(O)2-CH2CH2-NH*] |
| B72 | [structure: 3-(OCHF2)-C6H4-S(O)2-CH2CH2-NH*] |
| B73 | [structure: 4-(F3CO)-C6H4-S(O)2-CH2CH2-NH*] |
| B74 | [structure: 2-(OCF3)-C6H4-S(O)2-CH2CH2-NH*] |
| B75 | [structure: 3-(OCF3)-C6H4-S(O)2-CH2CH2-NH*] |
| B76 | [structure: thiophen-2-yl-S(O)2-CH2CH2-NH*] |
| B77 | [structure: phenyl-S(O)2-CH2CH2-NH*] |
| B78 | [structure: isobutyl-S(O)2-CH2CH2-NH*] |
| B79 | [structure: cyclohexyl-CH2-S(O)2-CH2CH2-NH*] |

TABLE 2-continued
| B80 | 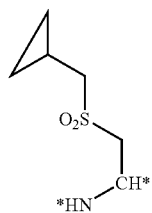 |
TABLE 3
| C1 | 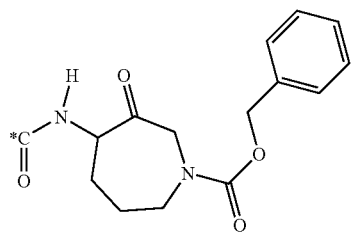 |
| C2 | 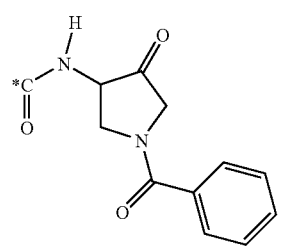 |
| C3 | 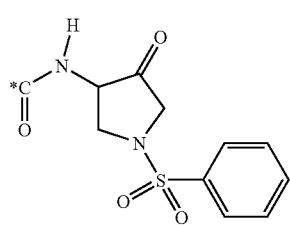 |
| C4 | 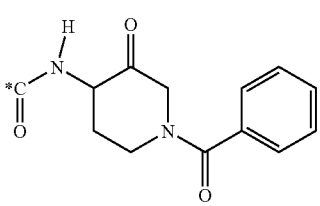 |
| C5 | 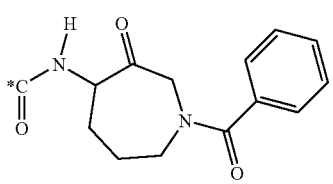 |
| C6 | 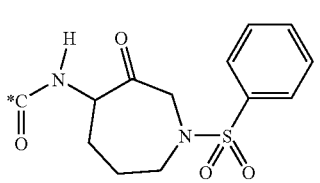 |
TABLE 3-continued
| C7 | 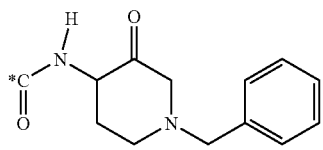 |
| C8 | 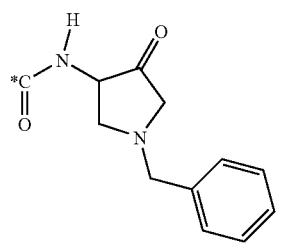 |
| C9 | 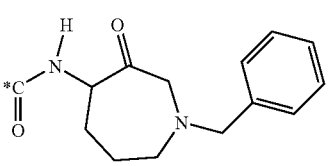 |
| C10 | 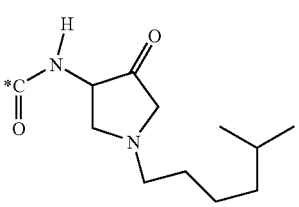 |
| C11 | 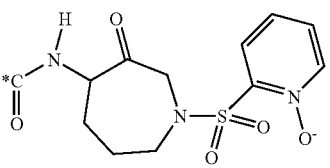 |
| C12 | 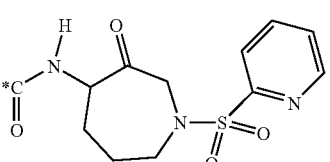 |
| C13 | 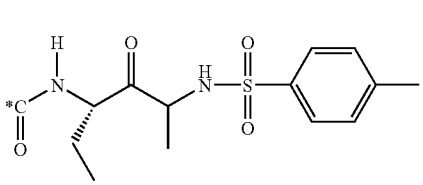 |
| C14 | 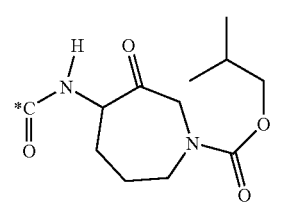 |

TABLE 3-continued
| | |
|---|---|
| C15 | 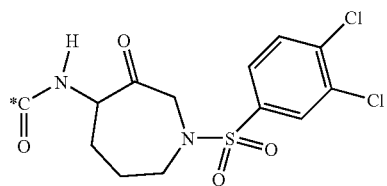 |
| C16 | 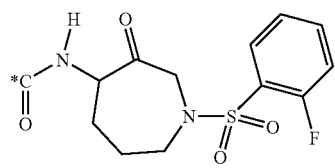 |
| C17 | 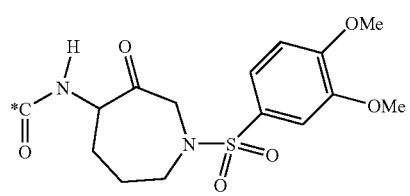 |
| C18 | 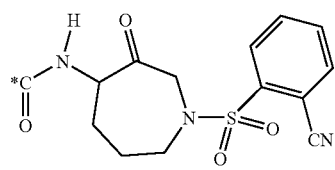 |
| C19 | 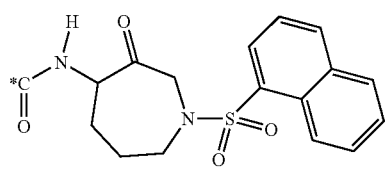 |
| C20 | 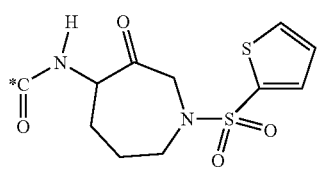 |
| C21 | 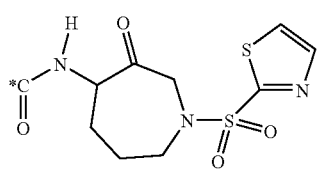 |
| C22 | 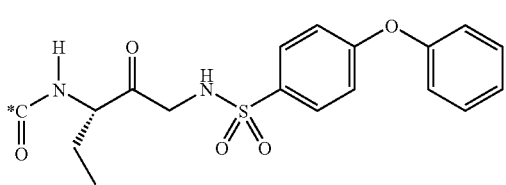 |
TABLE 3-continued
| | |
|---|---|
| C23 | 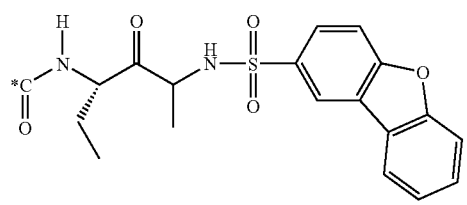 |
| C24 | 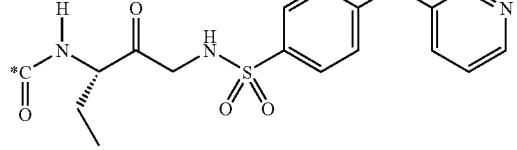 |
| C25 | 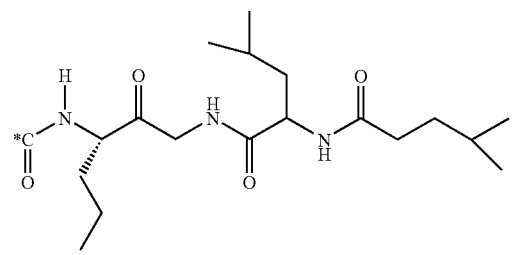 |
| C26 | 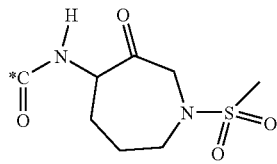 |
| C27 | 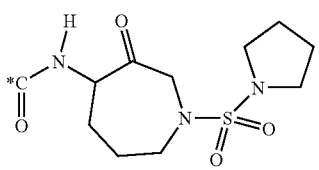 |
| C28 | 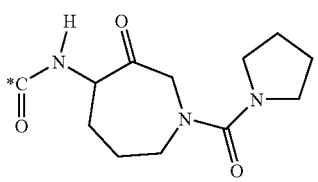 |
| C29 | 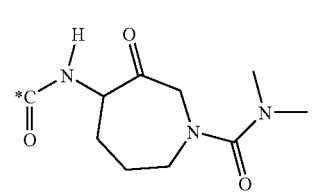 |
| C30 | 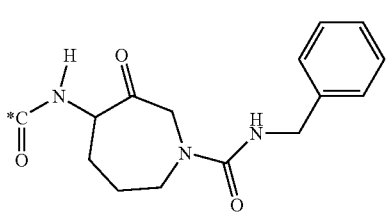 |

TABLE 3-continued

| | |
|---|---|
| C31 | 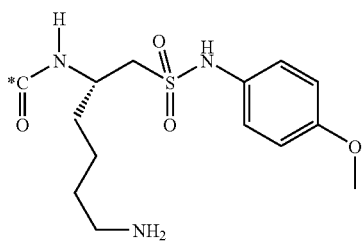 |
| C32 | 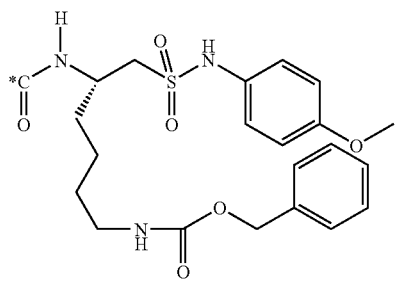 |
| C33 | 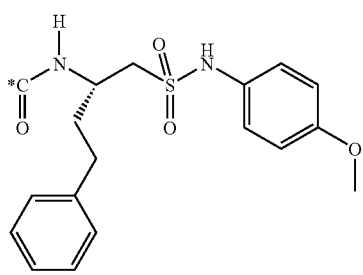 |
| C34 | 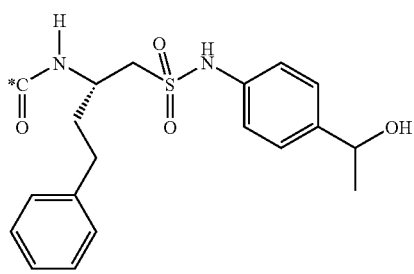 |
| C35 | 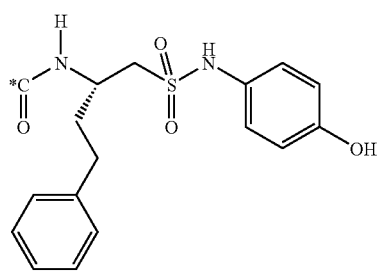 |
| C36 | 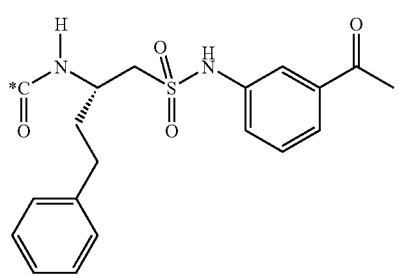 |

TABLE 3-continued

| | |
|---|---|
| C37 | 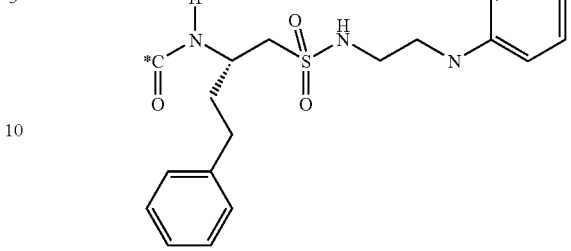 |

Pharmacology and Utility:

The compounds of the invention are selective inhibitors of cathepsin S and, as such, are useful for treating diseases in which cathepsin S activity contributes to the pathology and/or symptomatology of the disease. For example, the compounds of the invention are useful in treating autoimmune disorders, including, but not limited to, juvenile onset diabetes, multiple sclerosis, pemphigus vulgaris, Graves' disease, myasthenia gravis, systemic lupus erythemotasus, rheumatoid arthritis and Hashimoto's thyroiditis, allergic disorders, including, but not limited to, asthma, and allogeneic immune responses, including, but not limited to, organ transplants or tissue grafts.

Cathepsin S also is implicated in disorders involving excessive elastolysis, such as chronic obstructive pulmonary disease (e.g., emphysema), bronchiolitis, excessive airway elastolysis in asthma and bronchitis, pneumonities and cardiovascular disease such as plaque rupture and atheroma. Cathepsin S is implicated in fibril formation and, therefore, inhibitors of cathepsins S are of use in treatment of systemic amyloidosis.

The cysteine protease inhibitory activities of the compounds of the invention can be determined by methods known to those of ordinary skill in the art. Suitable in vitro assays for measuring protease activity and the inhibition thereof by test compounds are known. Typically, the assay measures protease induced hydrolysis of a peptide based substrate. Details of assays for measuring protease inhibitory activity are set forth in Examples 14–17, infra.

Administration and Pharmaceutical Compositions:

In general, compounds of Formula I will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. For example, therapeutically effective amounts of a compound of Formula I may range from about 1 micrograms per kilogram body weight (µg/kg) per day to about 1 milligram per kilogram body weight (mg/kg) per day, typically from about 10 µg/kg/day to about 0.1 mg/kg/day. Therefore, a therapeutically effective amount for a 80 kg human patient may range from about 100 µg/day to about 100 mg/day, typically from about 1 µg/day to about 10 mg/day. In general, one of ordinary skill in the art, acting in reliance upon personal knowledge and the disclosure of this Application, will be able to ascertain a therapeutically effective amount of a compound of Formula I for treating a given disease.

The compounds of Formula I can be administered as pharmaceutical compositions by one of the following routes: oral, systemic (e.g., transdermal, intranasal or by suppository) or parenteral (e.g., intramuscular, intravenous or subcutaneous). Compositions can take the form of tablets, pills, capsules, semisolids, powders, sustained release formulations, solutions, suspensions, elixirs, aerosols, or any other appropriate composition and are comprised of, in general, a compound of Formula I in combination with at least one pharmaceutically acceptable excipient. Acceptable excipients are non-toxic, aid administration, and do not adversely affect the therapeutic benefit of the active ingredient. Such excipient may be any solid, liquid, semisolid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from water, ethanol, glycerol, propylene glycol and various oils, including those of petroleum, animal, vegetable or synthetic origin (e.g., peanut oil, soybean oil, mineral oil, sesame oil, and the like). Preferred liquid carriers, particularly for injectable solutions, include water, saline, aqueous dextrose and glycols.

The amount of a compound of Formula I in the composition may vary widely depending upon the type of formulation, size of a unit dosage, kind of excipients and other factors known to those of skill in the art of pharmaceutical sciences. In general, a composition of a compound of Formula I for treating a given disease will comprise from 0.01% w to 10% w, preferably 0.3% w to 1% w, of active ingredient with theremainder being the excipient or excipients. Preferably the pharmaceutical composition is administered in a single unit dosage form for continuous treatment or in a single unit dosage form ad libitum when relief of symptoms is specifically required. Representative pharmaceutical formulations containing a compound of Formula I are described in Example 10, infra.

Chemistry:

Processes for Making Compounds of Formula I:

Compounds of the invention may be prepared by the application or adaptation of known methods, by which is meant methods used heretofore or described in the literature, for example those described by R. C. Larock in Comprehensive Organic Transformations, VCH publishers, 1989.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

Compounds of Formula I, in which $X^3$ is a compound of formula (a) (as defined in the Summary of the Invention), can be prepared by proceeding as in the following Reaction Scheme 1:

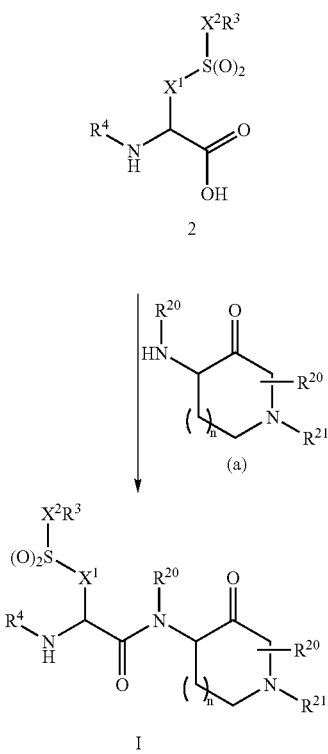

in which each $X^1$, $X^2$, $R^3$, $R^4$, $R^{20}$ and $R^{21}$ are as defined for Formula I in the Summary of the Invention.

Compounds of Formula I can be prepared by condensing an acid of Formula 2 with an amino compound of formula (a). The condensation reaction can be effected with an appropriate coupling agent (e.g., benzotriazol-1-yloxytrispyrrolidinophosphonium hexafluorophosphate (PyBOP®), 1-(3-dimethylaminopropyl)-3-ethylcarbodiimide hydrochloride (EDCI), O-benzotriazol-1-yl-N,N,N',N'-tetramethyluronium hexafluorophosphate (HBTU), 1,3-dicyclohexylcarbodiimide (DCC), or the like) and optionally an appropriate catalyst (e.g., 1-hydroxybenzotriazole (HOBt), 1-hydroxy-7-azabenzotriazole (HOAt), O-(7-azabenzotriazol-1-yl)-1,1,3,3, tetra-methyluroniumhexafluorophosphate (HATU), or the like) and non-nucleophilic base (e.g., triethylamine, N-methylmorpholine, and the like, or any suitable combination thereof) at ambient temperature and requires 5 to 10 hours to complete.

An oxidation step, if required, can be carried out with an oxidizing agent (e.g., Oxone®, metachloroperbenzoic acid or the like) in a suitable solvent (e.g., methanol, water, or the like, or any suitable combination thereof) at ambient temperature and requires 16 to 24 hours to complete. Detailed descriptions for the synthesis of a compound of Formula I by the processes in Reaction Scheme 1 are set forth in the Examples 1 to 11, infra.

Compounds of Formula I, where $X^3$ is a compound of formula (b) (as defined in the Summary of the Invention), can be prepared by proceeding as in the following Reaction Scheme 2:

Reaction Scheme 2

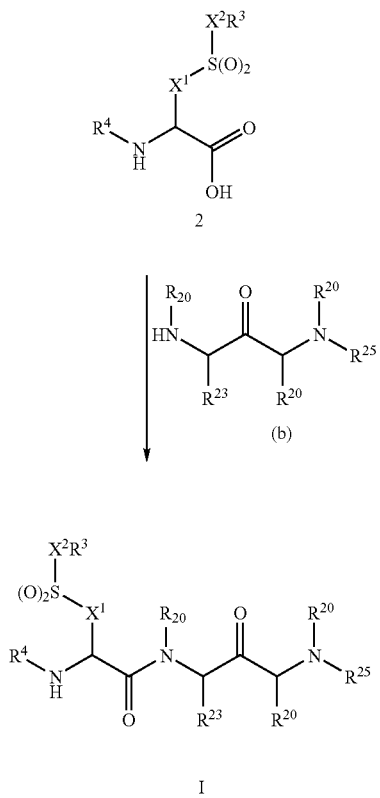

in which each $X^1$, $X^2$, $R^3$, $R^4$, $R^{20}$, $R^{23}$ and $R^{25}$ are as defined for Formula I in the Summary of the Invention.

Compounds of Formula I can be prepared by condensing an acid of Formula 2 with an amino compound of formula (b). The condensation reaction can be effected with an appropriate coupling agent (e.g., benzotriazol-1-yloxy-trispyrrolidinophosphonium hexafluorophosphate (Py-BOP®), 1-(3-dimethylaminopropyl)-3-ethylcarbodiimide hydrochloride (EDCI), O-benzotriazol-1-yl-N,N,N',N'-tetramethyluronium hexafluorophosphate (HBTU), 1,3-dicyclohexylcarbodiimide (DCC), or the like) and optionally an appropriate catalyst (e.g., 1-hydroxybenzotriazole (HOBt), 1-hydroxy-7-azabenzotriazole (HOAt), O-(7-azabenzotriazol-1-yl)-1,1,3,3, tetra-methyluroniumhexafluorophosphate (HATU), or the like) and non-nucleophilic base (e.g., triethylamine, N-methylmorpholine, and the like, or any suitable combination thereof) at ambient temperature and requires 5 to 10 hours to complete.

An oxidation step, if required, can be carried out with an oxidizing agent (e.g., Oxone®, metachloroperbenzoic acid or the like) in a suitable solvent (e.g., methanol, water, or the like, or any suitable combination thereof) at ambient temperature and requires 16 to 24 hours to complete.

Compounds of Formula 1 in which $X^3$ is a compound of formula (c) (as defined in the Summary of the Invention), can be prepared by reacting a compound of Formula 2 with a compound of Formula (c) according to the following reaction scheme:

Reaction Scheme 3

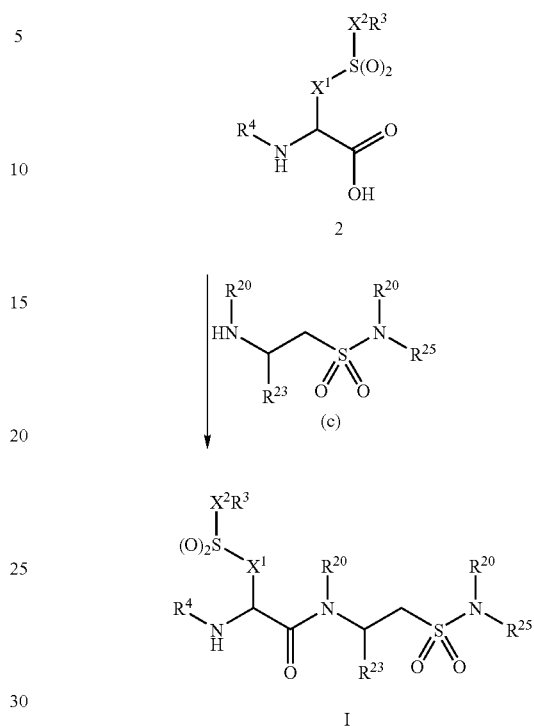

in which each $X^1$, $X^2$, $R^3$, $R^4$, $R^{20}$, $R^{23}$ and $R^{25}$ are as defined for Formula I in the Summary of the Invention.

Additional Processes for Preparing Compounds of Formula I:

A compound of Formula I can be prepared as a pharmaceutically acceptable acid addition salt by reacting the free base form of the compound with a pharmaceutically acceptable inorganic or organic acid. Alternatively, a pharmaceutically acceptable base addition salt of a compound of Formula I can be prepared by reacting the free acid form of the compound with a pharmaceutically acceptable inorganic or organic base. Inorganic and organic acids and bases suitable for the preparation of the pharmaceutically acceptable salts of compounds of Formula I are set forth in the definitions section of this Application. Alternatively, the salt forms of the compounds of Formula I can be prepared using salts of the starting materials or intermediates.

The free acid or free base forms of the compounds of Formula I can be prepared from the corresponding base addition salt or acid addition salt form. For example, a compound of Formula I in an acid addition salt form can be converted to the corresponding free base by treating with a suitable base (e.g., ammonium hydroxide solution, sodium hydroxide, and the like). A compound of Formula I in a base addition salt form can be converted to the corresponding free acid by treating with a suitable acid (e.g., hydrochloric acid, etc).

The N-oxides of compounds of Formula I can be prepared by methods known to those of ordinary skill in the art. For example, N-oxides can be prepared by treating an unoxidized form of the compound of Formula I with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds of Formula I can be prepared from the N-oxide of an appropriate starting material.

Compounds of Formula I in unoxidized form can be prepared from N-oxides of compounds of Formula I by treating with a reducing agent (e.g., sulfur, sulfur dioxide, triphenyl phosphine, lithium borohydride, sodium borohydride, phosphorus trichloride, tribromide, or the like) in an suitable inert organic solvent (e.g., acetonitrile, ethanol, aqueous dioxane, or the like) at 0 to 80° C.

Prodrug derivatives of the compounds of Formula I can be prepared by methods known to those of ordinary skill in the art (e.g., for further details see Saulnier et al. (1994), *Bioorganic and Medicinal Chemistry Letters*, Vol. 4, p. 1985). For example, appropriate prodrugs can be prepared by reacting a non-derivatized compound of Formula I with a suitable carbamylating agent (e.g., 1,1-acyloxyalkylcarbonochloridate, para-nitrophenyl carbonate, or the like).

Protected derivatives of the compounds of Formula I can be made by means known to those of ordinary skill in the art. A detailed description of the techniques applicable to the creation of protecting groups and their removal can be found in T. W. Greene, *Protecting Groups in Organic Synthesis*, 3$^{rd}$ edition, John Wiley & Sons, Inc. 1999. Compounds of the present invention may be conveniently prepared, or formed during the process of the invention, as solvates (e.g. hydrates). Hydrates of compounds of the present invention may be conveniently prepared by recrystallisation from an aqueous/organic solvent mixture, using organic solvents such as dioxin, tetrahydrofuran or methanol. Compounds of Formula I can be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diastereomeric derivatives of compounds of Formula I, dissociable complexes are preferred (e.g., crystalline diastereoisomeric salts). Diastereomers have distinct physical properties (e.g., melting points, boiling points, solubilities, reactivity, etc.) and can be readily separated by taking advantage of these dissimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet, Samuel H. Wilen, Enantiomers, Racemates and Resolutions, John Wiley & Sons, Inc. (1981).

In summary, the compounds of Formula I are made by a process which comprises:

(A) reacting a compound of Formula 2:

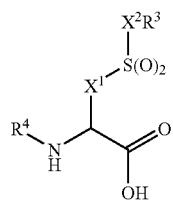

2 with a compound of the formula (a):

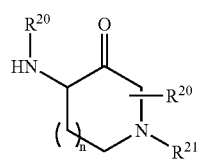

(a)

in which $X^1$, $X^2$, $R^3$, $R^4$, $R^{20}$ and $R^{21}$ are as defined in the Summary of the Invention for Formula I; or (B) reacting a compound of Formula 2 with a compound of the formula (b):

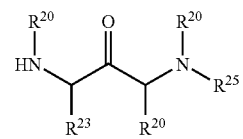

(b)

in which $R^{20}$, $R^{23}$ and $R^{25}$ are as defined in the Summary of the Invention for Formula I; or (C) reacting a compound of Formula 2 with a compound of the formula (c):

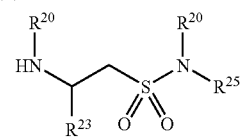

(c)

in which $R^{20}$, $R^{23}$ and $R^{25}$ are as defined in the Summary of the Invention for Formula I; and (D) optionally converting a compound of Formula I into a pharmaceutically acceptable salt;
(E) optionally converting a salt form of a compound of Formula I to non-salt form;
(F) optionally converting an unoxidized form of a compound of Formula I into a pharmaceutically acceptable N-oxide;
(G) optionally converting an N-oxide form of a compound of Formula I its unoxidized form;
(H) optionally resolving an individual isomer of a compound of Formula I from a mixture of isomers;
(I) optionally converting a non-derivatized compound of Formula I into a pharmaceutically prodrug derivative; and
(J) optionally converting a prodrug derivative of a compound of Formula I to its non-derivatized form.

EXAMPLES

The present invention is further exemplified, but not limited by, the following examples that illustrate the preparation of compounds of Formula I (Examples) and intermediates (References) according to the invention.

REFERENCE 1

3-amino-4-hydroxy-pyrrolidine-1-carboxylic acid tert-butyl ester

6-Oxa-3-aza-bicyclo[3.1.0]hexane-3-carboxylic acid tert-butyl ester (12.1 g, 65.3 mmol) was dissolved in a 8:1 methanol/water mixture (108 mL). Ammonium chloride (15 g) and sodium azide (21.4 g, 329 mmol) was added and the mixture was heated at 60° C. overnight. After dilution with ether (500 mL), the mixture was washed with saturated aqueous NaHCO$_3$ (200 mL) and brine (200 mL), dried with MgSO$_4$ and evaporated under vacuum. The crude product was dissolved in methanol (200 mL). 10% Palladium on activated carbon (1.5 g) was added and the mixture was stirred at ambient temperature under a hydrogen atmosphere until TLC analysis showed the disappearance of the starting material. The mixture was filtered through a pad of Celite and evaporated to dryness under vacuum. The product was purified by flash chromatography on silica gel. Eluent: 5% methanol in ethyl acetate to 20% methanol, 3% triethylamine in ethyl acetate. Yield: 4.3 g 3-amino-4-hydroxy-pyrrolidine-1-carboxylic acid tert-butyl ester as yellowish solid.

REFERENCE 2

4-Amino-3-hydroxy-azepane-1-carboxylic acid benzyl ester

Sodium hydride (60% in mineral oil, 10 g, 250 mmol) was suspended in dry DMF. Allyl-carbamic acid benzyl ester (19.1 g, 100 mmol) was added drop wise at ambient temperature. After stirring for 5 minutes, 5-bromo-1-pentene (25 g, 168 mmol) was added drop wise. Stirring was continued at 50° C. for 1 hour. The reaction was quenched with water and then partitioned between diethyl ether and water. The ether layer was washed with water and brine, dried with MgSO$_4$ and evaporated under vacuum. Flash chromatography (ethyl acetate/hexane 1:9) gave allyl-pent-4-enyl-carbamic acid benzyl ester (15.5 g).

Allyl-pent-4-enyl-carbamic acid benzyl ester (15.5 g, 59.8 mmol) was dissolved in dichloromethane and bis(tricyclohexylphosphine)benzylidene ruthenium(IV) dichloride (1 g) was added. The mixture was refluxed under a nitrogen atmosphere until TLC analysis showed complete reaction. The solvent was evaporated under vacuum and the residue was purified by flash chromatography (ethyl acetate/hexane 1:9) to give 2,3,4,7-Tetrahydro-azepine-1-carboxylic acid benzyl ester (7.8 g).

To a solution of 2,3,4,7-tetrahydro-azepine-1-carboxylic acid benzyl ester (4.5 g, 19.45 mmol) in dichloromethane (50 mL) was added m-chloroperbenzoic acid (60 mmol). The mixture was stirred at ambient temperature for 16 hours. Saturated aqueous K$_2$CO$_3$ solution was added and the mixture was extracted with dichloromethane. The combined organic layers were washed with saturated aqueous NaHCO$_3$ and brine, dried with MgSO$_4$ and evaporated under vacuum. The crude epoxide was dissolved in an 8:1 methanol/water mixture (100 mL). Ammonium chloride (3.2 g, 60 mmol) and sodium azide (3.9 g, 60 mmol) were added and the mixture was heated at 60° C. for 48 hours. Most of the solvent was removed under vacuum. The residue was extracted with ethyl acetate. The combined organic layers were washed with saturated aqueous NaHCO$_3$ (200 mL) and brine (200 mL), dried with MgSO$_4$ and evaporated under vacuum. Flash chromatography of the residue (hexane/ethyl acetate 3:1) gave 4-azido-3-hydroxy-azepane-1-carboxylic acid benzyl ester (3.3 g).

To a solution of 4-azido-3-hydroxy-azepane-1-carboxylic acid benzyl ester (3.3 g, 11.37 mmol) in methanol (50 mL) was added triethylamine (5 mL) and 1,3-propanedithiol (3.42 mL, 35 mmol). The mixture was stirred at ambient temperature until TLC analysis showed complete consumption of the starting material. A white precipitate was removed by filtration and the filtrate was evaporated to dryness. The residue was triturated with a 1:1 hexane/diethyl ether mixture to remove excess dithiol and dried under vacuum to yield 4-amino-3-hydroxy-azepane-1-carboxylic acid benzyl ester.

REFERENCE 3

2S-Amino-N-(4-methoxyphenyl)-4-phenylbutane-1-sulfonamide hydrochloride

A solution comprised of crude tert-butyl 1-(4-methoxyphenylsulfamoylmethyl)-3-phenylpropylcarbamate (1.92 g, 4.42 mmol), prepared as in Reference Example 2, in DCM (10 mL) was treated with a 4M solution of hydrogen chloride in dioxane (11 mL). The mixture was stirred for 16 hours at room temperature and diluted with diethyl ether. A resulting precipitate was collected by filtration, washed several times with diethyl ether and hexane and pumped dry to provide 2S-amino-N-4-methoxyphenyl-4-phenylbutane-1-sulfonamide hydrochloride with quantitative mass recovery. $^1$H NMR (DMSO): 2.05 (2H, m); 2.6–2.7 (2H, m); 3.4 (3H, m*); 3.72 (3H, s); 6.9 (2H, d, J=7 Hz); 7.25 (5H, m); 7.3 (2H, d, J=7 Hz); 8.5 (br. s); 10.0 (1H, s).

Example 1

Morpholine-4-carboxylic acid [1-(1-benzoyl-4-oxo-pyrrolidin-3-ylcarbamoyl)-2-phenylmethanesulfonyl-ethyl]-amide (Compound 1)

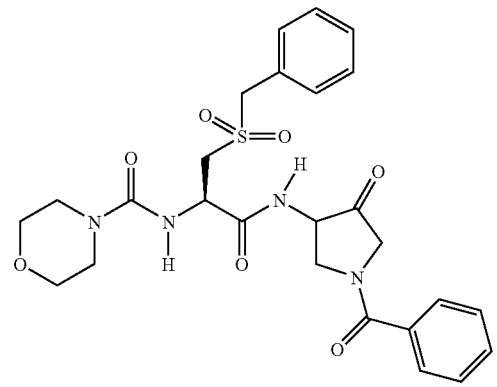

2-[(Morpholine-4-carbonyl)-amino]-3-phenylmethanesulfonyl-propionic acid (1 g, 2.8 mmol), 3-amino-4-hydroxy-pyrrolidine-1-carboxylic acid tert-butyl ester (700 mg, 3.46 mmol) prepared as in Reference 1, EDC (1.5 g, 7.8 mmol), and HOBt (1.5 g, 9.6 mmol) were combined. Dichloromethane (10 mL) was added and then 4-methylmorpholine (1.5 mL). The mixture was stirred at ambient temperature for 2 hours. After dilution with ethyl acetate (200 mL) the solution was washed with saturated aqueous NaHCO$_3$ (100 mL) and brine (100 mL), dried with MgSO$_4$ and evaporated under vacuum. 3-Hydroxy-4-{2-[(morpholine-4-carbonyl)-amino]-3-phenylmethanesulfonyl-propionylamino}-pyrrolidine-1-carboxylic acid tert-butyl ester (1.05 g, 1.94 mmol) was obtained as yellowish foam and was dissolved in dichloromethane (6 mL). Trifluoroacetic acid (6 mL) was added and the mixture was stirred at ambient temperature for 1 hour. Evaporation under vacuum gave crude morpholine-4-carboxylic acid [1-(4-hydroxy-pyrrolidin-3-ylcarbamoyl)-2-phenylmethanesulfonyl-ethyl]-amide as TFA salt, which was used without further purification.

Morpholine-4-carboxylic acid [1-(4-hydroxy-pyrrolidin-3-ylcarbamoyl)-2-phenylmethanesulfonyl-ethyl]-amide TFA salt (215 mg, 0.39 mmol) was dissolved in 1,4-dioxane (20 mL). Saturated aqueous NaHCO$_3$ solution (10 mL) was added followed by benzoyl chloride (0.2 mL, 1.72 mmol). The mixture was stirred at ambient temperature for 1 hour and then extracted with ethyl acetate. The combined organic layers were washed with saturated aqueous NaHCO$_3$ and brine, dried with MgSO$_4$ and evaporated under vacuum. The residue was purified by flash chromatography on silica gel (Eluent: 5% methanol in ethyl acetate to 20% methanol in ethyl acetate) to yield morpholine-4-carboxylic acid [1-(1-benzoyl-4-hydroxy-pyrrolidin-3-ylcarbamoyl)-2-phenyl-methane-sulfonyl-ethyl]-amide (92mg).

Morpholine4-carboxylic acid [1-(1-benzoyl-4-hydroxy-pyrrolidin-3-ylcarbamoyl)-2-phenylmethanesulfonyl-ethyl]-amide (92 mg, 0.169 mmol) was dissolved in DMSO (5 mL). Triethylamine (0.5 mL) and then SO$_3$ pyridine complex (150 mg) were added and the mixture was stirred at ambient temperature for 3 hours. After dilution with ethyl acetate (100 mL), the solution was washed with water (50 mL) and brine, dried with MgSO$_4$ and evaporated under vacuum. The residue was purified by flash chromatography on silica gel (Eluent: 5% methanol in ethyl acetate) to yield mormholine-4-carboxylic acid [1-(1-benzoyl-4-oxo-pyrrolidin-3-ylcarbamoyl)-2-phenylmethanesulfonyl-ethyl]-amide as a mixture of diastereomers (Yellowish solid; 38 mg); $^1$H NMR: (DMSO) 8.50–8.35 (m, 1H), 7.55–7.34 (m, 10H), 7.16–6.95 (m, 1H), 4.80–4.65 (m, 1H), 4.54–4.22 (m, 3H), 3.98–3.25 (m, 14H); MS: (M+H)$^+$ 543.

Example 2

Morpholine-4-carboxylic acid [1-(1-benzenesulfonyl-4-oxo-pyrrolidin-3-ylcarbamoyl) 2-phenyl-methanesulfonyl-ethyl]-amide (Compound 2)

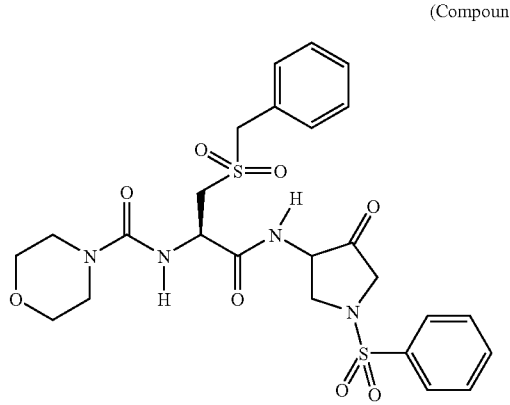

Morpholine-4-carboxylic acid [1-(1-benzenesulfonyl-4-oxo-pyrrolidin-3-ylcarbamoyl)2-phenylmethanesulfonyl-ethyl]-amide was prepared following the procedure detailed in Example 1, substituting benzenesulfonyl chloride for benzoyl chloride; $^1$H NMR: (DMSO) [8.35 (d, J=7.4 Hz), 8.28 (d, J=7.6 Hz), 1H], 7.87–7.62 (m, 5H), 7.41 7.32 (m, 5H), 7.06–6.98 (m, 1H), 4.72–4.60 (m, 1H), 4.45 (s, 2H), 4.42–4.23 (m, 1H), 3.92–3.79 (m, 2H), 3.55–3.20 (m, 11H), 3.06–2.97 (m, 1H). MS: (M+H)$^+$ 579.

Example 3

4-{2-[(Morpholine-4-carbonyl)-amino]-3-phenyl-methanesulfonyl-propionylamino}-3-oxo-azepane-1-carboxylic acid benzyl ester (Compound 3)

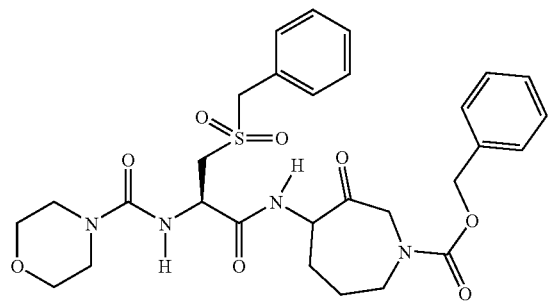

Crude 4-amino-3-hydroxy-azepane-1-carboxylic acid benzyl ester (150 mg, 0.57 mmol) prepared as in Reference 2, 2-[(morpholine-4-carbonyl)-amino]-3-phenylmethanesulfonyl-propionic acid (400 mg, 1.12 mmol), EDC (400 mg, 2.1 mmol), and HOBt (400 mg, 2.5 mmol) were combined. Dichloromethane (10 mL) was added followed by 4-methylmorpholine (0.5 mL). The mixture was stirred at ambient temperature for 2 hours. After dilution with ethyl acetate (100 mL) the solution was washed with 1N HCl, saturated aqueous NaHCO$_3$ and brine, dried with MgSO$_4$ and evaporated under vacuum. The residue was purified by flash chromatography (ethyl acetate/methanol 9: 1) to yield 3-hydroxy-4-{2-[(morpholine-4-carbonyl)-amino]-3-phenylmethanesulfonyl-propionyl-amino}-azepane-1-carboxylic acid benzyl ester (320 mg).

3-Hydroxy-4-{2-[(morpholine-4-carbonyl)-amino]-3-phenylmethanesulfonyl-propionylamino}-azepane-1-carboxylic acid benzyl ester (100 mg, 0.167 mmol) was dissolved in DMSO (5 mL). Triethylamine (0.3 mL) and then SO$_3$ pyridine complex (150 mg) were added and the mixture was stirred at ambient temperature for 3 hours. After dilution with ethyl acetate (100 mL), the solution was washed with water (50 mL) and brine, dried with MgSO$_4$ and evaporated under vacuum. The residue was purified by flash chromatography on silica gel (Eluent: 5% methanol in ethyl acetate) to yield 4-{2-[(morpholine-4-carbonyl)-amino]-3-phenyl-methanesulfonyl-propionylamino}-3-oxo-azepane-1-carboxylic acid benzyl ester (75 mg); $^1$H NMR: (DMSO) 8.23–8.08 (m, 1H), 7.40–7.29 (m, 10H), 7.06–6.98 (m, 1H), 5.20–5.09 (m, 2H), 4.79–4.65 (m, 1), 4.52–4.31 (m, 3H), 4.02–3.80 (m, 2H), 3.62–3.23 (m, 11H), 3.00–2.78 (m, 1H), 1.88–1.55 (m, 4H); MS: (M+H)$^+$ 601.

Example 4

Morpholine-4-carboxylic acid [1-(3-benzenesulfonylamino-2-oxo-propylcarbamoyl)-2-phenyl-methanesulfonyl-ethyl]-amide (Compound 4)

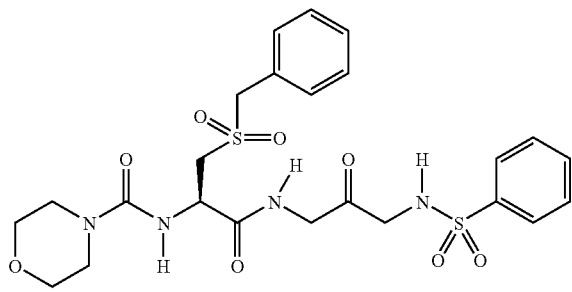

N-(3-Amino-2-hydroxy-propyl)-benzenesulfonamide TFA salt was prepared as outlined in Renee L. DesJarlais et al. *J. Am. Chem. Soc.* 1998, 120, 9114–9115.

2-[(Morpholine-4-carbonyl)-amino]-3-phenylmethanesulfonyl-propionic acid (50 mg, 0.14 mmol), N-(3-amino-2-hydroxy-propyl)-benzenesulfonamide TFA salt (60 mg, 0.17 mmol), EDC (100 mg, 0.52 mmol), and HOBt (100 mg, 0.64 mmol) were combined. DMF (3 mL) was added and then 4-methylmorpholine (0.3 mL). The mixture was stirred at ambient temperature for 3 hours. After dilution with ethyl acetate (100 mL) the solution was washed with 1N HCl, saturated aqueous NaHCO$_3$ and brine, dried with MgSO$_4$ and evaporated under vacuum. The residue was dissolved in acetone (5 mL). Jones reagent was added until the orange color persisted. The mixture was stirred for 2 hours, quenched with isopropanol, and diluted with ethyl acetate (100 mL). The solution was washed with water, saturated aqueous NaHCO$_3$ and brine, dried with MgSO$_4$ and evaporated under vacuum. The crude product was recrystallized from ethyl acetate/diethyl ether to give morpholine-4-carboxylic acid [1-(3-benzenesulfonylamino-2-oxo-propylcarbamoyl)-2-phenylmethanesulfonyl-ethyl]-amide as white solid (19 mg); $^1$H NMR: (DMSO) 8.17 (t, J=5.7 Hz, 1H), 7.93 (t, J=5.9 Hz, 1H), 7.76–7.48 (m, 5H), 7.36–7.29 (m, 5H), 7.05 (d, J=8.1 Hz, 1H), 4.68–4.59 (m, 1H), 4.45 (s, 2H), 3.89 (d, J=5.7 Hz, 2H), 3.79–3.75 (m, 2H), 3.56–3.22 (m, 10H); MS: (M+H)$^+$ 567.

Example 5

N-{1S-[1S-(4-Methoxyphenylsulfamoylmethyl)-3-phenylpropylcarbamoyl]2-benzylsulfonylethyl}-morpholine-4-carboxamide (Compound 7)

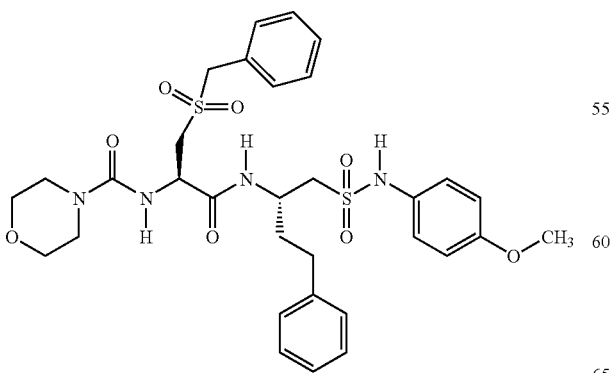

A mixture comprised of 2S-morpholin-4-ylcarbonylamino-3-benzylsulfonyl-propionic acid (0.194 g, 0.599 mmol), 2S-amino-N-(4-methoxyphenyl)-4-phenylbutane-1-sulfonamide hydrochloride (0.222 g, 0.599 mmol), prepared as in Reference 3, and HATU (0.228 g, 0.599 mmol) in DMF (5 mL) was treated with 4-methylmorpholine (0.198 g, 1.80 mmol). The mixture was stirred at room temperature for approximately 12 hours and then partitioned among a 4:1:2:3 mixture (100 mL total) of ethyl acetate, THF, water, and brine, respectively. The organic phase was separated and washed with saturated aqueous sodium bicarbonate (30 mL), brine (30 mL), dried (NgSO$_4$), filtered and concentrated. The residue was triturated with of 5:1 ether/ethyl acetate (100 mL), collected by filtration, washed with ether (30 mL), hexane (30 mL), and pumped dry to provide N-{1S-[1S-(4-methoxyphenylsulfamoylmethyl)-3-phenylpropylcarbamoyl]-2-benzylsulfonylethyl}-morpholine-4-carboxamide.

TLC R$_f$ (ethyl acetate): 0.65; $^1$H NMR (DMSO): 1.74 (1H, m); 1.92 (1H, m); 2.39–2.61 (2H, m); 3.1–3.35 (2H, 2xdd*); 3.34 (4H, m); 3.42–3.65 (6H, m*); 3.72 (3H, s); 4.24 (1H, m); 4.51 (2H, s); 4.61 (1H, m); 6.88 (2H, d, J=9 Hz); 7.1–7.34 (8H, m); 7.4 (5H, s); 8.12 (1H, d, J=8.7 Hz); MS (M+1): 673.

Proceeding as in Example 5 the Following Compounds of Formula I Were Prepared:

N-{1S-[5-amino-1S-(4-methoxyphenylsulfamoyl-methyl)pentylcarbamoyl}-2-benzylsulfonylethyl-morpholine-4-carboxamide hydrobromide (Compound 5); $^1$H NMR (DMSO): 1.15–1.73 (6H, m*); 2.71 (2H, m); 3.05–3.25 (2H, 2xdd); 3.37 (4H, m); 3.45–3.6 (6H, m*); 3.72 (3H, s); 4.21 (1H, m); 4.49 (2H, dd); 4.5 (1H, m*); 6.89 (2H, d, J=8.9 Hz); 7.09 (1H, m*); 7.15 (2H, d, J=8.9 Hz); 7.39 (5H, s); 7.73 (3H, br.s); 8.03 (1H, d, J=8.6 Hz); 9.47 (1H, s); MS (M+1): 640, free base); and Benzyl6-(4-methoxyphenylsulfamoyl)-5S-(2S-morpholin-4-ylcarbonylamino-3-benzylsulfonyl-propionylamino)hexylcarbamate (Compound 6); TLC R$_f$ (ethyl acetate): 0.3; $^1$H NMR (DMSO): 1.1–1.65 (6H, m); 2.94 (2H, q, J=6 Hz); 3.05–3.22 (2H, 2xdd); 3.34 (4H, m*); 3.35–3.59 (2H, m*); 3.53 (4H, br s); 3.71 (3H, s); 4.19 (1H, m*); 4.53 (2H, dd, J=15 Hz); 4.57 (1H, m*); 5.00 (2H, s); 6.89 (2H, d, J=8.4 Hz); 7.05 (1H, d, J=8 Hz); 7.15 (2H, d, J=8.4 Hz); 7.24 (1H, t); 7.3–7.45 (10H, 2xs); 7.99 (1H, J=8 Hz); MS (M+): 774.

Example 6

Morpholine-4-carboxylic acid [(R)-1-(6-oxo-cyclohex-1-enylcarbamoyl)-2-phenylmethanesulfonyl-ethyl]-amide (Compound 8)

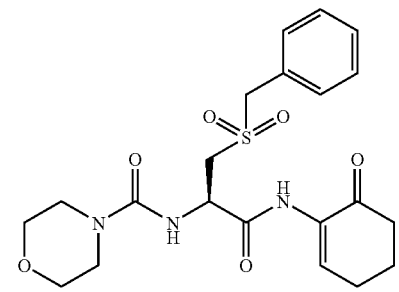

A solution of 2-amino-cyclohexane-1,3-diol (0.55 g) in dimethylformamide (30 ml) was treated with diisopropylethylamine (1.6 ml, 9.2 mmol). After stirring at room temperature for 5 minutes the mixture was treated with (R)-2-[(morpholine-4-carbonyl)-amino]-3-phenylmethanesulfonyl-propionic acid (1.73 g, 4.86 mmol) followed by HATU (1.68 g, 4.42 mmol). This mixture was stirred at room temperature overnight and then evaporated. The residue was subjected to flash chromatography on silica eluting with ethyl acetate and then a mixture of ethyl acetate and methanol to give morpholine-4-carboxylic acid [(R)-1-(2,6-dihydroxy-cyclohexylcarbamoyl)-2-phenylmethanesulfonyl-ethyl]-amide as a white solid (210 mg). MS: 470 (MH⁺).

A solution of morpholine-4-carboxylic acid [(R)-1-(2,6-dihydroxy-cyclohexylcarbamoyl)-2-phenylmethanesulfonyl-ethyl]-amide (90 mg, 0.19 mmol) in methylene chloride (6 ml) was treated with Dess-Martin periodinane (162 mg, 0.38 mmol). After stirring at room temperature for 2 hours the reaction mixture was washed with a solution of $Na_2S_2O_3$ in water (0.26M), then with saturated aqueous bicarbonate solution then with water, then dried over $Na_2SO_4$ and then evaporated under reduced pressure. The residue was subjected to flash chromatography on silica eluting with a mixture of ethyl acetate and heptane to give morpholine4-carboxylic acid [(R)-1-(6-oxo-cyclohex-1-enylcarbamoyl)-2-phenylmethanesulfonyl-ethyl]-amide (8 mg). ¹H NMR (CDCl₃): 9.00 (s, 1H), 7.82 (t, J=5 Hz, 1H), 7.53–7.38 (m, 5H), 6.06 (d, J=6 Hz, 1H), 5.00 (m, 1H), 4.47–4.27 (m, 2H), 3.85 (m, 1H), 3.77–3.62 (m, 4H), 3.48–3.36 (m, 4H), 3.27 (m, 1H), 2.58–2.46 (m, 4H), 2.08–1.97 (m, 2H). MS: 450 (MH⁺).

Example 7

Morpholine-4-carboxylic acid [(R)-2-cyclopropyl-methanesulfonyl-1-(6-oxo-cyclohex-1-enylcarbamoyl)-ethyl]-amide (Compound 9)

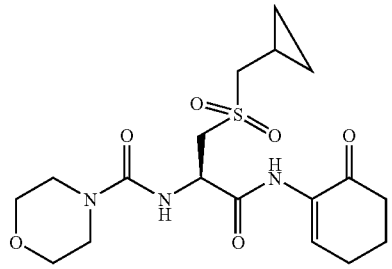

A mixture of (R)-3-cyclopropylmethanesulfonyl-2-[(morpholine-4-carbonyl)-amino]-propionic acid (0.352 g, 1.1 mmol) and N-cyclohexylcarbodiimide N'-methylpolystyrene (1.93 mmol/g, 1.03 g) in DCM (10 mL) was treated with hydroxybenzotriazole (0.27 g, 2 mmol). After stirring at room temperature for 5 minutes the mixture was treated with 2-amino-cyclohexane-1,3-diol (0.0.13 g, 1 mmol) and stirring was continued for a further 2 days. The reaction mixture was treated with PS Trisamine (3.75 mmol/g, 1.3 g) and after stirring at room temperature for 2 hours the resin was filtered off and washed with DCM. The combined filtrate plus washings were evaporated under reduced pressure to give morpholine-4-carboxylic acid [(R)-2-cyclopropylmethanesulfonyl-1-(2,6-dihydroxy-cyclohexylcarbamoyl)-ethyl]-amide (0.32 g) as pale yellow thick oil. MS: 434 (MH⁺).

Dess Martin Periodinane (0.688 g, 1.62 mmol) was added to a solution of the [(R)-2-cyclopropylmethanesulfonyl-1-(2,6-dihydroxy-cyclohexylcarbamoyl)-ethyl]-amide (0.32 g) in DCM (10 mL) and the mixture was stirred at room temperature for 3 hours then treated with resin bound $Na_2S_2O_3$ (1.5 mmol/g, 1.9 g) and stirred at room temperature for a further 24 hours. The reaction mixture was diluted with DCM (20 mL), then filtered. The filtrate was washed with a solution of 0.25 M $Na_2S_2O_3$, then with saturated $NaHCO_3$, then dried ($MgSO_4$), and then evaporated under reduced pressure. The residue was subjected to column chromatography eluting with a mixture of ethyl acetate and heptane to give morpholine-4-carboxylic acid [(R)-2-cyclopropyl-methanesulfonyl-1-(6-oxo-cyclohex-1-enylcarbamoyl)-ethyl]-amide. ¹H NMR (CDCl₃): 9.00 (s, 1H), 7.78 (t, 1H), 6.18 (d, 1H), 4.9 (m, 1H), 3.85 (m, 1H), 3.77–3.62 (m, 4H), 3.58–3.45 (dd, 1H), 3.48–3.36 (m, 4H), 3.0 (d, 2H), 2.55–2.42 (m, 4H), 2.08–1.97 (m, 2H), 1.2 (m, 1H), 0.8–0.7 (m, 2H), 0.6–0.4 (m, 2H). MS: 414 (MH⁺).

Example 8

Morpholine-4-carboxylic acid [(R)-1-(3,4-dioxo-cyclopentylcarbamoyl)-2-phenylmethanesulfonyl-ethyl]-amide (Compound 10)

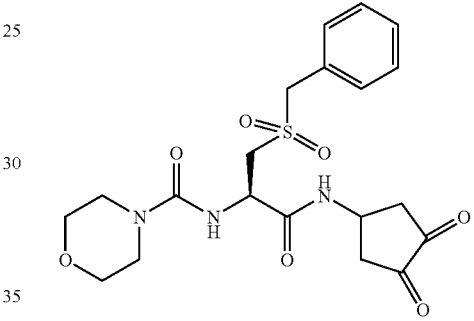

A solution of 4-amino-cyclopentane-1,2-diol; compound with trifluoroacetic acid (745 mg, 3.23 mmol) in DMF (15 ml) was treated with DIPEA (1.12 ml, 6.4 mmol) and the mixture was stirred for 5 minutes at room temperature. Then (R)-2-[(Morpholine-4-carbonyl)-amino]-3-phenylmethanesulfonyl-propionic acid (1.15 g, 3.23 mmol) was added followed by HATU (1.23 g, 3.24 mmol). This mixture was stirred at room temperature overnight and then evaporated. The residue was subjected to flash chromatography on silica eluting with ethyl acetate and then with a mixture of ethyl acetate and methanol to give morpholine-4-carboxylic acid [(R)-1-(3,4-dihydroxy-cyclopentylcarbamoyl)-2-phenylmethanesulfonyl-ethyl]-amide as a brown solid (680 mg). LC/MS: RT=2.64 min. (215 and 254 nM), MH⁺=456.

A solution of morpholine-4-carboxylic acid [(R)-1-(3,4-dihydroxy-cyclopentylcarbamoyl)-2-phenylmethanesulfonyl-ethyl]-amide (670 mg, 1.47 mmol) in methylene chloride (40 ml) was treated with Dess-Martin periodinane (624 mg, 1.47 mmol) and the reaction stirred at room temperature overnight. More Dess-Martin periodinane (642 mg, 1.51 mmol) was added and the reaction stirred at room temperature for 6 hours and then overnight. The reaction mixture was washed with a solution of $Na_2S_2O_3$ in water (0.26M), then with saturated aqueous bicarbonate solution, then with water, then dried over $Na_2SO_4$ and then evaporated under reduced pressure. The residue was subjected to flash chromatography on silica eluting with a mixture of ethyl acetate and heptane, then with ethyl acetate to give morpholine-4-carboxylic acid [(R)-1-(3,4-dioxo-cyclopentylcarbamoyl)-2-phenylmethanesulfonyl-ethyl]-amide as an off white solid (45 mg). ¹H NMR (CDCl₃): 7.50–7.38 (m, 5H), 6.62 (m, 1H), 5.91 (d, J=5 Hz, 1H), 4.81 (m, 1H), 4.58–4.35 (m, 3H), 3.73–3.61 (m, 5H), 3.44–3.32 (m, 4H), 3.22 (m, 1H), 2.72–2.12 (m, 4H). MS: 452 (MH⁺).

Example 9

Morpholine-4-carboxylic acid [2-(2-difluoromethoxy-phenylmethanesulfonyl)-1-(2-oxo-cyclohexylcarbamoyl)-ethyl]-amide (Compound 11)

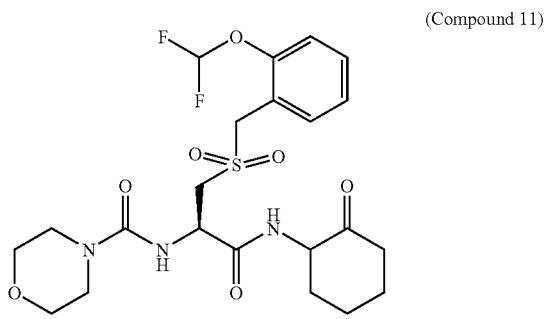

-3-(2-Difluoromethoxy-phenylmethanesulfonyl)-2-[(morpholine-4-carbonyl)-amino]-propionic acid (100 mg, 0.237 mmol), 2-aminocyclohexanol (58 mg, 0.5 mmol), EDC (100 mg, 0.52 mmol), and HOBt (100 mg, 0.64 mmol) were combined. Dichloromethane (2 mL) was added and then 4-methylmorpholine (0.2 mL). The mixture was stirred at ambient temperature for 2 h. After dilution with ethyl acetate (100 mL) the solution was washed with 1N aqu. HCl (30 mL), sat. aqu. NaHCO₃ (30 mL) and brine (30 mL), dried with MgSO₄ and evaporated under vacuum. The crude product was dissolved in dichloromethane (10 mL). Dess-Martin periodinane (300 mg, 0.71 mmol) was added, and the reaction mixture was stirred at ambient temperature for 1 h. After dilution with ethyl acetate (100 mL), the solution was washed with 0.26M Na₂S₂O₃ in sat. aqu. NaHCO₃ (30 mL), sat. aqu. NaHCO₃ and brine, dried with MgSO₄, and evaporated under vacuum. Purification by flash-chromatography on silica gel (ethyl acetate/hexane) gave morpholine-4-carboxylic acid [2-(2-difluoromethoxy-phenylmethanesulfonyl)-1-(2-oxo-cyclohexylcarbamoyl)-ethyl]-amide (78 mg, 0.151 mmol) as a white solid. Mixture of diastereomers: ¹H NMR: (DMSO) [8.03 (d, J=7.2 Hz), 7.96 (d, J=7.2 Hz), 1H], 7.50–7.42 (m, 2H), 7.30–7.21 (m, 2H), 7.10 (t, $J_{H,F}$=74 Hz, 1H), 7.03 (d, J=8.4 Hz, 1H), 4.78–4.69 (m, 1H), 4.54 (s, 2H), 4.41–4.33 (m, 1H), 3.62–3.25 (m, 10H), 2.55–1.40 (m, 8H). MS: (M+H)⁺ 518.

By proceeding in similar manner to Example 9 but using 2-aminocyclopentanol there was prepared morpholine-4-carboxylic acid [2-(2-difluoromethoxy-phenylmethanesulfonyl)-1-(2-oxo-cyclopentylcarbamoyl)-ethyl]-amide (Compound 12) as a mixture of diastereomers: ¹H NMR: (DMSO) [8.19 (d, J=8 Hz), 7.15 (d, J=8 Hz), 1H], 7.49–7.42 (m, 2H), 7.30–7.21 (m, 2H), 7.10 (t, $J_{H,F}$=74 Hz, 1H), [7.02 (d, J=8.4 Hz), 7.00 (d, J=8.4 Hz), 1H], 4.77–4.70 (m, 1H), [4.53 (s), 4.52 (s), 2H], 4.10–3.91 (m, 1H), 3.60–3.23 (m, 10H), 2.28–1.70 (m, 6H). MS: (M+H)⁺ 504.

By proceeding in similar manner to Example 9 but using 2-aminocyclobutanol there was prepared morpholine-4-carboxylic acid [2-(2-difluoromethoxy-phenylmethanesulfonyl)-1-(2-oxo-cyclobutylcarbamoyl)-ethyl]-amide (Compound 13) as a mixture of diastereomers: ¹H NMR: (DMSO) 8.49 (d, J=7.6 Hz, 1H), 7.48–7.42 (m, 2H), 7.30–7.21 (m, 2H), 7.11 (t, $J_{H,F}$=74 Hz, 1H), 7.02 (d, J=8.8 Hz, 1H), 4.88–4.67 (m, 2H), 4.53 (s, 2H), 3.64–3.23 (m, 10H), 2.93–2.70 (m, 2H), 2.23–1.99 (m, 2H). MS: (M+H)⁺

Example 10

(Morpholine-4-carboxylic acid [1-(2-benzylcarbamoyl-2-oxo-ethylcarbamoyl)-2-phenylmethanesulfonyl-ethyl]-amide)

(Compound 14)

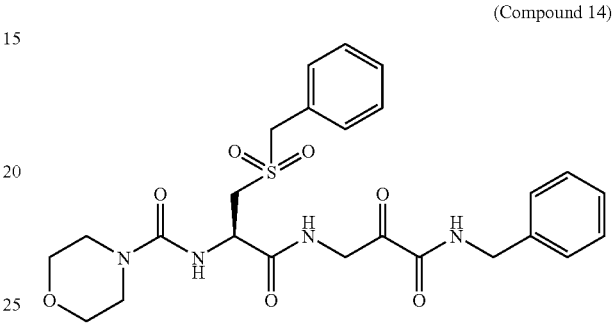

(Compound 15)

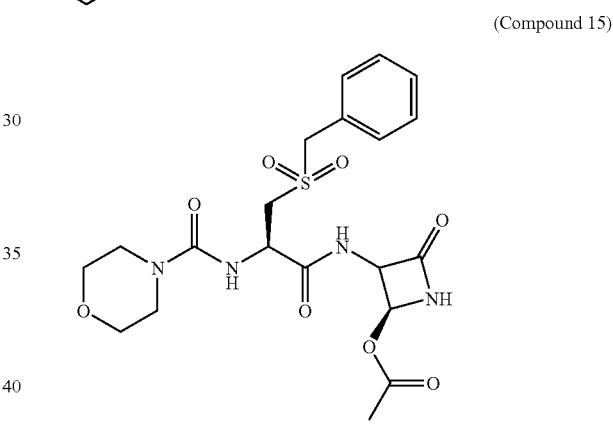

Isoserine (3.11 g, 29.6 mmol) was dissolved in 1,4-dioxane/H₂O 3:1 (40 mL). K₂CO₃ (0.5 g) and NaHCO₃ (0.5 g) was added. Di-tert-butyl dicarbonate (6.45 g, 29.6 mmol) was added and the mixture was stirred at ambient temperature over night. The reaction mixture was extracted with dichloromethane (3×100 mL). The combined organic phases were washed with brine, dried with MgSO₄, and evaporated under vacuum. The crude 3-tert-butoxycarbonylamino-2-hydroxy-propionic acid (4.76 g, 23.2 mmol) was obtained as a colorless oil, which solidified on standing, and was used without further purification.

3-tert-butoxycarbonylamino-2-hydroxy-propionic acid (1.5 g, 7.31 mmol), benzylamine (1.1 mL, 10.0 mmol), EDC (2.5 g, 13.1 mmol), and HOBt (2.0 g, 12.8 mmol) were combined. Dichloromethane (15 mL) was added and then 4-methylmorpholine (2 mL). The mixture was stirred at ambient temperature for 2 h. After dilution with ethyl acetate (300 mL) the solution was washed with 1N aqu. HCl (100 mL), sat. aqu. NaHCO₃ (100 mL) and brine (100 mL), dried with MgSO₄ and evaporated under vacuum. Yield: 1.83 g, 6.22 mmol (2-Benzylcarbamoyl-2-hydroxy-ethyl)-carbamic acid tert-butyl ester.

(2-Benzylcarbamoyl-2-hydroxy-ethyl)-carbamic acid tert-butyl ester (0.2 g, 0.68 mmol) was dissolved in dichloromethane (2 mL) and trifluoroacetic acid (2 mL). After stirring for 2 h at ambient temperature, the solution was evaporated under vacuum and the residue was dried under high vacuum. To this residue were added EDC (200 mg, 1.05 mmol), HOBt (200 mg, 1.28 mmol), 2-[(Morpholine-4-carbonyl)-amino]-3-phenylmethanesulfonyl-propionic acid (200 mg, 0.56 mmol), dichloromethane (5 mL) and 4-methylmorpholine (0.5 mL). The mixture was stirred at ambient temperature for 2 h. After dilution with ethyl acetate (100 mL) the solution was washed with 1N aqu. HCl (30 mL), sat. aqu. NaHCO$_3$ (30 mL) and brine (30 mL), dried with MgSO$_4$ and evaporated under vacuum. The crude product was dissolved in dichloromethane (10 mL). Dess-Martin periodinane (500 mg, 1.18 mmol) was added, and the reaction mixture was stirred at ambient temperature for 1 h. After dilution with ethyl acetate (100 mL), the solution was washed with 0.26M Na$_2$S$_2$O$_3$ in sat. aqu. NaHCO$_3$ (30 mL), sat. aqu. NaHCO$_3$ and brine, dried with MgSO$_4$, and evaporated under vacuum. The product (morpholine-4-carboxylic acid [1-(2-benzylcarbamoyl-2-oxo-ethylcarbamoyl)-2-phenylmethanesulfonyl-ethyl]-amide) was crystallized from ethyl acetate/diethylether and was obtained as a white solid (153 mg, 0.29 mmol). $^1$H NMR: (DMSO) 9.24 (t, J=6.4 Hz, 1H), 8.19 (t, J=5.6 Hz, 1H), 7.39–7.19 (m, 10H), 7.08 (d, J=8 Hz, 1H), 4.83–4.76 (m, 1H), 4.49 (s, 2H), 4.48–4.33 (m, 2H), 4.31 (d, J=6.8 Hz, 2H), 3.68–3.25 (m, 10H). MS: (M+H)$^+$ 531.

Example 11

Acetic acid 3-{2-[(morpholine-4-carbonyl)-amino]-3-phenylmethanesulfonyl-propionylamino}-4-oxo-azetidin-2-yl ester

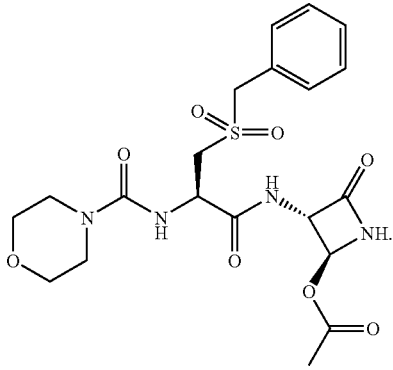

(Compound 15)

Acetic acid 3-benzyloxycarbonylamino-4-oxo-azetidin-2-yl ester was prepared as outlined in J. C. Arnould et al. *Eur. J. Med. Chem* 1992, 27, 131–140.

Acetic acid 3-benzyloxycarbonylamino-4-oxo-azetidin-2-yl ester (100 mg, 0.36 mmol) was hydrogenated on a Parr shaker over 10% palladium on carbon (100 mg) in ethyl acetate (20 ml) at 50 psi for 5 h. The mixture was filtered through Celite and evaporated. Acetic acid 3-amino-4-oxo-azetidin-2-yl ester was obtained in quantitative yield.

2-[(Morpholine-4-carbonyl)-amino]-3-phenylmethane-sulfonyl-propionic acid (100 mg, 0.28 mmol), acetic acid 3-amino-4-oxo-azetidin-2-yl ester (52 mg, 0.36 mmol), EDC (100 mg, 0.52 mmol), and HOBt (100 mg, 0.64 mmol) were combined. Dichloromethane (2 mL) was added and then 4-methylmorpholine (0.2 mL). The mixture was stirred at ambient temperature for 2 h. After dilution with ethyl acetate (100 mL) the solution was washed with 1N aqu. HCl (30 mL), sat. aqu. NaHCO$_3$ (30 mL) and brine (30 mL), dried with MgSO$_4$ and evaporated under vacuum. The residue was subjected to flash chromatography on silica gel (ethyl acetate) to give acetic acid 3-{2-[(morpholine-4-carbonyl)-amino]-3-phenylmethanesulfonyl-propionylamino}-4-oxo-azetidin-2-yl ester (17 mg, 0.035 mmol). $^1$H NMR: (DMSO) 9.18 (s, 1H), 8.72 (d, J=6.4 Hz, 1H), 7.41–7.30 (m, 5H), 7.08 (m, 1H), 5.76 (s, 1H), 4.80–4.61 (m, 2H), 4.49 (s, 2H), 3.63–3.22 (m, 10H), 2.08 (s, 3H). MS: (M+H)$^+$ 483.

Example 12

Morpholine-4-carboxylic acid [1-(4-oxo-tetrahydro-furan-3-ylcarbamoyl)-2-phenylmethanesulfonyl-ethyl]-amide

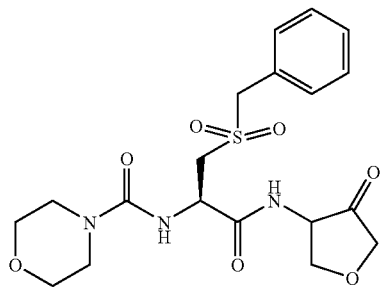

(Compound 16)

4-Amino-tetrahydro-furan-3-ol was prepared as outlined in Marquis, Robert W. et al. *J. Med. Chem* 2001, 44, 725–736.

2-[(Morpholine-4-carbonyl)-amino]-3-phenylmethane-sulfonyl-propionic acid (100 mg, 0.28 mmol), 4-aminotetrahydrofuran-3-ol (100 mg, 0.96 mmol), EDC (200 mg, 1.04 mmol), and HOBt (200 mg, 1.28 mmol) were combined. DMF (2 mL) was added and then 4-methylmorpholine (0.2 mL). The mixture was stirred at ambient temperature for 2 h. After dilution with ethyl acetate (100 mL) the solution was washed with 1N aqu. HCl (30 mL), sat. aqu. NaHCO$_3$ (30 mL) and brine (30 mL), dried with MgSO$_4$ and evaporated under vacuum. The crude product was dissolved in dichloromethane (10 mL). Dess-Martin periodinane (300 mg, 0.71 mmol) was added, and the reaction mixture was stirred at ambient temperature for 1 h. After dilution with ethyl acetate (100 mL), the solution was washed with 0.26M Na$_2$S$_2$O$_3$ in sat. aqu. NaHCO$_3$ (30 mL), sat. aqu. NaHCO$_3$ and brine, dried with MgSO$_4$, and evaporated under vacuum. Purification by flash-chromatography on silica gel (ethyl acetate) gave morpholine-4-carboxylic acid [1-(4-oxo-tetrahydro-furan-3-ylcarbamoyl)-2-phenylmethane-sulfonyl-ethyl]-amide (8.6 mg, 0.020 mmol) as a colorless glass. Mixture of diastereomers: $^1$H NMR: (DMSO) [8.42 (d, J=6.8 Hz), 7.15 (d, J=7.2 Hz), 1H], 7.40–7.32 (m, 5H), [7.06 (d, J=8 Hz), 7.05 (d, J=8 Hz), 1H], 4.78–4.68 (m, 1H), 4.49 (s), 4.48 (s), 2H], 4.32–3.75 (m, 5H), 3.60–3.23 (m, 10H). MS: (M+H)$^+$ 440.

Example 13

Morpholine-4-carboxylic acid [1-(2-hydroxy-1,1-dimethyl-3-oxo-3-phenyl-propylcarbamoyl)-2-phenylmethanesulfonyl-ethyl]-amide (Compound 17)

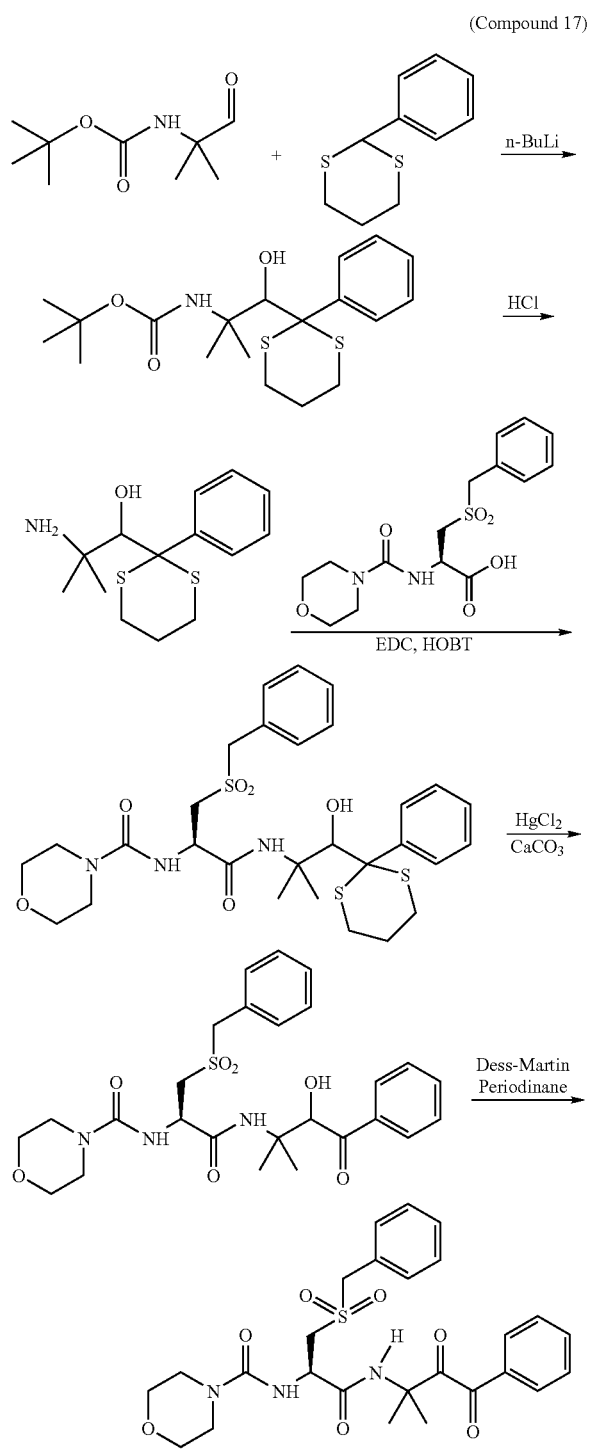

Step 1 To a flask fitted with a septum and stirbar under a nitrogen atmosphere containing 4.1 g (20 mmol) of 2-phenyl-1,3-dithiane (Aldrich) was added dry distilled TRF (20 mL). The solution was cooled to −30° C. and n-butyl lithium (1.6M in pentane, 16.8 mmol, 10.5 mL) was added slowly by syringe. The reaction mixture was warmed to −20° C. and held at that temperature for 30 minutes, and then held at −10° C. for 15 minutes. The yellow solution was cooled to −78° C. and (1,1-dimethyl-2-oxo-ethyl)-carbamic acid tert-butyl ester (1.5 g, 8 mmol, in 5 ml THF) was added rapidly (over 30 seconds) and 60 seconds later a solution of 2 mL acetic acid and 5 mL THF was added rapidly. The cooling bath was removed and 4 minutes later water was added and the mixture was extracted with ethyl acetate. The solvent was removed under reduced pressure and then recrystallized from 10 ml of ethyl acetate. The white crystals were washed three times with ethyl acetate and dried under reduced pressure to afford [2-hydroxy-1,1-dimethyl-2-(2-phenyl-[1,3]dithian-2-yl)-ethyl]-carbamic acid tert-butyl ester (1.6 g, 52%).

Step 2 To [2-hydroxy-1,1-dimethyl-2-(2-phenyl-[1,3]dithian-2-yl)-ethyl]-carbamic acid tert-butyl ester (1 g, 2.6 mmol) in 4.8 mL dioxane at 10° C. was added hydrochloric acid (4.8 mL, 4M in dioxane). The solution was warmed to 23° C. After 2 hours the solution was concentrated to 4 ml and diluted with ether to afford a white precipitate that was collected by filtration. The mother liquor was concentrated to a paste and triturated with ether. The solids were combined to afford 726 mg of 2-amino-2-methyl-1-(2-phenyl-[1,3]dithian-2-yl)-propan-1-ol (98% yield).

Step 3 2-Amino-2-methyl-1-(2-phenyl-[1,3]dithian-2-yl)-propan-1-ol and 2-[(morpholine-4-carbonyl)-amino]-3-phenylmethanesulfonyl-propionic acid were coupled using the standard peptide coupling conditions hereinbefore described to afford morpholine-4-carboxylic acid {1-[2-hydroxy-1,1-dimethyl-2-(2-phenyl-[1,3]dithian-2-yl)-ethylcarbamoyl]-2-phenylmethanesulfonyl-ethyl}-amide (270 mg, 78%).

Step 4 To morpholine-4-carboxylic acid {1-[2-hydroxy-1,1-dimethyl-2-(2-phenyl-[1,3]dithian-2-yl)-ethylcarbamoyl]-2-phenylmethanesulfonyl-ethyl}-amide (200 mg, 0.32 mmol) in 5.25 ml of 4:1 acetonitrile:water at 23° C. was simultaneously added finely ground $HgCl_2$ (192 mg, 0.7 mmol) and finely ground calcium carbonate (80 mg, 0.8 mmol) with stirring. The mixture was stirred for 10 minutes and then diluted with ethyl acetate. Methylene chloride was added and the organics were washed with water. After separation the organic layer concentrated to a gum that solidified upon addition of ether. The ether was removed under reduced pressure to afford a white solid. The solid was dissolved in a minimum of hot methylene chloride and filtered to remove insoluble material. The solution was concentrated to afford morpholine-4-carboxylic acid [1-(2-hydroxy-1,1-dimethyl-3-oxo-3-phenyl-propylcarbamoyl)-2-phenylmethanesulfonyl-ethyl]-amide (165 mg, 100% yield).

Step 5 [1-(2-hydroxy-1,1-dimethyl-3-oxo-3-phenyl-propylcarbamoyl)-2-phenylmethanesulfonyl-ethyl]-amide was oxidized in the usual manner to afford morpholine-4-carboxylic acid [1-(2-hydroxy-1,1-dimethyl-3-oxo-3-phenyl-propylcarbamoyl)-2-phenylmethanesulfonyl-ethyl]-amide. $^1$HNMR: ($CDCl_3$) [8.0 (d, J=8 Hz) 1H], 7.7–7.2 (m, 10H), [5.9 (d, J =6 Hz) 1H], [4.8 (d, J=6 Hz) 1H], [4.3 (d, J=14, Hz) 1H], [4.1 (d, J=14 Hz) 1H], 3.7 (m, 4H), 3.36 (m, 4H), [3.3 (d, J=2 Hz) 1H], [3.29 (d, J=2 Hz) 1H], 1.7(s, 6H). LCMS: elution time=3.71 min. 527.6(M−1), 529.6(M+1).(MS: API 150EX. LC: HP Agilent 1100 Series. Column: Phenomenex, 5u ODS3 100A 100×3 mm.; Flow Rate: 2 ml/min. Two solvent gradient: Solvent A, 99% water, 1% acetonitrile, 0.1% AcOH. Solvent B, 99% actonitrile, 1% water, 0.1% AcOH. Gradient from 100% A, 0% B to 0% A, 100% B from t=0 to t=6 min. Then gradient back to 100% A, 0% B from t=7 to t=15 min.).

By proceeding in a similar manner to Example 13 but using 3-(2-difluoromethoxy-phenylmethanesulfonyl)-2-[(morpholine-4-carbonyl)-amino]-propionic acid in step 3 there was prepared morpholine-4-carboxylic acid [2-(2-difluoromethoxy-phenylmethanesulfonyl)-1-(1,1-dimethyl-2,3-dioxo-3-phenyl-propylcarbamoyl)-ethyl]-amide.

LC-MS: elution time=3.95 min. 593.4(M−1), 596.2(M+1). (MS: API 150EX. LC: HP Agilent 1100 Series. Column: Phenomenex, 5u ODS3 100A 100×3 mm.; Flow Rate: 2 ml/min. Two solvent gradient: Solvent A, 99% water, 1% acetonitrile, 0.1% AcOH. Solvent B, 99% actonitrile, 1% water, 0.1% AcOH. Gradient from 100% A, 0% B to 0% A, 100% B from t=0 to t=6 min. Then gradient back to 100% A, 0% B from t=7 to t=15 min.)

Example 14

Cathepsin S Assay

Solutions of test compounds in varying concentrations were prepared in 10 μL of dimethyl sulfoxide (DMSO) and then diluted into assay buffer (40 μL, comprising: MES, 50 mM (pH 6.5); EDTA, 2.5 mM; and NaCl, 100 mM). Human cathepsin S (0.158 pMoles in 25 μL of assay buffer) was added to the dilutions. The assay solutions were mixed for 5–10 seconds on a shaker plate, covered and incubated for 30 minutes at ambient temperature. Z-Val-Val-Arg-AMC (9 nMoles in 25 μL of assay buffer) was added to the assay solutions and hydrolysis was followed spectrophotometrically at ($\lambda$ 460 nm) for 5 minutes. Apparent inhibition constants ($K_i$) were calculated from the enzyme progress curves using standard mathematical models.

Example 15

Cathepsin B Assay

Solutions of test compounds in varying concentrations were prepared in 10 μL of dimethyl sulfoxide (DMSO) and then diluted into assay buffer (40 μL, comprising: N,N-bis (2-hydroxyethyl)-2-aminoethanesulfonic acid (BES), 50 mM (pH 6); polyoxyethylenesorbitan monolaurate, 0.05%; and dithiothreitol (DTT), 2.5 mM). Human cathepsin B (0.025 pMoles in 25 μL of assay buffer) was added to the dilutions. The assay solutions were mixed for 5–10 seconds on a shaker plate, covered and incubated for 30 minutes at ambient temperature. Z-FR-AMC (20 nMoles in 25 μL of assay buffer) was added to the assay solutions and hydrolysis was followed spectrophotometrically at ($\lambda$ 460 nm) for 5 minutes. Apparent inhibition constants ($K_i$) were calculated from the enzyme progress curves using standard mathematical models.

Example 16

Cathepsin K Assay

Solutions of test compounds in varying concentrations were prepared in 10 μL of dimethyl sulfoxide (DMSO) and then diluted into assay buffer (40 μL, comprising: MES, 50 mM (pH 5.5); EDTA, 2.5 mM; and DTT, 2.5 mM). Human cathepsin K (0.0906 pMoles in 25 μL of assay buffer) was added to the dilutions. The assay solutions were mixed for 5–10 seconds on a shaker plate, covered and incubated for 30 minutes at ambient temperature. Z-Phe-Arg-AMC (4 nMoles in 25 μL of assay buffer) was added to the assay solutions and hydrolysis was followed spectrophotometrically at ($\lambda$ 460 nm) for 5 minutes. Apparent inhibition constants ($K_i$) were calculated from the enzyme progress curves using standard mathematical models.

Example 17

Cathepsin L Assay

Solutions of test compounds in varying concentrations were prepared in 10 μL of dimethyl sulfoxide (DMSO) and then diluted into assay buffer (40 μL, comprising: MES, 50 mM (pH 5.5); EDTA, 2.5 mM; and DTT, 2.5 mM). Human cathepsin L (0.05 pMoles in 25 μL of assay buffer) was added to the dilutions. The assay solutions were mixed for 5–10 seconds on a shaker plate, covered and incubated for 30 minutes at ambient temperature. Z-Phe-Arg-AMC (1 nMoles in 25 μL of assay buffer) was added to the assay solutions and hydrolysis was followed spectrophotometrically at ($\lambda$ 460 nm) for 5 minutes. Apparent inhibition constants ($K_i$) were calculated from the enzyme progress curves using standard mathematical models.

Some of the compounds of the invention tested according to the above-described assays for protease inhibition were observed to exhibit selective cathepsin S inhibitory activity. The apparent inhibition constants ($K_i$) for compounds of the invention, against Cathepsin S, were in the range from about $10^{-10}$M to about $10^{-7}$M.

Example 18

Representative Pharmaceutical Formulations Containing a Compound of Formula I

ORAL FORMULATION

Compound of Formula I 10–100 mg
Citric Acid Monohydrate 105 mg
Sodium Hydroxide 18 mg
Flavoring
Water q.s. to 100 mL Intravenous Formulation Compound of Formula I 0.1–10 mg
Dextrose Monohydrate q.s. to make isotonic
Citric Acid Monohydrate 1.05 mg
Sodium Hydroxide 0.18 mg
Water for Injection q.s. to 1.0 mL

TABLET FORMULATION

Compound of Formula I 1%
Microcrystalline Cellulose 73%
Stearic Acid 25%
Colloidal Silica 1%.

We claim:
1. A compound of Formula I:

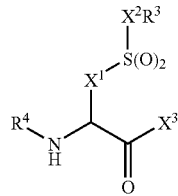

in which:
X$^1$ and X$^2$ are both methylene or X$^1$ is ethylene and X$^2$ is a bond;
R$^3$ is —CR$^5$=CHR$^6$, —CR$^5$(CR$^6$$_3$)$_2$ or —CR$^7$=NR$^8$, wherein R$^5$ is hydrogen and R$^6$ is hydrogen or (C$_{1-4}$)alkyl or R$^5$ and R$^6$ together with the atoms to which R$^5$ and R$^6$ are attached form (C$_{3-12}$)cycloalkenyl, hetero(C$_{5-12}$)cycloalkenyl, (C$_{6-12}$)aryl, hetero(C$_{6-12}$)aryl, (C$_{9-12}$)bicycloaryl or hetero(C$_{8-12}$)bicycloaryl and R$^7$ and R$^8$ together with the atoms to which R$^7$ and R$^8$ are attached form hetero(C$_{5-12}$)cycloalkenyl, hetero(C$_{6-12}$)aryl or hetero(C$_{8-12}$)bicycloaryl, wherein R$^3$ optionally is substituted by 1 to 5 radicals independently selected from a group consisting of (C$_{1-4}$)alkyl, cyano, halo, halo-substituted (C$_{1-4}$)alkyl, nitro, —X$^4$NR$^9$R$^9$, —X$^4$OR$^9$, —X$^4$SR$^9$, —X$^4$C(O)NR$^9$R$^9$, —X$^4$C(O)OR$^9$, —X$^4$S(O)R$^{10}$, —X$^4$S(O)$_2$R$^{10}$ and —X$^4$C(O)R$^{10}$, wherein X$^4$ is a bond or (C$_{1-2}$)alkylene, R$^9$ at each occurrence independently is hydrogen, (C$_{1-3}$)alkyl or halo-substituted (C$_{1-3}$)alkyl and R$^{10}$ is (C$_{1-3}$)alkyl or halo-substituted (C$_{1-3}$)alkyl; and
R$_4$ is —C(O)X$^5$R$^{11}$ —or —S(O)$_2$X$^5$R$^{11}$, wherein X$^5$ is a bond, —O— or —NR$^{12}$—, wherein R$^{12}$ is hydrogen or (C$_{1-6}$)alkyl, and R$^{11}$ is (i) (C$_{1-6}$)alkyl optionally substituted by —OR$^{13}$, —SR$^{13}$, —S(O)R$^{13}$, —S(O)$_2$R$^{13}$, —C(O)R$^{13}$, —C(O)NR$^{13}$R$^{14}$, —NR$^{13}$R$^{14}$, —NR$^{14}$C(O)R$^{13}$, —NR$^{14}$C(O)OR$^{13}$, NR$^{14}$C(O)NR$^{13}$R$^{14}$ or —NR$^{14}$C(NR$^{14}$)NR$^{13}$R$^{14}$, wherein R$^{13}$ is (C$_{3-12}$)cycloalkyl(C$_{0-3}$)alkyl, hetero(C$_{5-12}$)cycloalkyl(C$_{0-3}$)alkyl, (C$_{6-12}$)aryl(C$_{0-3}$)alkyl, hetero(C$_{5-12}$)aryl(C$_{0-3}$)alkyl, (C$_{9-12}$)bicycloaryl(C$_{0-3}$)alkyl or hetero(C$_{8-12}$)bicycloaryl(C$_{0-3}$)alkyl and R$^{14}$ at each occurrence independently is hydrogen or (C$_{1-6}$)alkyl, or (ii) (C$_{3-12}$)cycloalkyl(C$_{0-3}$)alkyl, hetero(C$_{5-12}$)cycloalkyl(C$_{0-3}$)alkyl, (C$_{6-12}$)aryl(C$_{0-3}$)alkyl, hetero(C$_{5-12}$)aryl(C$_{0-3}$)alkyl, (C$_{9-12}$)bicycloaryl(C$_{0-3}$)alkyl or hetero(C$_{8-12}$)bicycloaryl(C$_{0-3}$)alkyl or (iii) (C$_{3-6}$)cycloalkyl(C$_{0-3}$)alkyl, hetero(C$_{5-6}$)cycloalkyl(C$_{0-3}$)alky, phenyl(C$_{0-3}$)alkyl or hetero(C$_{5-6}$)aryl(C$_{0-3}$)alkyl substituted by —X$^6$OR$^{15}$, —X$^6$SR$^{15}$, —X$^6$S(O)R$^{15}$, —X$^6$SR$^{15}$,—X$^6$S(O)R$^{15}$, —X$^6$S(O)$_2$R$^{15}$, —X$^6$C(O)R$^{15}$, —X$^6$C(O)OR$^{15}$,—X$^6$C(O)NR$^{15}$R$^{16}$, —X$^6$NR$^{15}$R$^{16}$, —X$^6$NR$^{16}$C(O)R$^{15}$, —X$^6$NR$^{16}$C(O)OR$^{15}$, —X$^6$NR$^{16}$C(O)NR$^{15}$R$^{16}$, —X$^6$NR$^{16}$C(O)OR$^{16}$, —X$^6$NR$^{16}$C(NR$^{16}$)NR$^{15}$R$^{16}$, wherein X$^6$ is a bond or methylene, R$^{15}$ is (C$_{3-6}$)cycloalkyl(C$_{0-3}$)alkyl, hetero(C$_{5-6}$)cycoalkyl(C$_{0-3}$)alkyl, phenyl(C$_{0-3}$)alkyl or hetero(C$_{5-6}$)aryl(C$_{0-3}$)alkyl and R$^{16}$ is hydrogen or (C$_{1-6}$)alkyl; wherein R$^4$ optionally further contains 1 to 5 substituents which when occurring within an alicyclic or aromatic ring system are radicals independently selected from a group consisting of (C$_{1-6}$)alkyl, (C$_{1-6}$)alkylidene, cyano, halo, nitro, halo-substituted (C$_{1-3}$)alkyl, —X$^6$NR$^{17}$R$^{17}$, —X$^6$NR$^{17}$C(O)OR$^{17}$, —X$^6$NR$^{17}$C(O)NR$^{17}$R$^{17}$, —X$^6$NR$^{17}$C(NR$^{17}$)NR$^{17}$R$^{17}$, —X$^6$OR$^{17}$, —X$^6$SR$^{17}$, —X$^6$C(O)OR$^{17}$, —X$^6$C(O)NR$^{17}$R$^{17}$, —X$^6$S(O)$_2$NR$^{17}$R$^{17}$, —X$^6$P(O)(OR$^{18}$)OR$^{17}$, —X$^6$OP(O)(OR$^{18}$)OR$^{17}$, —X$^6$NR$^{17}$C(O)R$^{18}$, —X$^6$S(O)R$^{18}$, —X$^6$S(O)$_2$R$^{18}$ and —X$^6$C(O)R$^{18}$ and when occurring within an aliphatic moiety are radicals independently selected from a group consisting of cyano, halo, nitro, —NR$^{17}$R$^{17}$, —NR$^{17}$C(O)OR$^{17}$, —NR$^{17}$C(O)NR$^{17}$R$^{17}$, —NR$^{17}$C(NR$^{17}$)NR$^{17}$R$^{17}$, OR$^{17}$, —SR$^{17}$, —C(O)OR$^{17}$, —C(O)NR$^{17}$R$^{17}$, —S(O)$_2$NR$^{17}$R$^{17}$, —P(O)(OR$^{17}$)OR$^{17}$, OP(O)(OR$^{17}$)OR$^{17}$, -NR$^{17}$C(O)R$^{18}$, —S(O)R$^{18}$, —S(O)$_2$R$^{18}$ and —C(O)R$^{18}$, wherein X$^6$ is a bond or (C$_{1-6}$)alkylene, R$^{17}$ at each occurrence independently is hydrogen, (C$_{1-6}$)alkyl or halo-substituted (C$_{1-3}$)alkyl and R$^{18}$ is (C$_{1-6}$)alkyl or halo-substituted (C$_{1-3}$)alkyl;
X$^3$ is a group of Formula (a):

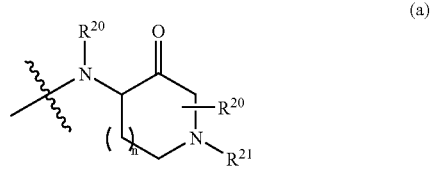

n is 0, 1 or 2;
R$^{20}$ is selected from the group consisting of hydrogen, (C$_{1-6}$)alkyl, (C$_{3-12}$)cycloalky(C$_{0-6}$)alkyl, hetero(C$_{5-12}$)cycloalkyl(C$_{0-6}$)alkyl, (C$_{6-12}$)aryl(C$_{0-6}$)alkyl and hetero(C$_{5-12}$)aryl(C$_{0-6}$)alkyl;
R$^{21}$ is selected from the group consisting of hydrogen, (C$_{1-9}$)alkyl, (C$_{3-12}$)cycloalkyl(C$_{0-6}$)alkyl, hetero(C$_{5-12}$)cycloalkyl(C$_{0-6}$)alkyl, (C$_{6-12}$)aryl(C$_{0-6}$)alkyl, hetero(C$_{5-12}$)aryl(C$_{0-6}$alkyl, (C$_{9-12}$)bicycloaryl(C$_{0-3}$)alkyl, hetero(C$_{8-12}$)—bicycloaryl(C$_{0-3}$)alkyl, —C(O)R$^{26}$, —C(S)R$^{26}$, —S(O)$_2$R$^{26}$, —C(O)OR$^{26}$—C(O)N(R$^{26}$)R$^{27}$, —C(S)N(R$^{26}$)R$^{27}$ and —S(O)$_2$N(R$^{27}$)R$^{26}$;
R$^{26}$ is selected from the group consisting of hydrogen, (C$_{1-6}$)alkyl, (C$_{3-12}$)cycloalkyl(C$_{0-6}$)alkyl, hetero(C$_{5-12}$)cycloalkyl(C$_{0-6}$)alkyl, (C$_{6-12}$)aryl(C$_{0-6}$)alkyl, hetero(C$_{5-12}$)aryl(C$_{0-6}$)alkyl, (C$_{9-12}$)bicycloaryl(C$_{0-3}$)alkyl or hetero(C$_{8-12}$)-bicycloaryl(C$_{0-3}$)alkyl;
R$^{27}$ is hydrogen, (C$_{1-6}$)alkyl, (C$_{3-12}$)cycloalkyl(C$_{0-6}$) alkyl, hetero(C$_{5-12}$)cycloalkyl(C$_{0-6}$)alkyl, (C$_{6-12}$)aryl (C$_{0-6}$)alkyl or hetero(C$_{5-12}$)aryl(C$_{0-6}$)alkyl;
wherein X$^3$ optionally further contains 1 to 5 substituents which when occurring within an alicyclic or aromatic ring system are radicals independently selected from a group consisting of (C$_{1-6}$)alkyl, (C$_{1-6}$)alkylidene, cyano, halo, nitro, halo-substituted (C$_{1-3}$)alkyl, —X$^6$NR$^{17}$R$^{17}$, —X$^6$NR$^{17}$C(O)OR$^{17}$, —X$^6$NR$^{17}$C(O)NR$^{17}$R$^{17}$, —X$^6$NR$^{17}$C(NR$^{17}$)NR$^{17}$R$^{17}$, —X$^6$OR$^{17}$, —X$^6$C(O)R$^7$, —X$^6$OR$^{15}$, —X$^6$SR$^{17}$, —X$^6$C(O)OR$^{17}$, —X$^6$C(O)NR$^{17}$R$^{17}$, —X$^6$S(O)$_2$NR$^{17}$R$^{17}$, —X$^6$P(O)(OR$^8$)OR$^{17}$, —X$^6$OP(O)(OR$^8$)OR$^{17}$, —X$^6$NR$^{17}$C(O)R$^{18}$, —X$^6$S(O)R$^{18}$, —X$^6$S(O)$_2$R$^{18}$ and —X$^6$C(O)R$^{18}$ and when occurring within an aliphatic moiety are radicals independently selected from a group consisting of cyano, halo, nitro, —NR$^{17}$R$^{17}$, —NR$^{17}$C(O)OR$^{17}$, —NR$^{17}$C(O)NR$^{17}$R$^{17}$, —NR$^{17}$C(NR$^{17}$)NR$^{17}$R$^{17}$, —OR$^{17}$, —SR$^{17}$, —C(O)OR$^{17}$, —C(O)NR$^{17}$R$^{17}$, —S(O)$_2$NR$^{17}$R$^{17}$, —P(O)(OR$^{17}$)OR$^{17}$, —OP(O)(OR$^{17}$)OR$^{17}$, —NR$^{17}$C(O)R$^{18}$, —S(O)R$^{18}$, —S(O)$_2$R$^{18}$ and —C(O)R$^{18}$, wherein R$^{15}$, R$^{17}$, R$^{18}$ and X$^6$ are as described above; and the N-oxide derivatives, prodrug derivatives, protected derivatives, individual isomers and mixtures of isomers thereof; and the pharmaceutically acceptable salts and solvates of such compounds and the N-oxide derivatives, prodrug derivatives, protected derivatives, individual isomers and mixtures of isomers thereof.

2. The compound of claim 1 in which $X^1$ and $X^2$ are both methylene or $X^1$ is ethylene and $X^2$ is a bond; $R^3$ is —$CR^5$=$CHR^6$, —$CR^5(CR_3^6)_2$ or —$CR^7$=$NR^8$, wherein $R^5$ is hydrogen and $R^6$ is hydrogen or $(C_{1-4})$alkyl or $R^5$ and $R^6$ together with the atoms to which $R^5$ and $R^6$ are attached form $(C_{3-12})$cycloalkenyl, $(C_{6-2})$aryl, hetero$(C_{6-12})$aryl or $(C_{9-12})$bicycloaryl and $R^7$ and $R^8$ together with the atoms to which $R^7$ and $R^8$ are attached form hetero$(C_{5-2})$cycloalkenyl or hetero$(C_{6-12})$aryl, wherein $R^3$ optionally is substituted by 1 to 5 radicals independently selected from a group consisting of $(C_{1-4})$alkyl, cyano, halo, halo-substituted $(C_{1-4})$alkyl, —$X^4OR^9$ and —$X^4C(O)OR^9$, wherein $X^4$ is a bond or $(C_{1-2})$alkylene, $R^9$ at each occurrence independently is $(C_{1-3})$alkyl or halo-substituted $(C_{1-3})$alkyl; and the N-oxide derivatives, prodrug derivatives, protected derivatives, individual isomers and mixtures of isomers thereof and the pharmaceutically acceptable salts and solvates of such compounds and the N-oxide derivatives, prodrug derivatives, protected derivatives, individual isomers and mixtures of isomers thereof.

3. The compound of claim 2 in which $R^4$ is —$C(O)X^5R^{11}$ or —$S(O)_2X^5R^{11}$, wherein $X^5$ is a bond, —O— or —$NR^{12}$—, wherein $R^{12}$ is hydrogen or $(C_{1-6})$alkyl, and $R^{11}$ is (i) $(C_{1-6})$alkyl or (ii) hetero$(C_{5-12})$cycloalkyl$(C_{0-3})$alkyl, $(C_{6-12})$aryl$(C_{0-3})$alkyl, hetero$(C_{5-12})$aryl$(C_{0-3})$alkyl, $(C_{9-12})$bicycloaryl$(C_{0-3})$alkyl or hetero$(C_{8-12})$bicycloaryl$(C_{0-3})$alkyl or (iii) hetero$(C_{5-6})$cycloalkyl$(C_{0-3})$alkyl or phenyl$(C_{0-3})$alkyl substituted by —$X^6OR^{15}$, —$X^6C(O)R^{15}$ or —$X^6NR^{16}C(O)OR^{16}$, wherein $X^6$ is a bond or methylene, $R^{15}$ is phenyl$(C_{0-3})$alkyl or hetero$(C_{5-6})$aryl$(C_{0-3})$alkyl and R16 is hydrogen or $(C_{1-6})$alkyl; wherein $R^4$ optionally further contains 1 to 5 substituents which when occurring within an alicyclic or aromatic ring system are radicals independently selected from a group consisting of $(C_{1-6})$alkyl, halo, —$X^6NR^{17}R^{17}$, —$X^6OR^{17}$, —$X^6C(O)OR^{17}$, —$X^6NC(O)R^{16}$ and —$X^6C(O)R^{18}$, $R^{17}$ at each occurrence independently is hydrogen, $(C_{1-6})$alkyl or halo-substituted $(C_{1-3})$alkyl and $R^{18}$ is $(C_{1-6})$alkyl or halo-substituted $(C_{1-3})$alkyl; and the N-oxide derivatives, prodrug derivatives, protected derivatives, individual isomers and mixtures of isomers thereof; and the pharmaceutically acceptable salts and solvates of such compounds and the N-oxide derivatives, prodrug derivatives, protected derivatives, individual isomers and mixtures of isomers thereof.

4. The compound of claim 3 in which $X^3$ is a group of Formula (a):

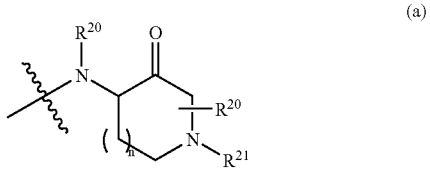

(a)

n is 0, 1 or 2;
$R^{20}$ is selected from the group consisting of hydrogen and $(C_{1-6})$alkyl;

$R^{21}$ is selected from the group consisting of $(C_{1-9})$alkyl, $(C_{6-12})$aryl$(C_{0-6})$alkyl, —$C(O)R^{26}$, —$S(O)_2R^{26}$, —$C(O)OR^{26}$ and —$C(O)N(R^{26})R^{27}$;

$R^{26}$ is selected from the group consisting of $(C_{1-6})$alkyl, hetero$(C_{5-12})$cycloalkyl$(C_{0-6})$alkyl, $(C_{6-12})$aryl$(C_{0-6})$alkyl, hetero$(C_{5-12})$aryl$(C_{0-6})$alkyl and $(C_{9-12})$bicycloaryl$(C_{0-3})$alkyl;

$R^{27}$ is $(C_{1-6})$alkyl;

wherein $X^3$ optionally further contains 1 to 5 substituents which when occurring within an alicyclic or aromatic ring system are radicals independently selected from a group consisting of $(C_{1-6})$alkyl, cyano, halo, —$X^6OR^{17}$, —$X^6C(O)R^{17}$ and —$X^6OR^{15}$; and the N-oxide derivatives, prodrug derivatives, protected derivatives, individual isomers and mixtures of isomers thereof and the pharmaceutically acceptable salts and solvates of such compounds and the N-oxide derivatives, prodrug derivatives, protected derivatives, individual isomers and mixtures of isomers thereof.

5. The compound of claim 4 in which $R^3$ is selected from the group consisting of phenyl, pyridin-2-yl, pyridin-3-yl, pyridin-4-yl, vinyl, 2-difluoromethoxyphenyl, 1-oxy-pyridin-2-yl, 4-methoxyphenyl, 4-methylphenyl, 2-methylphenyl, 4-chlorophenyl, 3,5-dimethylphenyl, 4-trifluoromethyiphenyl, 4-trifluoromethoxyphenyl, 2-bromophenyl, naphthalen-2-yl, 3,4-dichlorophenyl, 3-methylphenyl, 3-trifluoromethylphenyl, 3-trifluoromethoxyphenyl, 2,3,4,5,6-pentafluoro-phenyl, 2-fluorophenyl, 2-chlorophenyl, 2-cyano-phenyl, 2-trifluoromethyiphenyl, 4-tert-butyl-phenyl, 3-chlorophenyl, 4-bromophenyl, 2-fluoro-3-chloro-phenyl, 2-fluoro-3-methyl-phenyl, 3-fluorophenyl, 2,5-difluorophenyl, 3-bromophenyl, 2,5-dichlorophenyl, 2,6-difluorophenyl, 3-cyano-phenyl, 4-cyano-phenyl, 2-trifluoromethoxyphenyl, 2,3-difluorophenyl, biphenyl, 2-bromo-5-fluoro-phenyl, 4-fluorophenyl, 3,4-difluorophenyl, 2,4-difluorophenyl, 2,4,6-trifluorophenyl, 2,4,5-trifluorophenyl, 2,3,4-trifluorophenyl, 2-chloro-5-trifluoromethylphenyl, 2,4-bis-trifluoromethyiphenyl, 2,5,6-trifluorophenyl, 2-fluoro-3-trifluoromethylphenyl, 2-fluoro-4-trifluoromethylphenyl, 2-fluoro-5-trifluoromethylphenyl, 2,3,5-trifluorophenyl, 2-fluoro-5-trifluoromethylphenyl, 5-fluoro-2-trifluoromethylphenyl, 4-fluoro-3-trifluoromethylphenyl, 2-methoxyphenyl, 3,5-bis-trifluoromethyiphenyl, 4-difluoromethoxyphenyl, 3-difluoromethoxyphenyl, 2,6-dichiorophenyl, 4-carboxyphenyl, cyclohexyl, cyclopropyl, isopropyl, thiophen-2-yl, 5-chloro-thiophen-2-yl and 3,5-dimethyl-isoxazol-4-yl.

6. The compound of claim 5 in which $R^4$ is benzoyl, morpholine-4-carbonyl, acetyl, furan-3-carbonyl, 2-methoxy-benzoyl, 3-methoxy-benzoyl, naphthalene-2-carbonyl, benzo[1,3]dioxole-5-carbonyl, 3-pyridin-3-yl-acryloyl, benzofuran-2-carbonyl, furan-2-carbonyl, tert-butoxy-carbonyl, biphenyl-4-carbonyl, quinoline-2-carbonyl, quinoline-3-carbonyl, 3-acetyl-benzoyl, 4-phenoxy-benzoyl, 3-hydroxybenzoyl, 4-hydroxy-benzoyl, pyridine-3-carbonyl, 3-(tert-butoxycarbonylamino-methyl)-benzoyl, 4-carbonyl-piperazine-1-carboxylic acid tert-butyl ester, 4-carbonyl-piperazine-1-carboxylic acid ethyl ester, 4-(furan-2-carbonyl)-piperazine-1-carbonyl, pyridine-4-carbonyl, 1-oxy-pyridine-4-carbonyl, 1-oxy-pyridine-3-carbonyl, thiophene-2-carbonyl, thiophene-3-carbonyl, 4-benzoyl-benzoyl, 5-methyl-thiophene-2-carbonyl, 3-chloro-thiophene-2-carbonyl, 3-bromo-thiophene-2-carbonyl, 4-chloro-benzoyl, 3-fluoro-4-methoxy-benzoyl, 4-methoxy-benzoyl, 4-trifluoromethoxy-benzoyl, 3,4-diflouro-benzoyl, 4-fluoro-benzoyl, 3,4-dimethoxy-benzoyl, 3-methyl-benzoyl, 4-bromo-benzoyl, 4-triflouromethyl-benzoyl, 3-benzoyl-benzoyl, cyclopentane-carbonyl, benzo[b]thiophene-2-carbonyl, 3-chloro-benzo[b]thiophene-2-carbonyl, benzenesulfonyl, naphthalene-2-sulfonyl, 5-methyl-thiophene-2-sulfonyl, thiophene-2-sulfonyl, formamyl-methyl ester, 4-methyl-pentanoyl, formamyl-isobutyl ester, formamyl-monoallyl ester, formamyl-isopropyl ester, N,N-dimethyl-formamyl, N-isopropyl-formamyl, N-pyridin-4-yl-formamyl, N-pyridin-3-yl-formamyl, 3-phenyl-acryloyl, 1H-indole-5-carbonyl, pyridine-2-carbonyl, pyrazine-2-carbonyl, 3-hydroxy-pyridine-2-carbonyl, 2-amino-pyridine-3-carbonyl, 2-hydroxy-pyridine-3-carbonyl, 6-amino-pyridine-3-carbonyl, 6-hydroxy-pyridine-3-carbonyl, pyridazine-4-carbonyl, 3-phenoxy-benzoyl and 1-oxo-1,3-dihydro-isoindoie-2-carbonyl.

7. The compound of claim 6 in which $X^3$ is selected from a group consisting of 4-amino-3-oxo-azepane-1-carboxylic acid benzyl ester, 4-amino-3-oxo-azepane-1-carboxylic acid isobutyl ester, 4-amino-1-benzoyl-azepan-3-one, 4-amino-1-benzenesulfonyl-azepan-3-one, 4-amino-1-(pyridine-2-sulfonyl)-azepan-3-one, 4-amino-1-(1-oxy-pyridine-2-sulfonyl)-azepan-3-one, 4-amino-1-(3,4-dichloro-benzenesulfonyl)-azepan-3-one, 4-amino-1-(2-fluoro-benzenesulfonyl)-azepan-3-one, 4-amino-1-(3,4-dimethoxy-benzenesulfonyl)-azepan-3-one, 4-amino-1-(2-cyano-benzenesulfonyl)-azepan-3-one, 4-amino-1-(naphthalene-1-sulfonyl)-azepan-3-one, 4-amino-1-(thiophene-2-sulfonyl)-azepan-3-one, 4-amino-1-(thiazole-2-sulfonyl)-azepan-3-one, 4-amino-1-(pyrrolidine-1-sulfonyl)-azepan-3-one, 4-amino-1-methanesulfonyl-azepan-3-one, 4-amino-1-(pyrrolidine-1-carbonyl)-azepan-3-one, 4-amino-3-oxo-azepane-1-carboxylic-acid-dimethylamide, 4-amino-3-oxo-azepane-1-carboxylic-acid-benzylamide, 4-amino-1-benzyl-azepan-3-one, 4-amino-1-benzyl-piperidin-3-one, 4-amino-1-benzoyl-piperidin-3-one, 4-amino-1-benzoyl-pyrrolidin-3-one, 4-amino-1-benzyl-pyrrolidin-3-one, 4-amino-1-benzenesulfonyl-pyrrolidin-3-one and 4-amino-1-(5-methyl-hexyl)-pyrrolidin-3-one.

8. The compound of claim 7 selected from the group consisting of morpholine-4-carboxylic acid [1-(1-benzoyl-4-oxo-pyrrolidin-3-ylcarbamoyl)-2-phenylmethanesulfonyl-ethyl]-amide, morpholine-4-carboxylic acid [1-(1-benzenesulfonyl-4-oxo-pyrrolidin-3-ylcarbamoyl)-2-phenylmethanesulfonyl-ethyl]-amide and 4-{2-[(Morpholine-4-carbonyl)-amino]-3-phenylmethanesulfonyl-propionylamino}-3-oxo-azepane-1-carboxylic acid benzyl ester.

9. A pharmaceutical composition comprising a therapeutically effective amount of a compound of claim 1 in combination with a pharmaceutically acceptable excipient.

10. A method for treating allogeneic immune responses to organ transplants or tissue grafts, amyloidosis, aneurysms, arthritis, asthma, atheroma, atherosclerosis, bronchiolitis, bronchitis, cardiovascular disease, chronic obstructive pulmonary disease, Crithidia fusiculata, Crohn's disease, dermatitis, diabetes, disseminated intravascular coagulation, emphysema, endocrine hyperenergia, glomerulonephritis, Graves'disease, Guillain-Barre syndrome, Hashimoto's thyroiditis, hepatitis C, inflammatory airway disease, inflammatory bowel disease, ischemia, liver cirrhosis, lupus, malaria, metachromatic leukodystrophy, muscular dystrophy, myasthenia gravis, myocardial infarction, myocarditis, osteoarthritis, osteoporosis, pancreatitis, parasitosis, pemphigus vulgaris, periodontal disease, pneumonities, psoriasis, pycnodvsostosis, schistosomiasis, scleroderma, tissue graft rejections, Trypanosoma brucei, tumor-induced vascular lesions, ulcerative colitis or angina pectoris, which method comprises administering to the animal a therapeutically effective amount of compound of claim 1 or a N-oxide derivative or individual isomer or mixture of isomers thereof; or a pharmaceutically acceptable salt or solvate of such compounds and the N-oxide derivatives, prodrug derivatives, protected derivatives, individual isomers and mixtures of isomers thereof.

11. A process for preparing a compound of Formula I:

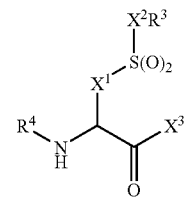

in which:

$X^1$ and $X^2$ are both methylene or $X^1$ is ethylene and $X^2$ is a bond;

$R^3$ is $-CR^5=CHR^6$, $-CR^5(CR^6_3)_2$ or $-CR^7=NR^8$, wherein $R^5$ is hydrogen and $R^6$ is hydrogen or $(C_{1-4}$ alkyl or $R^5$ and $R^6$ together with the atoms to which $R^5$ and $R^6$ are attached form $(C_{3-12})$cycloalkenyl, hetero$(C_{5-12})$cycloalkenyl, $(C_{6-12})$aryl, hetero$(C_{6-12})$aryl, $(C_{9-12})$bicycloaryl or hetero$(C_{8-12})$bicycloaryl and $R^7$ and $R^8$ together with the atoms to which $R^7$ and $R^8$ are attached form hetero$(C_{5-12})$cycloalkenyl, hetero$(C_{6-12})$aryl or hetero$(C_{8-12})$bicycloaryl, wherein $R^3$ optionally is substituted by 1 to 5 radicals independently selected from a group consisting of $(C_{1-4})$alkyl, cyano, halo, halo-substituted $(C_{1-4}$alkyl, nitro, $-X^4NR^9R^9$, $-X^4OR^9$, $-X^4SR^9$, $-X^4C(O)NR^9R^9$, $-X^4C(O)OR^9$, $-X^4S(O)R^{10}$, $-X^4S(O)_2R^{10}$ and $-X^4C(O)R^{10}$, wherein $X^4$ is a bond or $(C_{1-2})$alkylene, $R^9$ at each occurrence independently is hydrogen, $(C_{1-3})$alkyl or halo-substituted $(C_{1-3})$alkyl and $R^{10}$ is $(C_{1-3})$alkyl or halo-substituted $(C_{13})$alkyl; and $R^4$ is $-C(O)X^5R^{11}$ or $-S(O)_2X^5R^{11}$, wherein $X^5$ is a bond, $-O-$ or $-NR^{12}-$, wherein $R^{12}$ is hydrogen or $(C_{1-6})$alkyl, and $R^{11}$ is (i) $(C_{1-6})$alkyl optionally substituted by $-OR^{13}$, $-SR^{13}$, $-S(O)R^{13}$, $-S(O)_2R^{13}$, $-C(O)R^{13}$, $-C(O)OR^{13}$, $-C(0)NR^{13}R^{14}$, $-NR^{13}R^{14}$, $-NR^{14}C(O)R^{13}$, $-NR^{14}C(O)OR^{13}$, $-NR^{14}C(O)NR^{13}R^{14}$ or $-NR^4C(NR^{14})NR^{13}R^{14}$, wherein R13 is $(C_{3-12})$cycloalkyl$(C_{0-3})$alkyl, hetero$(C_{5-12})$cycloalkyl$(C_{0-3})$alkyl, $(C_{6-2})$aryl$(C_{0-3})$alkyl, hetero$(C_{5-12})$aryl$(C_{0-3})$alkyl, $(C_{9-12})$bicycloaryl$(C_{0-3})$alkyl or hetero$(C_{8-12})$bicycloaryl$(C_{0-3})$alkyl and $R^{14}$ at each occurrence independently is hydrogen or $(C_{1-6})$alkyl, or (ii) $(C_{3-2})$cycloalkyl$(C_{0-3})$alkyl, hetero$(C_{5-12})$cycloalkyl$(C_{0-3})$alkyl, $(C_{6-12})$aryl$(C_{0-3})$alkyl, hetero$(C_{5-12})$aryl$(C_{0-3})$alkyl, $(C_{9-12})$bicycloaryl$(C_{0-3})$alkyl or hetero$(C_{8-12})$bicycloaryl$(C_{0-3})$alkyl or (iii) $(C_{3-6})$cycloalkyl$(C_{0-3})$alkyl, hetero$(C_{5-6})$cycloalkyl$(C_{0-3})$alkyl, phenyl$(C_{0-3})$alkyl or hetero$(C_{5-6})$aryl$(C_{0-3})$alkyl substituted by $-X^6OR^{15}$, $-X^6SR^{15}$, $-X^6S(O)R^{15}$, $-X^6S(O)_2R^{15}$, $-X^6C(O)R^{15}$, $-X^6C(O)OR^{15}$, $-X^6C(O)NR^{15}R^{16}$, $-X^6NR^{15}R^{16}$, $-X^6NR^{16}C(O)R^{15}$, $-X^6NR^{16}C(O)OR^{15}$, $-X^6NR^{16}C(O)NR^{15}R^{16}$, $-X^6NR^{16}C(O)OR^{16}$, $-X^6NR^{16}C(NR^{16})NR^{15}R^{16}$, wherein $X^6$ is a bond or methylene, $R^{15}$ is $(C_{3-6})$cycloalkyl$(C_{0-3})$alkyl, hetero$(C_{5-6})$cycloalkyl$(C_{0-3})$alkyl, phenyl$(C_{0-3})$alkyl or hetero$(C_{5-6})$aryl$(C_{0-3})$alkyl and $R^{16}$ is hydrogen or $(C_{1-6})$alkyl; wherein $R^4$ optionally further contains 1 to 5 substituents which when occurring within an alicyclic or aromatic ring system are radicals independently selected from a group consisting of $(C_{1-6})$alkyl, $(C_{1-6})$alkylidene, cyano, halo, nitro, halo-substituted $(C_{1-3})$alkyl, —$X^6NR^{17}R^{17}$, —$X^6NR^{17}C(O)OR^{17}$, —$X^6NR^{17}C(O)NR^{17}R^{17}$, —$X^6NR^{17}C(NR^{17})NR^{17}R^{17}$, —$X^6OR^{17}$, —$X^6SR^{17}$, —$X^6C(O)OR^{17}$, —$X^6C(O)NR^{17}R^{17}$, —$X^6S(O)_2NR^{17}R^{17}$, —$X^6P(O)(OR^{18})OR^{17}$, —$X^6OP(O)(OR^{18})OR^{17}$, —$X^6NR^{17}C(O)R^{18}$, —$X^6S(O)R^{18}$, —$X^6S(O)_2R^{18}$ and —$X^6C(O)R^{18}$ and when occurring within an aliphatic moiety are radicals independently selected from a group consisting of cyano, halo, nitro, —$NR^{17}R^{17}$, —$NR^{17}C(O)NR^{17}R^{17}$, —$NR^{17}C(O)NR^{17}R^{17}$, —$NR^{17}C(NR^{17})NR^{17}R^{17}$, —$OR^{17}$, —$SR^{17}$, —$C(O)OR^{17}$, —$C(O)NR^{17}R^{17}$,—$S(O)_2NR^{17}R^{17}$, —$P(O)(OR^{17})OR^{17}$,—$OP(O)(OR^{17})OR^{17}$, —$NR^{17}C(O)R^{18}$, —$S(O)R^{18}$, —$S(O)_2R^{18}$ and —$C(O)R^{18}$, wherein $X^6$ is a bond or $(C_{1-6})$alkylene, $R^{17}$ at each occurrence independently is hydrogen, $(C_{1-6})$alkyl or halo-substituted $(C_{1-3})$alkyl and $R^{18}$ is $(C_{1-6})$alkyl or halo-substituted $(C_{1-3})$alkyl;

$X^3$ is a group of Formula (a):

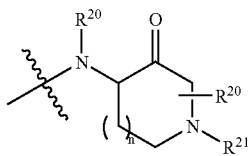

(a)

n is 0, 1 or 2;

$R^{20}$ is selected from the group consisting of hydrogen, $(C_{1-6})$alkyl, $(C_{3-12})$cycloalkyl$(C_{0-6})$alkyl, hetero$(C_{5-12})$cycloalkyl$(C_{0-6})$alkyl, $(C_{6-12})$aryl$(C_{0-6})$alkyl and hetero$(C_{5-12})$aryl$(C_{0-6})$alkyl;

$R^{21}$ is selected from the group consisting of hydrogen, $(C_{1-9})$alkyl, $(C_{3-12})$cycloalkyl$(C_{0-6})$alkyl, hetero$(C_{5-12})$cycloalkyl$(C_{0-6})$alkyl, $(C_{6-12})$aryl$(C_{0-6})$alkyl, hetero$(C_{5-12})$aryl$(C_{0-6})$alkyl, $(C_{9-12})$bicycloaryl$(C_{0-3})$alkyl, hetero$(C_{8-12})$-bicycloaryl$(C_{0-3})$alkyl, —$C(O)R^{26}$, —$C(S)R^{26}$, —$S(O)_2R^{26}$, —$C(O)OR^{26}$, —$C(O)N(R^{26})R^{27}$,—$C(S)N(R^{26})R^{27}$ and —$S(O)_2N(R^{27})R^{26}$;

$R^{26}$ is selected from the group consisting of hydrogen, $(C_{1-6})$alkyl, $(C_{3-12})$cycloalkyl$(C_{0-6})$alkyl, hetero$(C_{5-12})$cycloalkyl$(C_{0-6})$alkyl, $(C_{6-12})$aryl$(C_{0-6})$alkyl, hetero$(C_{5-12})$aryl$(C_{0-6})$alkyl, $(C_{9-12})$bicycloaryl$(C_{0-3})$alkyl and hetero$(C_{8-12})$—bicycloaryl $(C_{0-3})$alkyl;

$R^{27}$ is hydrogen, $(C_{1-6})$alkyl, $(C_{3-12})$cycloalkyl$(C_{0-6})$alkyl, hetero$(C_{5-12})$cycloalkyl$(C_{0-6})$alkyl, $(C_{6-12})$aryl$(C_{0-6})$alkyl or hetero$(C_{5-12})$aryl$(C_{0-6})$alkyl;

wherein $X^3$ optionally further contains 1 to 5 substituents which when occurring within an alicyclic or aromatic ring system are radicals independently selected from a group consisting of $(C_{1-6})$alkyl, $(C_{1-6})$alkylidene, cyano, halo, nitro, halo-substituted $(C_{1-3})$alkyl, —$X^6NR^{17}R^{17}$, —$X^6NR^{17}C(O)OR^{17}$, —$X^6NR^{17}C(O)NR^{17}R^{17}$, —$X^6NR^{17}C(NR^{17})NR^{17}R^{17}$, —$X^6OR^{17}$, —$X^6C(O)R^{17}$,—$X^6OR^{15}$,—$X^6SR^{17}$,—$X^6C(O)OR^{17}$, —$X^6C(O)NR^{17}R^{17}$, —$X^6S(O)_2NR^{17}R^{17}$, —$X^6P(O)(OR^8)OR^{17}$, —$X^{X6}OP(O)(OR^8)OR^{17}$, —$X^6NR^{17}C(O)R^{18}$, —$X^6S(O)R^{18}$, —$X^6S(O)_2R^{18}$ and —$X^6C(O)R^{18}$ and when occurring within an aliphatic moiety are radicals independently selected from a group consisting of cyano, halo, nitro, —$NR^{17}R^{17}$, —$NR^{17}C(O)OR^{17}$, —$NR^{17}C(O)NR^{17}R^{17}$, —$NR^{17}C(NR^{17})NR^{17}R^{17}$, —$OR^{17}$, —$SR^{17}$, —$C(O)OR^{17}$, —$C(O)NR^{17}R^{17}$, —$S(O)_2NR^{17}R^{17}$, —$P(O)(OR^{17})OR^{17}$, —$OP(O)(OR^{17})OR^{17}$, —$NR^{17}C(O)R^{18}$, —$S(O)R^{18}$, —$S(O)_2R^{18}$ and —$C(O)R^{18}$, wherein $R^{15}$, $R^{17}$, $R^{18}$ and $X^6$ are as described above; said process comprising:

(A) reacting a compound of Formula 2:

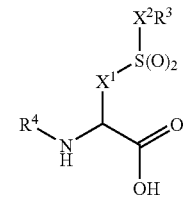

2 with a compound of the formula (a):

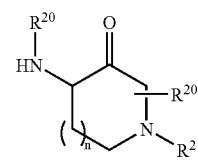

(a)

in which $X^1$, $X^2$, $R^3$, $R^4$, $R^{20}$ and $R^{21}$ are the same as defined above for Formula I; and (B) optionally converting a compound of Formula I into a pharmaceutically acceptable salt; or (C) optionally converting a salt form of a compound of Formula I to a non-salt form; or (D) optionally converting an unoxidized form of a compound of Formula I into a pharmaceutically acceptable N-oxide; or (E) optionally converting an N-oxide form of a compound of Formula I into an unoxidized form; or (F) optionally resolving an individual stereoisomer of a compound of Formula I from a mixture of stereoisomers; or (G) optionally converting a non-derivatized compound of Formula I into a pharmaceutically acceptable prodrug derivative; or (H) optionally converting a prodrug derivative of a compound of Formula I to a non-derivatized form.

12. A compound of Formula Ix:

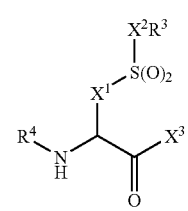

Ix in which:

$X^1$ and $X^2$ are both methylene or $X^1$ is ethylene and $X^2$ is a bond;

$R^3$ is —$CR^5$=$CHR^6$, —$CR^5(CR^6_3)_2$ or —$CR^7$=$NR^8$, wherein $R^5$ is hydrogen and $R^6$ is hydrogen or $(C_{1-4})$alkyl or $R^5$ and $R^6$ together with the atoms to which $R^5$ and $R^6$ are attached form $(C_{3-12})$cycloalkenyl, hetero$(C_{5-12})$cycloalkenyl, $(C_{6-12})$aryl, hetero$(C_{6-12})$aryl, $(C_{9-12})$bicycloaryl or hetero$(C_{8-12})$bicycloaryl and $R^7$ and $R^8$ together with the atoms to which $R^7$ and $R^8$ are attached form hetero$(C_{5-12})$cycloalkenyl, hetero$(C_{6-12})$aryl or hetero$(C_{8-12})$bicycloaryl, wherein $R^3$ optionally is substituted by 1 to 5 radicals independently selected from a group consisting of $(C_{1-4})$alkyl, cyano, halo, halo-substituted $(C_{1-4})$alkyl, nitro, —$X^4NR^9R^9$, —$X^4OR^9$, —$X^4SR^9$, —$X^4C(O)NR^9R^9$, —$X^4C(O)OR^9$, —$X^4S(O)R^{10}$, —$X^4S(O)_2R^{10}$ and —$X^4C(O)R^{10}$, wherein $X^4$ is a bond or ($C_{1-2}$)alkylene, $R^9$ at each occurrence independently is hydrogen, ($C_{1-3}$)alkyl or halo-substituted ($C_{1-3}$)alkyl and $R^{10}$ is ($C_{1-3}$)alkyl or halo-substituted ($C_{1-3}$)alkyl; and $R^4$ is —$C(O)X^5R^{11}$ or —$S(O)_2X^5R^{11}$, wherein $X^5$ a bond, —O— or —$NR^{12}$—, wherein $R^{12}$ is hydrogen or ($C_{1-6}$)alkyl, and $R^{11}$ is (i) ($C_{1-6}$)alkyl optionally substituted by —$OR^{13}$, —$SR^{13}$, —$S(O)R^{13}$, —$S(O)_2R^{13}$, —$C(O)R^{13}$, —$C(O)OR^{13}$, —$C(O)NR^{13}R^{14}$, —$NR^{13}R^{14}$, —$NR^{14}C(O)R^{13}$, —$NR^{14}C(O)OR^{13}$, —$NR^{14}C(O)NR^{13}R^{14}$ or —$NR^{14}C(NR^{14})NR^{13}R^{14}$, wherein $R^{13}$ is ($C_{3-12}$)cycloalkyl($C_{0-3}$)alkyl, hetero($C_{5-12}$)cycloalkyl($C_{03}$)alkyl, ($C_{6-12}$)aryl($C_{0-3}$)alkyl, hetero($C_{5-12}$)aryl($C_{0-3}$)alkyl, ($C_{9-12}$)bicycloaryl($C_{03}$)alkyl or hetero($C_{8-12}$)bicycloaryl($C_{0-3}$)alkyl and $R^{14}$ at each occurrence independently is hydrogen or ($C_{1-6}$)alkyl, or (ii) ($C_{3-12}$)cycloalkyl($C_{03}$)alkyl, hetero($C_{5-12}$)cycloalkyl($C_{03}$)alkyl, ($C_{6-12}$)aryl($C_{0-3}$)alkyl, hetero($C_{5-12}$)aryl($C_{0-3}$)alkyl, ($C_{9-12}$)bicycloaryl($C_{0-3}$)alkyl or hetero($C_{8-12}$)bicycloaryl($C_{0-3}$)alkyl or (iii) ($C_{3-6}$)cycloalkyl($C_{0-3}$)alkyl, hetero($C_{5-6}$)cycloalkyl($C_{0-3}$)alkyl, phenyl($C_{0-3}$)alkyl or hetero($C_{5-6}$)aryl($C_{0-3}$)alkyl substituted by —$X^6OR^{15}$, —$X^6SR^{15}$, —$X^6S(O)R^{15}$, —$X^6S(O)_2R^{15}$, —$X^6C(O)R^{15}$, —$X^6C(O)OR^{15}$, —$X^6C(O)NR^{15}R^{16}$, —$X^6NR^{15}R^{16}$, —$X^6NR^{16}C(O)R^{15}$, —$X^6NR^{16}C(O)OR^{15}$, —$X^6NR^{16}C(O)NR^{15}R^{16}$, —$X^6NR^{16}C(O)OR^{16}$, —$X^6NR^{16}C(NR^{16})NR^{15}R^{16}$, wherein $X^6$ is a bond or methylene, $R^{15}$ is ($C_{3-6}$)cycloalkyl($C_{0-3}$)alkyl, hetero($C_{5-6}$)cycloalkyl($C_{0-3}$)alkyl, phenyl($C_{0-3}$)alkyl or hetero($C_{5-6}$)aryl($C_{0-3}$)alkyl and $R^{16}$ is hydrogen or ($C_{1-6}$)alkyl; wherein $R_4$ optionally further contains 1 to 5 substituents which when occurring within an alicyclic or aromatic ring system are radicals independently selected from a group consisting of ($C_{1-6}$alkyl, ($C_{1-6}$)alkylidene, cyano, halo, nitro, halo-substituted ($C_{1-3}$)alkyl, —$X^6NR^{17}R^{17}$, —$X^6NR^7C(O)OR^{17}$, —$X^6NR^{17}C(O)NR^{17}R$, —$XNR^{17}C(NR^{17})NR^{17}R^{17}$, —$X^6OR^{17}$, —$X^6SR^{17}$, —$X^6C(O)OR^{17}$, —$X^6C(O)NR^{17}R^{17}$, —$X^6S(O)_2NR^{17}R^{17}$, —$X^6P(O)(OR^{18})OR^{18}$, —$X^6OP(O)(OR^{18})OR^{17}$, —$X^6NR^{17}C(O)R^{18}$, —$X^6S(O)R^{18}$, —$X^6S(O)_2R^{18}$ and $X^6C(O)R^{18}$ and when occurring within an aliphatic moiety are radicals independently selected from a group consisting of cyano, halo, nitro, —$NR^{17}R^{17}$, —$NR^{17}C(O)OR^{17}$, —$NR^{17}C(O)NR^{17}R^{17}$, —$NR^{17}C(NR^{17})NR^{17}R^{17}$, —$OR^{17}$, —$SR^{17}$, —$C(O)OR^{17}$, —$C(O)NR^{17}R^{17}$, —$S(O)_2NR^{17}R^{17}$, —$P(O)(OR^{17})OR^{17}$, —$OP(O)(OR^{17})OR^{17}$, —$NR^{17}C(O)R^{18}$, —$S(O)R^{18}$, —$S(O)_2R^{18}$ and —$C(O)R^{18}$, wherein $X^6$ is a bond or ($C_{1-6}$)alkylene, $R^{17}$ at each occurrence independently is hydrogen, ($C_{1-6}$)alkyl or halo-substituted ($C_{1-3}$)alkyl and $R^{18}$ is ($C_{1-6}$)alkyl or halo-substituted ($C_{1-3}$)alkyl;

$X^3$ is a group of Formula (a):

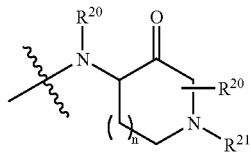

(a)

n is 0, 1 or 2;

$R^{20}$ is selected from the group consisting of hydrogen, ($C_{1-6}$)alkyl, ($C_{3-12}$)cycloalkyl($C_{0-6}$)alkyl, hetero($C_{5-12}$)cycloalkyl($C_{0-6}$)alkyl, ($C_{6-12}$)aryl($C_{0-6}$)alkyl and hetero($C_{5-12}$)aryl($C_{0-6}$)alkyl;

$R^{21}$ is selected from the group consisting of hydrogen, ($C_{1-9}$)alkyl, ($C_{3-12}$)cycloalkyl($C_{0-6}$)alkyl, hetero($C_{5-12}$)cycloalkyl($C_{0-6}$)alkyl, ($C_{6-12}$)aryl($C_{0-6}$)alkyl, hetero($C_{5-12}$)aryl($C_{0-6}$)alkyl, ($C_{9-12}$)bicycloaryl($C_{0-3}$)alkyl, hetero($C_{8-12}$)-bicycloaryl($C_{0-3}$)alkyl, —$C(O)R^{26}$, —$C(S)R^{26}$, —$S(O)_2R^{26}$, —$C(O)OR^{26}$, —$C(O)N(R^{26})R^{27}$, —$C(S)N(R^{26})R^{27}$ and —$S(O)2N(R^{27})R^{26}$;

$R^{26}$ is selected from the group consisting of hydrogen, ($C_{1-6}$)alkyl, ($C_{3-12}$)cycloalkyl($C_{0-6}$)alkyl, hetero($C_{5-12}$)cycloalkyl($C_{0-6}$)alkyl, ($C_{6-12}$)aryl($C_{0-6}$)alkyl, hetero($C_{5-12}$)aryl($C_{0-6}$)alkyl, ($C_{9-12}$)bicycloaryl($C_{0-3}$)alkyl and hetero($C_{8-12}$)-bicycloaryl($C_{0-3}$)alkyl;

$R^{27}$ is hydrogen, ($C_{1-6}$)alkyl, ($C_{3-12}$)cycloalkyl($C_{0-6}$)alkyl, hetero($C_{5-12}$)cycloalkyl($C_{0-6}$)alkyl, ($C_{6-12}$)aryl($C_{0-6}$)alkyl or hetero($C_{5-12}$)aryl($C_{0-6}$)alkyl;

wherein $X^3$ optionally further contains 1 to 5 substituents which when occurring within an alicyclic or aromatic ring system are radicals independently selected from a group consisting of ($C_{1-6}$)alkyl, ($C_{1-6}$)alkylidene, cyano, halo, nitro, halo-substituted ($C^{13}$)alkyl, —$X^6NR^{17}R^{17}$, —$X^6NR^{17}C(O)OR^{17}$, —$X^6NR^{17}C(O)NR^{17}R^{17}$, —$X^6NR^{17}C(NR^{17})NR^{17}R^{17}$, —$X^6OR^{17}$, —$X^6C(O)R^{17}$, —$X^6OR^{15}$, —$X^6SR^{17}$, —$X^6C(O)OR^{17}$, —$X^6C(O)NR^{17}R^{17}$, —$X^6S(O)_2NR^{17}R^{17}$, —$X^6P(O)(OR^8)OR^{17}$, —$X^6OP(O)(OR^8)OR^{17}$, —$X^6NR^{17}C(O)R^{18}$, —$X^6S(O)R^{18}$, —$X^6S(O)_2R^{18}$ and —$X^6C(O)R^{18}$ and when occurring within an aliphatic moiety are radicals independently selected from a group consisting of cyano, halo, nitro, —$NR^{17}R^{17}$, —$NR^{17}C(O)OR^{17}$, —$NR^{17}C(O)NR^{17}R^{17}$, —$NR^{17}C(NR^{17})NR^{17}R^{17}$, —$OR^{17}$, —$SR^{17}$, —$C(O)OR^{17}$, —$C(O)NR^{17}R^{17}$, —$S(O)_2NR^{17}R^{17}$, —$P(O)(OR^{17})OR^{17}$, —$OP(O)(OR^{17})OR^{17}$, —$NR^{17}C(O)R^{18}$, —$S(O)R^{18}$, $S(O)_2R^{18}$ and —$C(O)R^{18}$, wherein $R^{15}$, $R^{17}$, $R^{18}$ and $X^6$ are as described above; or one of N-oxide derivatives, prodrug derivatives, protected derivatives, individual isomers and mixtures of isomers of compounds of formula Ix; or one of pharmaceutically acceptable salts and solvates of such compounds and the N-oxide derivatives, prodrug derivatives, protected derivatives, individual isomers and mixtures of isomers formula Ix.

13. A compound of claim 12, selected from the group consisting of:

Morpholine-4-carboxylic acid [1-(1-benzoyl-4-oxo-pyrrolidin-3-ylcarbamoyl)-2-phenylmethanesulfonyl-ethyl]-amide;

Morpholine-4-carboxylic acid [1-(1-benzenesulfonyl-4-oxo-pyrrolidin-3-ylcarbamoyl) 2-phenylmethanesulfonyl-ethyl]-amide;

4-{2-[(Morpholine-4-carbonyl)-amino]-3-phenyl-methanesulfonyl-propionylamino}-3-oxo-azepane-1-carboxylic acid benzyl ester; or Acetic acid 3-{2-[(morpholine-4-carbonyl)-amino]-3-phenylmethanesulfonyl-propionylamino}-4-oxo-azetidin-2-yl ester.

* * * * *